(12) United States Patent
Graham

(10) Patent No.: US 12,084,671 B2
(45) Date of Patent: Sep. 10, 2024

(54) OPTIMIZED CRISPR-Cas NUCLEASES AND BASE EDITORS AND METHODS OF USE THEREOF

(71) Applicant: Pairwise Plants Services, Inc., Durham, NC (US)

(72) Inventor: Nathaniel Graham, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 18/164,910

(22) Filed: Feb. 6, 2023

(65) Prior Publication Data

US 2023/0183726 A1 Jun. 15, 2023

Related U.S. Application Data

(63) Continuation of application No. 17/078,576, filed on Oct. 23, 2020, now Pat. No. 11,591,607.

(60) Provisional application No. 62/925,422, filed on Oct. 24, 2019.

(51) Int. Cl.
  *C12N 15/82* (2006.01)
  *C12N 9/22* (2006.01)
  *C12N 15/113* (2010.01)

(52) U.S. Cl.
  CPC ........... *C12N 15/8218* (2013.01); *C12N 9/22* (2013.01); *C12N 15/113* (2013.01); *C12N 2310/20* (2017.05)

(58) Field of Classification Search
  None
  See application file for complete search history.

(56) References Cited

U.S. PATENT DOCUMENTS

| | | | |
|---|---|---|---|
| 11,345,924 B2 * | 5/2022 | Gao | C12N 15/8274 |
| 2014/0283200 A1 | 9/2014 | Chittoor et al. | |
| 2015/0191721 A1 * | 7/2015 | Kelker | C12N 15/63 |
| | | | 536/23.6 |
| 2016/0068864 A1 | 3/2016 | Doudna et al. | |
| 2017/0218384 A1 | 8/2017 | Abbitt et al. | |
| 2018/0073012 A1 | 3/2018 | Liu et al. | |
| 2018/0327784 A1 | 11/2018 | Jin et al. | |
| 2019/0292553 A1 | 9/2019 | Gao et al. | |
| 2020/0080090 A1 | 3/2020 | Cereseto et al. | |

FOREIGN PATENT DOCUMENTS

WO    2019067910 A1    4/2019

OTHER PUBLICATIONS

Lu, Yuming, and Jian-Kang Zhu. "Precise editing of a target base in the rice genome using a modified CRISPR/Cas9 system." Molecular plant 10.3 (2017): 523-525. (Year: 2017).*
Christensen, Alan H., and Peter H. Quail. "Ubiquitin promoter-based vectors for high-level expression of selectable and/or screenable marker genes in monocotyledonous plants." Transgenic research 5 (1996): 213-218. (Year: 1996).*
Li, Chao, et al. "Expanded base editing in rice and wheat using a Cas9-adenosine deaminase fusion." Genome biology 19 (2018): 1-9. (Year: 2018).*
International Search Report and the Written Opinion of the International Searching Authority corresponding to International Patent Application No. PCT/US20/56963 (13 pages) (mailed Mar. 3, 2021).
Christensen, Alan H., et al., "Ubiquitin promoter-based vectors for high-level expression of selectable and/or screenable marker genes in monocotyledonous plants", Transgenic Research, 5, 1996, 213-218.
Endo, Masaki , et al., "Genome editing in plants by engineered CRISPR-Cas9 recognizing NG PAM", Nature Plants 5, 2019, 14-17.
Genbank , "Cas9D10A nickase [Cloning vector pVIR-Nick]", GenBank: AWD73737.1; Retrieved from: https://www.ncbi.nlm.nih.gov/protein/AWD73737.1/, 2018, (1 page).
Hua, Kai, et al., "Expanding the base editing scope in rice by using Cas9 variants", Plant Biotechnology Journal 17(2), 2019, 499-504.
Jin, Shuai , et al., "Cytosine, but not adenine, base editors induce genome-wide off-target mutations in rice", Science 364(6437), 2019, 292-295.
Komor, Alexis C., et al., "Programmable editing of a target base in genomic DNA without double-stranded DNA cleavage", Nature, 533, 2016, 420-424.
Li, Jingying , et al., "Generation of Targeted Point Mutations in Rice by a Modified CRISPR/Cas9 System", Molecular Plant: Letter to the Editor 10(3), 2016, 526-529.
Lu, Yuming , et al., "Precise Editing of a Target Base in the Rice Genome Using a Modified CRISPR/Cas9 System", Molecular Plant: Letter to the Editor 10 (3), 2017, 523-525.
Mauro, Vincent P., et al., "A critical analysis of codon optimization in human therapeutics", Trends in Molecular Medicine, 20(11), 2014, 604-613.
Xue, Chenxiao , et al., "Manipulating mRNA splicing by base editing in plants", Science China Life Sciences 61(11), 2018, 1293-1300.
Zong, Yuan , et al., "Precise base editing in rice, wheat and maize with a Cas9-cytidine deaminase fusion", Nature Biotechnology 35(5), 2017, 438-440.

* cited by examiner

*Primary Examiner* — Weihua Fan
(74) *Attorney, Agent, or Firm* — Myers Bigel, P.A.

(57) ABSTRACT

This invention relates to CRISPR-Cas nucleases codon optimized for expression in plants and nucleic acid constructs encoding base editors comprising a CRISPR-Cas nuclease and a deaminase domain, wherein the nucleic acid constructs are optimized for expression in a plant. The invention further relates to methods of modifying nucleic acids using the nucleic acid constructs.

19 Claims, 3 Drawing Sheets

Specification includes a Sequence Listing.

SEQUENCE LISTING

```
Sequence total quantity: 76
SEQ ID NO: 1             moltype = DNA  length = 4101
FEATURE                  Location/Qualifiers
misc_feature             1..4101
                         note = Cas9 polynucleotide
source                   1..4101
                         mol_type = other DNA
                         organism = synthetic construct
SEQUENCE: 1
gacaagaagt acagcatcgg gctggcgatc gggaccaact ccgtcggctg ggctgtgatt   60
accgacgagt acaaggtgcc atccaagaag ttcaaggtcc tcggcaacac tgaccggcac  120
agcattaaga gaacctgat tggggcgctg ctgttcgatt cggggagac tgcggaggcg   180
accaggctga agcggactgc gcgccggagg tacaccagga ggaagaatcg gatctgctac  240
ctccaggaga tttttctcgaa tgagatgcc aaggtggacg attccttctt ccatcgcctg  300
gaggagtcgt tcctcgttga ggaggacaag aagcatgaga ggcatcccat tttcgggaat  360
atcgttgacg aggtggctta ccatgagaag tacccgacca tctaccatct gcggaagaag  420
ctcgtcgatt cgaccgataa ggccgacctg cggctgatct acctggccct cgcgcacatg  480
attaagttcc ggggccattt cctcatcgag ggcgacctca acccggacaa ctcggacgtg  540
gataagctct tcattcagct cgtgcagaca taaccagc tcttcgagga gaatcccatt  600
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720
attgccctgt cgctggggct cacaccgaat ttcaagtcga acttcgacct cgccgaggac  780
gctaagctcc agctcagcaa ggatacttac gatgatgacc tcgataacct gctcgcccag  840
attggggatc agtacgcgga tctgttcctc gcggccaaga atctcagcga tgctattctc  900
ctgtcggaca tttccgcgt caacacagag attactaagg ccccactgtc ggcgagcatg  960
attaagaggt acgatgagca tcatcaggac ctgacactgc tcaaggcgct ggtccggcag 1020
cagctccccg agaagtacaa ggagattttc ttcgatcagt caaagaatgg gtacgcgggc 1080
tacattgatg gcggcgcgtc ccaggaggag ttctacaagt tcattaagcc catcctggag 1140
aagatggacg ggaccgagga gctgctggtg aagctcaatc gggaggacct gctccggaag 1200
cagcgcacat tcgacaatgg ctcgattcct caccagattc acctgggcga gctgcacgcc 1260
attctccgca ggcaggagga cttctacccg ttcctcaagg acaaccgcga gaagatcgag 1320
aagatcctga ccttccggat tccatactac gtggggcgc tcgcgcgggg gaactcccgg 1380
ttcgcgtgga tgactcgcaa gtccgaagaa acgattacac cgtggaattt cgaggaggtc 1440
gtcgacaagg gcgctagtgc gcagtcattc attgagagga tgaccaattt cgataagaac 1500
ctgcctaacg agaaggtgct gccgaagcat tcgctgctct acgagtactt caccgtttac 1560
aatgagctga ccaaggtgaa gtatgtgact gagggcatga ggaagccagc gttcctgagc 1620
ggcgagcaga agaaggctat cgtggacctg ctcttcaaga ctaaccggaa ggtgactgtg 1680
aagcagctca aggaggacta cttcaagaag attgagtgct tcgattccgt tgagattagc 1740
ggggtggagg atcggttcaa tgcttcgctc gggacatacc acgatctcct gaagatcatt 1800
aaggataagg acttcctcga caacgaggag aacgaggaca ttctcgaaga tattgtcctg 1860
acccctcacc tcttcgagga tcgggagatg atcgaggaga ggctcaagac atacgctcat 1920
ctgttcgatg ataaggtcat gaagcagctg aagcgcaggc ggtacacagg gtgggggcgg 1980
ctgagccgga agctgatcaa cgggattcgg gataagcagt ccgggaagac aattctcgac 2040
ttcctcaagt ccgacgggtt cgctaaccgg aacttcatgc agctcattca tgatgactgc 2100
ctgacattca aggaggatat tcagaaggcg caggtttcgg ggcagggcga ctcgctccac 2160
gagcatattg cgaatctggc gggctccccc gcgattaaga agggcattct gcaaaccgtc 2220
aaggtggttg atgagctggt caaggtcatg ggcggcata agccagagaa tattgtcatc 2280
gagatggcgc gggagaatca gaccacacag aaggggcaga agaactcacg ggagcggatg 2340
aagcgcatcg aggagggcat caaggagctg gggtcgcaga tcctgaagga gcatcccgtg 2400
gagaacactc agctgcaaaa tgagaagctg tacctctact acctccagaa cgggagggac 2460
atgtatgtgg atcaggagct ggatattaat aggctgagcg attacgatgt cgaccacatt 2520
gtcccacagt cgttcctgaa ggacgacagc attgacaaca aggtgctgac ccgctcggat 2580
aagaacaggg gcaagagcga taatgttcca agcgaggagg ttgtgaagaa gatgaagaac 2640
tactggcggc agctcctgaa cgcgaagctc atcacacagc ggaagttcga caacctcacc 2700
aaggctgagc gcggggccct gagcgagctg gacaaggcgg ggttcattaa gaggcagctg 2760
gtcgagacac ggcagattac aaagcatgtt gcgcagattc tcgattcccg gatgaacacc 2820
aagtacgatg agaacgataa gctgattcgg gaggtcaagg taattaccct gaagtccaag 2880
```

```
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg aagaggccc   3180
ctcatcgaga caaatgggga gacaggggag attgtctggg ataaggggcg ggatttcgcg  3240
accgtccgga aggtcctgtc gatgccccag gttaatattg tcaagaagac tgaggtccag  3300
actggcggct tctcaaagga gtcgattctc caaagagga actccgataa gctcattgct   3360
cggaagaagg attgggaccc caagaagtac ggggattcg actccccac tgttgcttac    3420
tctgttctgg ttgttgctaa ggtggagaag gggaagtcga agaagctgaa gagcgtgaag  3480
gagctgctcg ggattacaat tatggagagg tcatccttcg agaagaatcc catcgacttc  3540
ctggaggcca agggctacaa ggaggtgaag aaggacctga ttattaagct gcccaagtac  3600
tcgctcttcg agctggagaa tgggcggaag cggatgctgg cgtccgcggg ggagctgcaa  3660
aaggggaacg agctggcgct cccctccaag tatgtgaact tcctctacct ggcgtcgcac  3720
tacgagaagc tgaaggggtc cccagaggat aatgagcgaa agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                             4101

SEQ ID NO: 2            moltype = DNA   length = 4101
FEATURE                 Location/Qualifiers
misc_feature            1..4101
                        note = Cas9 polynucleotide
source                  1..4101
                        mol_type = other DNA
                        organism = synthetic construct
SEQUENCE: 2
gacaagaagt actccattgg cctggcgatt gggacaaact cggtgggtg ggccgtgatt    60
acggatgagt acaaggttcc aagcaagaag ttcaaggtcc tcgggaacac agatcggcat   120
tcgattaaga gaatctcat tggggcgctc ctcttcgact cggggagac agcggaggct    180
accaggctca agcggacagc caggcggcgg tacacaaggc ggaagaatcg catctgctac   240
ctccaggaga ttttctcgaa tgagatggcg aaggtggacg acagcttctt ccatcgcctg   300
gaggagtcct tcctggtgga ggaggataag aagcacgaga ggcatccaat tttcgggaac   360
atcgtggacg aggttgcgta ccatgagaag taccctacaa tctaccatct gcggaagaag   420
ctggttgact ccacagacaa ggcggacctg aggctgatct acctcgctct ggcccacatg   480
attaagttcc gcgggcattt cctgatcgag ggggacctga atccgacaa ttcggatgtg   540
gacaagctct tcatccagct ggtgcagacc tacaaccagc tgttcgagga gaatcccatc   600
aatgcgtcgg gcgttgacgc taaggccatt ctgtccgcta ggctgtcgaa gagcaggagg  660
ctggagaacc tgatcgccca gctgccaggc gagaagaaga tgggctctt cggaatctg    720
attgcgctct ccctggggct gacaccgaac ttcaagacga atttcgatct ggctgaggac  780
gcgaagctcc agctctcgaa ggacacttac gacgatgacc tcgataacct cctcgcgcag  840
atcgggacc agtacgctga tctcttcctc gccgctaaga acctctcgga tgctatcctg   900
ctctccgaca ttctccgggt taataccgag attacaaagg ccccactgtc ggcgtccatg   960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctggggga gctgcacgcg  1260
atcctgcgcc ggcaggagga tttctaccct ttcctgaagg ataatcggga gaagatcgag  1320
aagattctca ccttccggat tcctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagccgc gttcctgtcc   1620
ggcgagcaga gaaggccat tgtggacctc tgttcaaga ccaatcgcaa ggtcacagtc    1680
aagcagctca aggaggatta cttcaagaag atcgagtgct tcgactcggt tgagattagc  1740
gggtgggagg atcggttcaa cgcgagcctc ggcacttacc acgacctctc gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cgggatcagg gacaagcaga cggaagcgac tccgacgtgt  2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcg gggagaatca gaccactcag aagggccaga agaactcgcg ggagcgcatg  2340
aagaggatcg aggagggat taaggagctg ggcagccaga ttctcaagga gcaccccgtg  2400
gagaataccc agctccagaa cgagaagctg tacctctact acctcagaa tgggcggac    2460
atgtatgttg atcaggagct ggacatcaat cgcctctcgg attacgacgt ggaccacatc  2520
gtgcccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacgg gaagttcga taacctgacg  2700
aaggcggaga gggcggcct ccgagctg acaagcgg gcttcattaa gaggcagctc      2760
gtggagactc gccagatcac caagcacgtg gctcagatcc tcgatagccg gatgaatacg  2820
aagtacgatg agaatgacaa gctcatccgg gaggtgaagg taatcacct gaagtcaaag  2880
ctcgttagcg atttccggaa ggacttccag ttctacaagg tgcgggagat taacaactac  2940
```

```
catcatgcgc acgatgcgta cctcaatgcg gtggtgggca cagccctgat taagaagtac    3000
cccaagctgg agagcgagtt cgtctacggg gactacaagg tgtacgatgt tcggaagatg    3060
atcgccaaga gcgagcagga gattgggaag gccaccgcta agtacttctt ctactcgaat    3120
attatgaatt tcttcaagac cgagatcaca ctcgctaatg gggagattcg gaagcggccc    3180
ctcatcgaga ctaacgggga gactggcgaa atttgtgttg acaagggggcg cgacttcgct    3240
accgtgcgca aggtcctctc gatgcccccag gttaatattg ttaagaagac agaggtgcag    3300
acgggcgggt tctccaagga gtctatcctg ccgaagcgga actcggacaa gctgatcgcc    3360
cgcaagaagg attgggaccc caagaagtac ggggggattcg atagcccaac cgtggccttac    3420
agcgtcctgg tggtcgccaa ggttgagaag gggaagtcga agaagctcaa gagcgttaag    3480
gagctgctgg gcatcaccat catggagcgg tccagcttcg agaagaatcc tatcgacttc    3540
ctggaggcta aggggtacaa ggaggtcaag aaggacctga tcattaagct gcccaagtac    3600
tctctgttcg agctggagaa cgggaggaag cggatgctgg cgtctgctgg cgagctacag    3660
aagggcaatg agctggcgct ccctcgaag tatgtcaact tcctctacct ggcttccat      3720
tacgagaagc tgaagggctc gcccgaggat aatgagcaga agcagctctt cgtggagcag    3780
cacaagcact acctcgacga gatcattgag cagatttcgg agttctcgaa gcgggtcatt    3840
ctcgcggacg cgaacctcga caaggtcctc tcggcgtaca caagcaccg ggacaagccc     3900
atcccgggagc aggccgagaa cattatccac ctcttcacac tgaccaacct cggcgctccc   3960
gccgcgttca agtacttcga caccaccatt gaccgcaaga gatacacatc caccaaggag    4020
gtgctggacg cgaccctcat ccaccagagc atcacaggcc tctacgagac acggatcgac    4080
ctctcgcagc tcgggggcga t                                              4101

SEQ ID NO: 3           moltype = DNA  length = 4092
FEATURE                Location/Qualifiers
misc_feature           1..4092
                       note = Cas9 polynucleotide
source                 1..4092
                       mol_type = other DNA
                       organism = synthetic construct
SEQUENCE: 3
gacaagaagt actcgatcgg cctggcgatt ggcacaaaca gcgtgggggtg ggctgtgatc    60
actgatgagt acaaggtgcc atcgaagaag ttcaaggtgc tggggaatac agaccggcat    120
tcgatcaaga agaatctcat tggcgctctc ctcttcgatt ccggcgagac tgctgaggcg    180
acccgcctga agcgcaccgc ccggcggcgc tacactcggc ggaagaatag gatttgctac    240
ctccaggaga ttttctcgaa tgagatggcc aaggtggatg acagcttctt ccaccgcctg    300
gaggagtcgt tcctggtcga ggaggacaag aagcatgagc ggcacccat cttcgggaat     360
atcgttgatg aggtcgccta ccacgagaag taccccacta tctaccatct ccgcaagaag    420
ctcgtggaca gcacagataa ggccgacctc cgcctgatct acctcgccct cgcgcacatg    480
attaagttcc ggggggcactt cctcattgag ggggatctga atcccgataa ctccgacgtg   540
gacaagtcgt tcatccagct ggtgcagaca taccaaccagc tgttcgagga gaatcccatc   600
aacgcgagcg gcgtggacgc taaggccatt ctgtcgggcta ggctctcgaa gtcgaggcgg   660
ctggagaacc tgattgcgca gctccccggc gagaagaaga cgggctgtt cgggaatctc     720
atcgcccct ccctcggcct cacaccaaac ttcaagagca atttcgacct ggctgaggac     780
gctaagctgc aactcctgac gatgacgacc tggacaactc gggttggctc ag            840
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag    1020
cagctgcccg agaagtacaa ggagattttc ttcgatcaga agaagaatgg ctacgccggc    1080
tacatcgacg ggggcgcgag ccaggaggag ttctacaagt tcatcaagcc catcctggag    1140
aagatgacg caccgagga gctactcgtg aagctcaatc ggggaggatct cctccggaag     1200
cagcggacat tcgataacgg gtcgtatccca caccagatcc acctcggcga gctgcatgcg   1260
attctgcgcc ggcaggagga tttctacccct ttcctgaaga acaaccggaa gaagatcgaa   1320
aagatcctca cattccggga tccatactac gtcggccccc tggcgagggg caatagccgg   1380
ttcgcgtgga tgacaaggaa gtccgaggag actattaccc cgtggaattt cgaggaggtg    1440
gttgacaagg gcgcttccgc gcagagcttc attgagcgga tgacaaactt cgacaagaat    1500
ctcccccaacg agaaggtcct gccgaagcat gcctcctgt acgagtactt caccgtctac    1560
aatgagctaa ctaaggtcaa gtatgtgaca gagggcatga ggaagccagc cttcctctca    1620
ggcgagcaga agaaggccat tgtggacctc ctgttcaaga caaaccgcaa ggtgacagtg    1680
aagcagctga aggaggatta cttcaagaag atgagtgct tcgactcagt ggagatttca     1740
ggcgtggagg atcggttcaa cgcgagcctg gggacttacc acgacctgct gaagattatt    1800
aaggacaagg acttcctgga taacgaggag aatgaggaga tcctggagga tattgtgctc    1860
accctcaccc tgttcgagga cagggagatg attgaggaga ggctcaagac ctacgcgcac    1920
ctgttcgatg acaaggtcat gaagcagctg aagaggcggc gctacactgg gtggggccgc    1980
ctgtcgcgga agctgatcaa cggcattcgg gataagcagt ccgggaagac cattctggat    2040
ttcctgaagt cggacggctt cgccaacagg aatttcatgc agctgatcca cgacgactcg    2100
ctcaccttca aggaggacat tcagaaggcc caggttagcg gccaggggga ctcactccac    2160
gagcatattg ccaatctggc cggctctcca gctatcaaga agggcatcct gcaaacagtt    2220
aaggttgttg acgagctggt taaggtcatg gggcggcata agcccgagaa cattgtcatc    2280
gagatggctc gggagaacca gacaactcag aagggccaga agaactccag ggagcgcatg    2340
aagcggattg aggagggcat taaggagctg gggtcccaga tcctcaagga gcaccctgtc    2400
gagaacactc agctgcaaaa cgagaagctc tacctgtact acctccagaa cgggcgggat    2460
atgtatgtgg atcaggagct ggacatcaac aggctctccg actacgacgt ggatcacatt    2520
gtcccacagt ctttcctcaa ggatgattcc atcgacaaca aggtgctgac gcgcagcgac    2580
aagaataggg ggaagtcgga caacgttccg agcgaggagg tcgtgaagaa gatgaagaat    2640
tactgggaga agctcctgaa tgcgaagctg atcactgagg gaagttcga caatctgaca    2700
aaggcggaga gggggcgggct ctcggagctg gataaggcgg gcttcatcaa gcggcagctc    2760
gttgaaaccc ggcagatcac caagcatgtc gcccagatcc tcgatagccg catgaacacc    2820
aagtacgatg agaacgacaa gctcattcgg gaggttaagg tcattacgct gaagtccaag    2880
ctcgtcagcg acttcaggaa ggatttccag ttctacaagg ttcgggagat taacaactac    2940
caccacgcgc atgatgcgta cctgaacgct gttgtcggca ctgctctcat caagaagtac    3000
```

```
ccaaagctgg agtccgagtt cgtctacggg gactacaagg tctacgatgt ccggaagatg    3060
atcgccaagt cggagcagga gatcgggaag gctactgcga agtacttctt ctacagcaac    3120
attatgaatt tcttcaagac ggagattacg ctggcgaacg gggagattag gaagaggccc    3180
ctcattgaga ctaatgggga gacaggcgag attgtttggg acaagggccg cgacttcgcg    3240
actgtgcgga aggtcctgtc catgccacag gtgaatattg ttaagaagac agaggtgcag    3300
actgggggct tctcgaagga gagcattctc ccaaagcgga acagcgataa gctcatcgcg    3360
cgcaagaagg attgggaccc taagaagtac ggcggcttcg attctcccac tgtggcctac    3420
tccgttctcg tggttgccaa ggttgagaag gggaagtcga agaagctgaa gtcggtcaag    3480
gagctgctcg ggattacaat catggagcgg agcagcttcg agaagaaccc tattgatttc    3540
ctggaggcca agggctacaa ggaggttaag aaggatctca ttatcaagct ccctaagtac    3600
tctctgttcg agctggagaa tggccggaag aggatgctgg cctcggctgg cgagctacag    3660
aaggggaatg agctggccct cccgtcgaag tatgtgaatt tcctgtacct cgcgtcgcac    3720
tacgagaagc tcaagggcag cccggaggat aatgagcaga agcagctctt cgtggagcag    3780
cataagcact acctggacga gatcattgag cagatcgagt ccttcagcaa gcgggttatt    3840
ctggctgatg ctaacctgga caaggttctg agcgcctaca ataagcatcg cgacaagccg    3900
attcgcgagc aggcggagaa tattatccac ctgttcaccc tcactaacct cggggctccc    3960
gcggccttca gtacttcga taccacaata gataggaagc ggtacacctc gacgaaggag    4020
gtcctcgacg ccacactcat ccatcagtcg attacaggcc tgtacgagac acggattgac    4080
ctctcgcagc tg                                                        4092

SEQ ID NO: 4          moltype = DNA   length = 4101
FEATURE               Location/Qualifiers
misc_feature          1..4101
                      note = Cas9 polynucleotide
source                1..4101
                      mol_type = other DNA
                      organism = synthetic construct
SEQUENCE: 4
gacaagaagt attccatagg cctggctatc ggcaccaaca gcgtgggctg ggccgtcatc    60
accgacgagt acaaagtgcc gagtaaaaag ttcaaagtgc tcggcaacac cgaccgccac    120
tccataaaga aaaacctgat cggggcgctc ctgttcgaca gcggcagac ggcggaggcc     180
acccgcttga acgcacggc ccgacggcgc tacacgcggc gcaagaaccg gatctgttac     240
ctacaggaga tttttctctaa cgagatggcg aaggtggacg actcgttctt tcaccgcctc    300
gaagagtcct tcctcgtgga ggaggacaag aaacacgagc gccaccccga t cttcggcaac   360
atcgtggaca aggtggccta ccacgagaag tacccgacca tctaccacct ccggaagaaa    420
ctcgtggaca gcacggacaa ggccgacctg aggctcatct acctcgccct ggcgcacatg    480
attaagttcc ggggccactt cctgatcgag ggcgacctga accggacaa cagcgacgtg     540
gacaagctgt tcatccagct agtccagacc tacaaccagc ttttcgagga aaaccccatc    600
aacgccagcg gggtggacgc gaaggcgatc ctgtccgccc ggctgagcaa gtcccggcgg    660
ctggagaacc tcatcgcgca gttgcccggc gagaagaaga cgggctgtt cgggaacctg     720
atcgccctct ccctggggct caccccgaac ttcaagtcca cttcgacct cgccgaggac     780
gccaaactac agctgagcaa ggacacctac gacgacgacc tcgacaacct gctggcccag    840
atcgggacc agtacgcaga cctgttcctc gccgccaaga acctctccga cgccatcctg    900
ctgtcggaca tcctgcgggt gaacacggag atcacgaagg cccgctctc ggcctcgatg     960
attaaacgct acgacgagca ccaccaggac ttgaccctcc tcaaggcgct ggtccgccaa    1020
cagcttccc agaagtacaa ggaaatcttt ttcgatcaga gcaagaacgg gtacgccggg    1080
tacatcgacg gcggggcgtc ccaggaggag ttctacaagt tcatcaagcc catcctggag    1140
aaaatggacg gaccgaggag gctgctcgtg aagctcaacc gcgaagattt gctccgcaag    1200
cagcgcacgt tcgacaacgg gtcgatcccc caccagatcc acctgggcga gctgcacgcg    1260
atcctcaggc gtcaggaaga cttctacccc ttcctcaagg acaaccgcga agatagag      1320
aagattctga cctttcagaat tccttattac gtgggcccgt tggctcgggg caactcgcg    1380
ttcgcctgga tgacgcgcaa gtccgaggag accatcaccc cgtggaactt cgaggaggtg    1440
gtggataagg tgcctcggc ccagtccttc atcgagcgga tgaccaactt cgacaagaac     1500
ctgccgaacg agaaggtgct ccccaagcac agcctgctct acgaatattt cacggtgtac    1560
aacggctgca cgaaggtcaa gtacgtgacc gagggaatga ggaaacctgc attcctctcc    1620
ggggagcaga agaagccat agtcgacctc ctgttcaaga ccaaccggaa ggtcaccgtc     1680
aagcagctca ggaggacta cttcaagaag atcgagtgct cgattcagt ggagatcagc      1740
ggcgtcgagg accggttcaa cgccagcctg ggcacctacc acgacctgct caagatcatc    1800
aaggacaagg acttcctcga caacgaggag aacgaggaca tcctggagga catcgtgctg    1860
accctgacgc tcttcgagga ccgcgagatg atcgaggagc gcctcaagac ctacgcccac    1920
ctgttcgacg acaaggtgat gaagcagctc aagcggcgga gatatactgg gtggggccgc    1980
ctctcccgga agctcattaa cggtatcagg gataagcagt ccgggaagac gatcctcgac    2040
ttcctcaagt cggacgggtt cgccaaccgc aacttcatgc agctcatcca cgacgactcc    2100
ctgacgttca aggaggacat ccagaaggcc caagtgtctg gtcaaggtga ctcgctccca    2160
gagcacatcg ccaacctcgc gggcagcccc gccatcaaga gggaatact ccagaccgtc     2220
aaggtggtgg acgagctggt gaaggtcatg ggccgccaca gccgagaa catcgtcatc      2280
gagatggcgc gggagaacca gaccacgcag aaggggcaga aaatagccg tgagcgcatg     2340
aagcgcatca ggaggggat taaggagttg gcagccaga tcctcaagga gcaccctgtg      2400
gagaacacgc agttgcaaaa cgagaagctc tacctgtact acctccagaa cgggagggat    2460
atgtacgtgg accaagaact ggacatcaac cgcctgtccg actacgacgt ggaccacatc    2520
gtgccgcaga gcttcctcaa ggacgacagc atcgacaaca aggtgctcac ccggtccgac    2580
aagaatcggg gcagtccga caacgtgccc agcgaggagg tcgtcaaaaa gatgaaaaac    2640
tactggcgac aactactgaa cgccaagctc atcacccagc gcaagttcga caacctcaca    2700
aaagccgagg gcgggggtt gagcgagctg gacaaggccg ggttcatcaa gcgccagctc     2760
gtcgagacgc gccagatcac gaagcacgtc gcgcagatac tcgacagccg gatgaacacc    2820
aagtacgacg agaacgacaa gctcatccgg gaggtgaagg tcatcaccct caagtcgaag    2880
ctcgtgagcg acttccgcaa ggacttccag ttctacaagg tccggagat caacaactac     2940
caccacgccc acgatgctta tcttaacgcc gtggtgggga cggccctcat taagaaatac    3000
ccgaagctgg agtcggagtt cgtgtacggg gactacaagg tgtacgacgt caggaagatg    3060
```

```
atcgccaagt ccgaacagga gatcggggaag gccacggcga atacttctt ctacagcaac     3120
atcatgaact tcttcaagac cgagatcacc ctcgccaacg gcgagatccg caagcgcccg     3180
ctcatcgaga cgaacgggga gaccggcgag atcgtctggg acaaggggcg cgacttcgcc     3240
actgtgcgga aggtgctgtc gatgcccag gtcaacatcg tcaagaagac ggaggtccga     3300
acgggcgggt tcagcaagga gagcatcctg ccgaagcgca acagcgacaa gctgatcgcc     3360
cgcaaaaagg actgggatcc aaaaaagtac ggcggcttcg acagcccac cgtcgcctac     3420
agcgtcctcg tcgtcgctaa agtcgagaag ggcaagtcca aaaagctcaa gagcgtcaag     3480
gagctgctcg ggatcaccat catggagcgg tccagcttcg agaagaaccc aattgatttc     3540
ctggaggcga agggctacaa ggaggtcaag aaagacctca tcataaagct gccgaagtac     3600
tcactcttcg agctggagaa cgggcgcaag cggatgctgg cgtcggccgg agagctccaa     3660
aagggcaacg agctggcgct gccgagcaag tacgtgaact tcctctacct ggcgtcccac     3720
tacgagaagc tcaagggcag tccagaggat aacgagcaga agcagctatt cgtggagcag     3780
cacaaagcact acctggacga gatcatcgag cagatcagcg agttctccaa gcgcgtcatc     3840
ctggcggacg ccaacctgga caaggtgctg tccgcgtaca acaagcaccg cgacaagccg     3900
atccgcgagc aagccgagaa catcatccac ctgttcaccc tcacgaacct cggggcaccc     3960
gccgccttca aatatttcga cacgaccatc gaccgcaagc gctacaccag cacgaaggag     4020
gtgctcgacg ccaccctgat ccaccagagc atcaccgggc tgtacgagac ccgcatcgac     4080
ctctcgcagc tcggcgggga c                                               4101

SEQ ID NO: 5          moltype = DNA  length = 4101
FEATURE               Location/Qualifiers
misc_feature          1..4101
                      note = Cas9 polynucleotide
source                1..4101
                      mol_type = other DNA
                      organism = synthetic construct
SEQUENCE: 5
gacaagaagt acagtattgg attggccatc gggacgaaca gcgtgggctg ggccgtcatc      60
accgacgagt acaaggtgcc atccaagaag tttaaggttc tggggaatac cgaccgccac     120
tcgatcaaga aaatctcat cggggcgctc cttttcgaca cggccgagac ggcggaagcg     180
acgcggctca gcggacggc tcgtcgccgt tacacccggc gtaagaaccg catctgttca     240
ctccaggaga tattcagcaa cgagatggcc aaggtggacg actccttttt ccaccgtctt     300
gaggagtcct tcctggtcga ggaggacaag aagcacgagc gccacccgat cttcgggaac     360
atcgtggacg aggtggccta ccacgagaag taccccacga tctaccacct ccgcaaaaaa     420
ctcgtggact caactgacaa ggccgatttg aggcttatct accctcgcct cgcccacatg     480
attaagttcc gtgggcactt cctaatcgag ggtgacctca accccgacaa ctctgacgtg     540
gacaagctgt tcatccagct tgtgcagacc tacaatcagc tctttgagga gaatccgatc     600
aacgcatctg tgtggacgc aaaggccatc ctcagcgcgc ggctgagcaa gtctaggcgg     660
ttggaaaacc tgatcgccca actgcccggc gagaagaaa atggcctctt cggcaacctg     720
atcgccctgt cgctggggct cacgccgaac ttcaagagta actttgacct ggcggaggac     780
gctaagctcc agctatctaa ggacacatac gacgacgacc tggacaacct gctggccag     840
atcggcgacc agtacgccga cctcttccta gccgccaaga acctgtccga cgccatcctc     900
ctcagcgaca tcctgcgcgt gaacacggag atcacgaagg ctccgctcag cgcctccatg     960
attaagcggt acgacgagca ccaccaagac ctaactttac tcaaagcct cgtgcggcag    1020
cagcttcccg agaagtacaa agagatattt tttgatcagt ccaagaacgg ttatgcgggc    1080
tacatcgacg gcggcgcgag ccaggaggag ttctacaagt tcatcaagcc catcctggag    1140
aagatggacg gcacggagga gctgctcgtg aagctcaacc gtgaagacct cctgcgaaag    1200
cagcgaacct tcgacaacgg ttcgatcccg caccagatcc acctcgggga gctgcacgcc    1260
atcctgaggc gacaggagga cttctaccct ttcctaaagg acaaccgcga gaagattgaa    1320
aaaatcctga cgtttcgcat accctactac gtcggcccgc tggcgcgcgg caactcccgg    1380
ttcgcttgga cccgtaa gagcgaggag acgatcaccc cgtggaactt cgaggagtc    1440
gtggacaagg cgcgagcgc gcagagcttc atcgagcgca tgaccaactt cgacaagaac    1500
ctcccgaacg agaaggtgct cccaaagcac tccctcctgt acgagtattt caccgtgtac    1560
aacgagttga caaggtgaa gtacgtgacg gagggaatgc ggaagcctgc gttcctctcg    1620
ggcgagcaga agaaggcaat cgtggacctg ctcttcaaga ccaaccggaa ggtgacggtg    1680
aagcagctca aggaggacta cttcaaaaaa atcgagtgct tcgactccgt ggagataagc    1740
ggcgtggagg accgattcaa cgcctcccte ggcacctacc acgacctcct taagatcatc    1800
aaggacaagg acttcctgga caacgaggag aacgaggaca tcctggagga catcgtgctc    1860
accctgaccc tcttcgagga ccgggagatg atcgaggagc gcctcaagac gtacgcccac    1920
ttgttcgacg acaaggtgat gaagcagctc aagcggcggc gatacaccgg gtggggccgc    1980
ctatcccgca aacttatcaa cggcatccgc gacaagcagt ccggcaagac gatcctggat    2040
ttcctcaagt cggacgggtt cgccaaccgg aacttcatgc agctcatcca cgacgacagc    2100
ctcacgttca aggaggacat ccagaaggcc aagtgagcg gtcaagggga cagcctccac    2160
gagcacattg cgaaccttgc tgggcagccct gcgatcaaga aggggatat gcaaacccgtg    2220
aaggtcgtgg acgagttgt gaaggtcatg gggcgacaca agcccgagaa catcgtgatc    2280
gagatggcca gggaaaatca gaccacgcag aagggcaaaa aaacagccg cgagcggatg    2340
aagcggatcg aggagggcat caaggagctg gggtcgcaga tcctcaagga gcacccggtg    2400
gagaacacgc agctccagaa cgagaagctg tacctctatt acctacagaa cgggcgggat    2460
atgtacgtgg accaggagct agacatcaac gcctgtcccg actacgacgt ggaccatatc    2520
gtcccgcagt cgttcttgaa ggacgacagc atcgacaaca aggtgctcac aagatcggat    2580
aagaatcgag gcaagtccga caacgtgccc tcggaggagg tggtcaagaa aatgaaaaac    2640
tactggcggc agttgctgaa cgccaagctc attacgcagc ggaagttcga caacctgacg    2700
aaggctgaac gtggtgggct cagcgagcta gacaaggcgg ggttcatcaa gcggcagctc    2760
gtcgagaccc ggcagatcac caagcacgtg gcgctcgcg catgaacacc    2820
aagtacgacg agaacgacaa gctcatccgt gaggtgaagg tcatcaccct taagtctaag    2880
ctggtcagtg acttccgcaa ggacttccag ttctacaagg tccggagat caacaactac    2940
caccacgcgc acgacgccta cctcaacgcg gtggtggga cggcgcttat taagaaatat    3000
cccaagctgg aaagcgagtt cgtttacggc gactacaagg tgtacgacgt ccgcaagatg    3060
atcgcaaagt cggaacagga aatcggaaag gcgacggcca atatttctt ttactccaac    3120
```

```
atcatgaatt tttttaagac ggagatcacc ctggcgaacg ggagatccg caagcggccc   3180
ctcatcgaga ccaacgggga gacgggcgag atcgtctggg acaagggccg ggacttcgcc   3240
accgtgcgga aggtgctttc tatgcctcaa gtcaatatcg tcaaaaagac agaggtgcag   3300
accggcgggt tcagcaagga gtctatcctg ccgaagcgca actcggacaa gctcatcgcg   3360
cgcaagaaag actgggaccc caaaaaatat ggcgggttcg actcgccgac cgtcgcctac   3420
agcgtcctcg tggtggctaa ggtcgagaag ggcaagagca aaaagctaaa gtcggtgaag   3480
gagctgctgg gcatcaccat catggagcgc tcgtctttcg agaagaatcc aatcgacttc   3540
ctagaggcga aggggtacaa ggaggtcaaa aaggatctta tcatcaaact gccgaagtac   3600
agtctgttcg agctggagaa cgggcggaag cggatgctgg ctagtgcggg cgagttgcag   3660
aagggcaacg agttggcact gcccctccaag tacgtggaact tcctgtacct ggcctcccac   3720
tacgagaagc tcaaggggag ccccgaggac aacgagcaga agcagctatt cgtcgagcag   3780
cacaagcact acctggacga gatcatcgag cagatcagtg agttctccaa gcgggtcatc   3840
ctcgcggacg ccaacctgga caaggtgctg agcgcgtaca acaagcacag ggacaagcca   3900
atcagggaac aggccgagaa catccccac ctgttcaacc tgaccaacct gggtgcacac   3960
gctgccttca gtactttga cacgaccatc gaccggaagc gctacacctc cacgaaggag   4020
gtgctggacg ccacgctgat ccaccagagc atcaccgggc tctacgagac acggatcgac   4080
ctgagccagc ttggcgggga c                                             4101

SEQ ID NO: 6             moltype = DNA   length = 4092
FEATURE                  Location/Qualifiers
misc_feature             1..4092
                         note = Cas9 polynucleotide
source                   1..4092
                         mol_type = other DNA
                         organism = synthetic construct
SEQUENCE: 6
gacaaaaagt attccattgg actcgctatc ggcacgaaca gcgtcgggtg ggcggtcatc    60
actgacgagt acaaggtgcc gagcaagaag tttaaggtgc tgggaaacac cgacaggcac   120
tcgatcaaga aaaatcttat cggggcccta ctcttcgact ccggagaaac cgccgaggcc   180
acccggttga agcgcacggc ccgccgtcgc tacaccaggc gcaagaaccg gatctgctac   240
ctccaggaga tattcagcaa tgagatggcg aaggtggacg actcgttttt tcacaggcta   300
gaggagtctt tcctcgtgga ggaggacaag aaacacgagc gccacccat cttcggcaac   360
atcgtggatg aggtggcata tcacgagaag tacccaacca tctaccacct ccgcaaaaag   420
ctcgtggact ctaccgacaa ggccgacctc cgtctgatct acctcgcgct ggccacatg    480
attaagttcc gaggacactc tctgatcgag ggcgacctga acccagacaa cagcgacgtg   540
gacaagctgt tcatccaact tgtccagacc tacaatcagc tcttcgagga aaccctatc    600
aacgcctcgg gcgtggacgc gaaggccatc ctgtccgccc gctgagcaa gtcgcggcgg   660
ctggagaacc tgatcgccca gctccccggc gaaaaaaga acggcctctt cggcaacctc   720
atcgcgttgt cgctggggct cacccgaac ttcaagtcca acttcgacct ggccgaggac   780
gctaaactcc agctctcgaa ggataccctac gacgacgacc tcgacaacct gctggccag   840
atcggcgacc agtacgcgga ccttttcctg gcgccaaga acctgagcga cgcgatcctc   900
cttagcgaca tactccgtgt gaacaccgag atcacgaagg cccgctctc cgcgtccatg   960
attaagcgct acgacgagca ccaccaagac cttacccgtc ttaaggcgct ggtcaggcag  1020
cagttaccgg agaagtacaa ggagatctttt tttgatcaat ctaagaacgg ttacgccggg  1080
tacatcgacg gcggcgcgtc ccaggaggag ttctacaagt tcatcaagcc gatcttggag  1140
aaaatggacg gaccgaggga gctgctcgtg aagctcaacc gcgaagacct cctccgcaag  1200
cagcgcacct tcgacaacgg gagcatcccg caccagatcc ctgggaga gctgcacgcg  1260
atcctgcgga gacaagagga cttctacccc ttcctcaagg acaaccggga gaagattgaa  1320
aaaatactta ctttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagtcaa aagaggacta cttcaagaag atcgagtgct tcgactccgt cgagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgtccgaaga ccgcgagatg atcgaggagc ggcttaagac gtacgcccac  1920
ctgttcgacg acaaggtgat gaagcagctg aaacgccggc gctacaccgg gtggggccgc  1980
ctctccccgca agctcatcaa cggcatccgc gacaagcagt cggggaagac gatcctgaac  2040
ttcctcaaga gcgacggctt cgccaaccga aacttcatgc agctaatcca cgacgacagc  2100
ctgacgttca aggaggacat ccagaaggcc aagtgagcg gccagggaga ctcgctacac  2160
gagcatatcg ccaacctggc tggcagcccg gcgattaaga aggaatcct ccaaaccgtc  2220
aaagtggttg acgagctggt gaaggtgatg ggccgcgaga cattgtgatc  2280
gagatggcgc gggagaacca gacgacgcag aagggccaaa aaaatagcag ggaaggatg  2340
aagcgaatag aggagggat caaggagctg ggagccaga ttctcaaga gcaccggtc    2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc gggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagt tcattaccct taaatgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggg gactacaagg tttatgacgt caggaagatg  3060
atcgccaagt cggaacagga gatcggaaaa gctaccgcca atatttctt ctatagcaac  3120
atcatgaact tcttcaaaac cgagatcacc ctcgccaacg gcgagatccg gaagcgcccg  3180
```

```
ctcatcgaga ccaacgggga gaccggggag atcgtctggg acaaggggcg ggacttcgct    3240
actgtccgaa aggtgctctc catgccacaa gtgaatatcg tcaagaaaac agaggtgcag    3300
accggagggt tcagtaagga gtccatcctg cccaagcgga actccgacaa gctaattgct    3360
cgcaaaaagg attgggatcc taaaaaatat ggcggcttcg actcgcccac ggtcgcctac    3420
tctgtgctgg tcgtgccgaa ggtggagaag ggcaagtcca agaagctcaa gagcgtcaag    3480
gagctgctgg ggatcacgat catggagcgt agttcgtttg agaagaatcc catcgacttc    3540
ctggaggcta agggctacaa ggaggtcaaa aaggacctca tcattaagct gccgaagtac    3600
agcctcttcg agctggagaa cgggcggaag cgtatgctcg cctccgctgg ggagttacaa    3660
aaggggaacg agctggcgct gccgtctaag tacgtcaact tcctgtacct ggcctcccac    3720
tacgagaagc tcaaggggtc gccggaggac aacgagcaga agcagctctt cgtagagcag    3780
cacaagcact acctggacga gatcatcgag cagatttcag agttctcaaa gcgggtcatc    3840
ctcgccgacg ccaacctgga caaggtgctc tcggcctaca caagcaccg ggacaagccg    3900
atccgcgaac aggccgaaaa catcatccac ctgttcacgc tcaccaacct cggtgccccg    3960
gcggccttca agtactttga cacgaccatc gaccggaagc gctatacctc gacgaaggag    4020
gtgctgacg ccaccctgat ccaccagtcc atcaccgggc tttacgagac ccggatcgac    4080
ctctcgcagc ta                                                       4092

SEQ ID NO: 7             moltype = DNA   length = 4101
FEATURE                  Location/Qualifiers
misc_feature             1..4101
                         note = Cas9 polynucleotide
source                   1..4101
                         mol_type = other DNA
                         organism = synthetic construct
SEQUENCE: 7
gacaagaagt atagtattgg actcgccatc ggaaccaact ctgtggggtg ggctgttatt    60
acagatgaat ataaggtgcc atccaaaaag tttaaagttc tgggcaatac tgatagacac    120
tcaatcaaga agaatctgat aggtgcactt ctgtttgata gtggagagac tgccgaggca    180
accagactta aaaggactgc aagaagaaga tataccagag aaagaatag gatttgctat    240
ttgcaggaaa tcttcagcaa cgaaatggcc aaggttgatg actcattttt ccataggttg    300
gaggagagtt ttcttgtgga ggaagataag aagcacgaaa gacacccaat tttcggaat    360
atagtggacg aggtggctta tcatgagaag tatcccacta tctaccacct gagaaagaaa    420
cttgtggact caaccgataa ggctgatctt aggcttatat acttggccct tgcacatatg    480
atcaaattca ggggccattt tcttatcgaa ggcgatctta atcccgataa ctcagatgtg    540
gacaagctgt ttatacaact tgtgcaaacc tacaatcaac tcttcgagga gaatcccatt    600
aacgcctccg gcgtgatgc aaaagccata ctgtcagcca gactgagcaa agtaggaga    660
ctggagaatc ttatagccca actgcccggt gaaagaagaa tgggctctt cggaaatctg    720
atcgctcttt cattggggtt gacacccaac tttaagagta acttgactt ggcagaagat    780
gcaaagttgc agctcagtaa agacacatat gacgatgact tgacaatct cttggcacaa    840
ataggggatc aatacgctga ccttttcctc gctgccaaga acctcagcga cgctatactg    900
ttgtccgaca ttcttagggt taataccgaa attacaaagg cccctcttag tgcaagtatg    960
atcaaaaggt atgatgagca tcaccaagac cttacactgc tgaaggctct ggttagacag   1020
caactccctg aaaagtataa ggaaatattc ttcgaccaaa gtaagaacgg gtacgccggt   1080
tatattgatg ggggcgcaag tcaagaagaa ttttacaaat tcatcaagcc aattcttgaa   1140
aagatggacg gaactgagga attgctggtg aaactgaata gagggacct tcttagaaaa   1200
cagaggacat ttgacaatgg gtccatccca caccagattc atctggggga actccacgca   1260
atattgagga gacaagaaga cttttaccca tccttactga ataatagaa gaaaatcgaa   1320
aaaatcctga ctttcaggat tccttactat gttgggccac tggccagggg gaactcaaga   1380
ttcgcttgga tgacaaggaa gtcagaagaa accataaccc cttggaattt tgaagaggtg   1440
gttgataagg gggcatcagc ccagtctttc atagagagga tgaccaactt tgataaaaat   1500
cttccaaatg agaaggtttt gccaaaaaca gtgtttttgt acgagtactt tactgtttat   1560
aacgaattga ccaaggtgaa gtatgtgacc gagggaatga ggaagccagc atttttgtcc   1620
ggggagcaaa agaaagcaat cgttgatctt ctcttcaaga ccaacagaaa agtgaccgtg   1680
aaacaactga aggaagacta cttcaaaaag atagaatgtt tcgattcagt ggaaattagc   1740
ggtgttgaag acaggttcaa tgcttcattg ggtacttacc acgacctgtt gaagataatc   1800
aaagacaagg actttctcga taatgaggag aacgaagaca tcttggaaga cattgtgctt   1860
acactcactt tgtttgagga cagggaaatg attgaggaaa gactcaaaac ttacgctcat   1920
ttgtttgatg ataaggttat gaaacaacta aaaagaagaa ggtacaccgg ctggggaaga   1980
ttgagtagga aactgatcaa cggtattaga gataaacaat ccggaaaagc tatcctcgat   2040
ttccttaaga gtgatggctt tgcaaatagg aattttatgc agctgattca tgacgactca   2100
cttaccttca aagaagacat ccaaaaagct caggtgtctg gcaaggcga cagtctgcat   2160
gaacatatag ctaacttggc tgggagtccc gccatcaaga ggggatact caaacagtt   2220
aaagttgtgg acgaattggt gaaggtaatg ggaaggcaca gcctgaaaa tatagtgata   2280
gaaatggcaa gggaaatca aacaacccag aagggacaga agaacagtag ggaaagggt   2340
aaaaggatag aagaggggat caaagagctt ggtagccaga tcctcaagga acatccagtg   2400
gagaataccc aacttcaaaa cgagaaactc tatttgtact acttgcagaa cggaagagat   2460
atgtatgtgg accaagagct tgatattaac aggctgagcg attatgacgt tgaccacata   2520
gtgccccaat cattcctcaa ggatgactct attgataata aggtgctgac aagagtgac   2580
aagaatagag gaaatagccg caacgttcca tccgaggaga ttgtgaagaa gatgaagaac   2640
tactggaggc agttgctgaa cgctaagctc attcccagag gaaattcga aacctgacc   2700
aaagcagaga gaggcgggct gagcgaactc gataaagcag gttcatcaa gagacaactc   2760
gtggagacta ggcaaattac taagcacgtg gctcaaatac tcgacagcag gatgaacaca   2820
aagtacgacg agaacgacaa gctcattaga gaggttaagg ttattactct gaaaagtaaa   2880
ttggtaggcg attttcagaa ggatttccaa ttctataagg ttagagagat caacaattat   2940
catcatgcac atgatgccta tctgaatgct gtggttggta cagcccttat caagaagtac   3000
cctaagctag agagcgagtt tgtgtacgga gattataagg tgtatgatgt gagaaaatg   3060
atcgctaaaa gtgagcaaga gattggaaag gctaccgcca atacttctt ttattccaat   3120
attatgaatt tcttcaagac agaaatcacc ctggctaacg gcgagataag gaagaggccg   3180
cttatcgaaa ctaatgggga gacaggcgaa atagtgtggg acaaagggag ggatttcgca   3240
```

```
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggaccta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact ttttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacagg gataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                             4101

SEQ ID NO: 8        moltype = DNA   length = 4101
FEATURE             Location/Qualifiers
misc_feature        1..4101
                    note = Cas9 polynucleotide
source              1..4101
                    mol_type = other DNA
                    organism = synthetic construct
SEQUENCE: 8
gacaaaaagt attccatcgg gcttgctatc ggaaccaact ctgtggggtg ggcagttatt   60
accgacgaat acaaggtgcc cagcaagaag tttaaggttc tggggaacac agatagacat  120
agcataaaga aaacctgat aggcgcactg ttgttcgact ccggggaaac agccgaagct  180
accaggctga agagaactgc aagaagaagg tacaccagaa gaaaaacag aatatgttat  240
ctccaagaga ttttctctaa cgagatggcc aaggtgacg actcattctt tcacagactg  300
gaagaatctt tccttgtgga agaagataag aaacacgga ggcaccctac ttttggcaat  360
atcgtggatg aggtggctta ccacgaaaaa tacctacaa taaccacct caggaaaaaa  420
ttggttgata gtcagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact acaatcagt tgtttgagga aaacccatt  600
aatgcttccg ggtggacgc caaggcaatc ctttctgca gactctcaaa gtcaaggaga  660
ctcgaaaatc tgatagcaca gcttccagga gagaagaaga cgggctctt tggaaacctg  720
atcgctctgt cactcggact cacacccaat ttcaaaagca attttgatt ggcagaggac  780
gctaagctgc aactcagtaa ggatacctac gacgatgact ggataatct gctcgcacaa  840
attggggacc agtatgcaga cctgttttct gcagctaaga acttgagtga cgccatattg  900
ctcagtgaca tcctcaggggt taataccgag attacaaaag ctccactctc tgcaagcatg  960
atcaagaggt atgacgagca ccatcaagac ctgacactcc ttaaggcgtt ggttaggcag 1020
caacttcctg aaaagtataa ggaaatcttc ttcgatcaaa gcaaaaacgg ctacgccggc 1080
tatatagacg ggggagcatc ccaagaagaa tttttataagt tcataaaacc tatattggag 1140
aagatggacg ggacagagga attgctcgtg aaactgaaca gggaggatct cctcaggaag 1200
caaaggacct tcgacaatgg ctccatccca atcagattcc cctcggcga actgcacgca 1260
atactgagaa gacaagagga ctttatcct ttcctgaagg acaacagga gaaatcgag 1320
aaaatcttga cattcagaat cccatactac gtttgggcct tggccagaga taacagtagg 1380
ttcgcctgga tgactaggaa atcagaggag actattacac cctggaactt gaagaagtt 1440
gttgataagg gagcttcagc acaatcattc atcgaaagaa tgacaaactt tgacaaaaat 1500
ctgcctaatg agaaagtgct cccaaaacat tccctgctgt atgagtattt taccgtttat 1560
aacgagctta ccaaggtgaa atacgttact gaaggtgaa aaagccaatt ttttctttca 1620
ggggagcaaa agaaggctat cgtggatctt ctctttaaga ccaacagaaa ggttaccgtg 1680
aagcagctta aggaagacta ctttaaaaag atcgagtgtt ttgactcagt ggaaataagc 1740
ggtgttgaag atagattcaa cgcatccttg ggaacttatc atgatcttct taagataatc 1800
aaggataaag actttctcga caacgaggaa aacgaagata tactgaggaa catagttctg 1860
acacttactt tgttcgagga taggagaatg atcgaggaa gactgaaaac atatgctcac 1920
cttttcgacg acaaagttat gaaacaactc aagagaagga gatatacagg gtgggggaga 1980
ttgagcagga aactgattaa tggtatcaga gacaaacagt caggaaaaac aatactcgac 2040
tttttgaaat cagacgggtt cgcaaatagg aattcatgc agcttataca cgacgattca 2100
cttacttta aagaggacat tcaaaaggct caagttagtg acaaggtga ctccctccca 2160
gaacacatcg caaatctcgc tggcagccct gcaattaaga agggtatact ccagacagtt 2220
aaggttgttg acgagctggt taagtgatg ggaagacaca aacccgagaa catagtgata 2280
gagatggcca gggaaaacca aaccactcaa aaaggcaga aaattccag agagaggatg 2340
aaaaggattg agaaggtat caaggagctg ggtagcagaa ttctgaaaga acatcctgtg 2400
gaaacactc aactccagaa tgagaaactc tatctgtact atctgcaaaa tgggagagat 2460
atgtatgtgg accaggaact ggacataaac aggctctcag attacgatgt ggatcatatc 2520
gtgccacagt ccttcttaa ggatgatagc atcgacaata aggtgcttac caggtccgac 2580
aagaacaggg gaaagtcaga taacgtgcct tctgaagag ttgttaaaaa gatgaagaac 2640
tactggagac agctgcttaa cgctaagctc ataacacaga gaaagtttga caacttgacc 2700
aaggccgaga gaggcggact tcagaattg gataagcag ggttcataaa aagcagctg 2760
gtggaaacaa ggcagataac taaacatgtg ctcagatcc tcgatagtag gatgaataca 2820
aaatacgatg agaacgacaa gctcataagg gaggttaag tgataactct gaaatccaaa 2880
ctggttagcg attttaggaa ggatttccag ttttacaaag ttagggagat caacaattat 2940
catcacgcc acgatgccta cttgaacgca gttgtgggta cagcacttat caaaaagtac 3000
cctaagctgg aatccgagtt tgtttatgga gactataagg tgtacgacgt tagaaaatg 3060
attgcaaagt cagagcagga ataagggaaa gccactgcaa aatatttctt ttatagcaat 3120
atcatgaatt tctttaagac agaaatcaca ctggccaatg ggaaataag gaagaggccc 3180
ctgatcgaaa ctaatggcga gacagggggag attgtgtggg ataaaggtag ggactttgca 3240
acagtgagga aagtgctgag catgccccaa gttaatatcg ttaaaaagac cgaggttcaa 3300
```

```
acaggggct ttagtaagga aagcattttg cccaagagga atagtgacaa attgattgct 3360
aggaaaaaag attgggaccc caaaaagtat ggcggatttg atagccccac tgttgcttac 3420
tccgtgctcg tggttgcaaa ggtgagaag ggaaagagca agaaactgaa gtcagttaag 3480
gaactccttg gtatcactat catggaaga agctcctttg agaagaaccc tattgacttc 3540
ctggaggcta aagggtacaa agaggttaag aaagaccta tcattaaatt gcccaaatat 3600
agtcttttcg agcttgaaaa cggaagaaag aggatgcttg catccgctgg cgaattgcaa 3660
aagggcaatg agcttgctct cccttccaag tatgtgaact tcctttatct tgcctcacac 3720
tatgaaaaac tcaaaggttc acccgaagac aacgaacaaa agcaactatt tgtggaacaa 3780
cacaagcact acctggacga aatcattgag caaatttctg agttttcaaa aagggtaatc 3840
ttggctgacg caaatctcga caaagttttg tcagcttaca acaaacatag agataagcca 3900
attagagagc aagctgagaa tatcatccat ctgtttaccc tgactaacct tggagcgcct 3960
gctgctttta aatatttcga caccacaatc gacaggaaga ggtacactag cactaaggaa 4020
gttctcgacg ccaccctcat ccaccagagt attacaggcc tgtacgagac aagaattgat 4080
cttctctcaac ttggtggtga c                                         4101

SEQ ID NO: 9               moltype = DNA  length = 4101
FEATURE                    Location/Qualifiers
misc_feature               1..4101
                           note = Cas9 polynucleotide
source                     1..4101
                           mol_type = other DNA
                           organism = synthetic construct
SEQUENCE: 9
gataagaagt actcaatcgg tctggcaatc ggaaccaact ctgtgggttg ggcagtgatt   60
acagatgagt ataaggtgcc aagcaaaaaa ttcaaggtgc tgggtaatac cgacagacac  120
agcattaaga agaattttga tggagcactc tctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct tcttgttga agaggacaaa aagcatgaaa ggcatccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga tccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggccag  840
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagcccct cgttagacag 1020
cagttgccag aaaagtacaa agaaatattc tttgatcaat caaaaaacgg atatgcaggg 1080
tacatcgacg gtggggcaag ccaggaagag ttctacaaat tcatcaaacc tatcctggaa 1140
aagatggatg gacagaaga gctgctggtt aagctaaact cctcagaaag 1200
cagaggacat tgataacgg agcatccct catcaaatcc acctcggtga actccatgct 1260
atcctgagaa ggcaggaaga cttttatcca tttttgaagg acaatagga gaaaatcgaa 1320
aaaatcctga cattcagaat cccatactac gttggtcctc tggcaagagg taacagtagg 1380
ttcgcatgga tgcaaggaa aagcgaggag acaatccgac cctggaattt tgaggaagtt 1440
gttgacaagg gtgccagcgc acaatccttt atcgaaagaa tgacaaattt cgacaagaat 1500
ctgcctaacg aaaaggttct cccaaagcat tcactcctgt acgaatattt tacagtttat 1560
aacgaactga ctaaagttaa atacgttacc gagggtatga ggaagccagc attcctttcc 1620
ggggaacaga agaaagctat tgtggacctc ctgttcaaa caaatagaaa agtgacagtt 1680
aagcaactca agaggatta cttcaaaaag atcgaatgtt ttgactctgt ggagatcagc 1740
ggggtggagg atagattcaa cgccagcctg gtacatatc atgatctcct gaaaatcatt 1800
aaagacaagg acttccttga caacgaggag aacgaggaca ttctggaaga cattgttctg 1860
acccctcacac tcttttgagga tagggatatg attgaggaaa gactgaagac ctacgcccaa 1920
ctctttgacg ataaagtgat gaaacagctc aagagaagaa ggtatacagg ttggggagga 1980
ctgagcagga agttgatcaa tgggattagg gacaaacagt ccgggaaaac aatcctcgat 2040
tttctgaagt cagacggttt cgcaaacaga attttatgc agctcattca cgatgacagc 2100
ttgacattca aggaagacat ccaaaaggct caagtgagcg gccaagggga tagcctccac 2160
gagcatattg caaatctggc aggttcacca gccatcaaaa agggcatact tcagacagtt 2220
aaggttgtgg acgaattggt taagttatg ggcaggcata agccagaaa tatcgttatc 2280
gaaatggcaa gggagaacca aacaactcaa aaagggcaga aaatagcag agagaggatg 2340
aaaagaatcg aggaagggat caaggaactt gggtcccaaa tcctcaagga gcacccagtt 2400
gaaaatactc aactgcaaaa cgagaagctc tatctctact atctccaaaa cgggagggat 2460
atgtatgttg accaggagct ggatattaac agactgtcag attatgatgt tgatcatatc 2520
gtgccccagt cattcctgaa ggacgattcc atcgacaaca agttctcac aaggtccgat 2580
aaaaacaggg gcagtccgga taacgttcca agcgaagaag tggtgaaaaa gatgaaaaac 2640
tattggagac aacttctgaa tgcaaagttg attactcaga gaaagtttga caacctcaca 2700
aaagcagaaa gaggcgggct tagcgaactc gataaggcag ggtttatcaa aagacagctg 2760
gttgagacaa ggcagatcac aaaacatgtg gcacagatcc ttgactcaag gatgaatacc 2820
aagtatgatg agaatgataa gttgatcagg gaggttaaag ttatcacact caatccaaa 2880
ctggtgtcag acttcaggaa agactttcaa ttttataagg tgagggagat caataactac 2940
caccatgcac atgacgccta cctgaacgca gtggtgggta cagcattgat taaaaatac 3000
cctaaggag agtctgagtt tgtgtacggg gactacaagg tgtacgacgt gaggaaaatg 3060
atagccaagt ccgagcagga gatcgggaaa gcaacagcta gtatttctt ttacagtaat 3120
atcatgaatt tcttttaaaac tgagattact ctggcaaacg gggagatcag gaaaagaccc 3180
ctcatcgaga ctaatggtga aacaggtgag atcgtttggg acaaggggag ggattttgct 3240
actgttagaa aagttctgag tatgccacaa gtgaatattg tgaaaagac agaagttcag 3300
acaggtgggt tctccaaaga atccatcctg cccaagagaa attcagacaa gctcatcgca 3360
```

```
agaaagaagg actgggaccc taagaagtac ggaggatttg acagccccac cgtggcctat    3420
tccgtgcttg ttgtggcaaa ggtggagaaa gggaagagca aaaaactgaa atccgtgaaa    3480
gaactgctgg gaattaccat catggaaaga agctcctttg agaagaaccc aatcgacttc    3540
ctggaagcaa aaggatataa ggaagtgaaa aaggacctca ttatcaagct cccaaaatac    3600
tcacttttcg agttggagaa cggtagaaag aggatgctgg caagcgcagg ggaacttcag    3660
aaaggcaatg agctggcatt gccatcaaag tatgtgaact tcctctactt ggccagccat    3720
tacgagaaac ttaaaggtag cccagaagat aacgagcaaa aacagctctt tgtggaacag    3780
cataagcatt atctggatga gatcatagaa caaatctcag agttttccaa gagagttatc    3840
ctcgcagatg caaacctgga taaggttctc tcagcctata ataagcatag agacaagcca    3900
attagagagc aagcagagaa cattatccac ttgttcactc ttacaaacct ggggcacca     3960
gccgccttca aatatttcga tacaacaata gacagaaaga ggtataccag caccaaagaa    4020
gttctcgacg ccacactgat ccatcaatca atcacaggcc tttacgaaac taggatcgac    4080
ttgtcacaac tgggtgggga t                                              4101

SEQ ID NO: 10           moltype = DNA   length = 3307
FEATURE                 Location/Qualifiers
misc_feature            1..3307
                        note = Cas9 polynucleotide
source                  1..3307
                        mol_type = other DNA
                        organism = synthetic construct
SEQUENCE: 10
gagcaaggac acctacgacg acgacttgga caacctattg gcccagatag gtgaccagta      60
tgcagacctc ttccttgcgg ccaagaactt gagtgacgct atactgctca gtgacatcct     120
gagggtgaac actgagatca ctaaggcccc tctctctgcc tcaatgatta agcgttacga     180
cgagcatcac caggatctca ccctgcttaa ggcccttgct cggcagcagc tccctgagaa     240
gtacaaggag atattttttg accagtctaa gaacggctac gccggttaca ttgacggtga     300
ggcaagccag gaggagttct acaagttcat caagccgatc cttgagaaga tggacggcac     360
cgaggagcta cttgtcaagt tgaacccgga agacctgctc cggaaacagc gtacattcga     420
caacgcgcag atccctcacc agatccacct gggcgaacta cacgccatcc tccgacgtca     480
ggaggacttc tatccattct tgaaagataa cagggaaaaa atcgaaaaaa tacttacgtt     540
tcgaataccct tactacgtgg ggccccttgc tcggggaaac tccagattcg catggatgac     600
caggaagtca gaggagacca tcacaccctg aactttgag gaggtggttg acaaaggtgc     660
ttctgcccag tccttcattg agcggatgac taacttcgac aagaacctgc ccaacgagaa     720
ggtgctgcca aagcacagcc tgctctacga atactttact gtgtacaatg agctgacgaa     780
ggtgaagtac gtgacagagg ggatgcggaa gcccgctttc ctgagcggcg agcaaaaaaa     840
agcaatcgtg gacctactgt tcaagaccaa ccgaaaggtg acagtgaagc agctcaagga     900
ggactacttc aaaaaaatcg agtgcttcga ctctgttgag ataagcggcg tggaggaccg     960
attcaacgtc tcattgggaa cctatcacga cctgctcaaa atcattaagg acaaggactt    1020
cctggataat gaggagaatg aggacatcct ggaggatatt gtgctgaccc ttactctatt    1080
cgaggacagg gagatgatcg aggagcgact caagacctac gctcacctgt tcgacgacaa    1140
ggttatgaag caattgaagc gtaggcgata cacggggtgg ggaagactct cccgaaaact    1200
gataaacgaa atcaggagaca agcagtcagg gaagacagc ttggacttcg tgaaatccga    1260
cgggttcgcc aaccgcaact tcatgcagct cattcacgac gactcactaa cgttcaaaga    1320
ggacattcag aaggctcaag tcagtggaca aggcgactcc ctgcacgagc acattgcaaa    1380
ccttgcgggc tccccggcga ttaaaaaggg cattctccaa acgttaagg tggtggacga    1440
gctggtgaag gtgatgggcc gacacaagcc tgagaacatc gtgatcgaga tggcccaggga    1500
gaaccagact acccagaagg gtcagaagaa ctctcgggaa cgtatgaagc gtattggagga    1560
ggggattaag gagtggggct ctcaaatcct caaggagcac cctgtggaga cactcagct     1620
ccaaaacgag aagctgtacc tgtactacct gcaaaacggg cgcgatatgt acgtggatca    1680
ggagttggac atcaacaggc ttagcgatta cgacgtcgac cacatcgtgc cacagtcatt    1740
cttaaaggac gacagcatcg acaacaaggt tctgacgagg agcgacaaga atcgagggaa    1800
aagtgacaat gttccatccg aggaggtggt caagaaaatg aagaactatt ggcgtcagct    1860
tctgaacgcc aagctcatca cccagcggaa attgacaac ctgactaagg ctgagcgagg    1920
cggactctcc gagcttgaca aggctggctt catcaagcgg cagttggtcg aaacccgaca    1980
gataacgaag cacgttgccc agatacttga ctcccgtatg aacaccagt acgacgagaa    2040
cgacaagctc atcagggagg tgaaggtcat taccctaag tccaaactcg tcagcgactt    2100
tcgtaaggac ttcagttct acaaggtgcg cgagatcaat aactaccacc acgcacacga    2160
cgcctacctg aacgcagtgg ttgaaccgc gttgattaaa aagtaccca gttggagtc     2220
ggagttcgtt tacgggact acaaggtgta cgacgttcgg aagatgatcg ccaagtctga    2280
acaggagatc gggaaagcaa ccgccaagta tttttcctat agcaacatca tgaacttctt    2340
taaaaccgag atcacacttg ccaatggcga gatccgtaag aggccgctga tcgagacaaa    2400
tggggagact ggcgagatcg tgtgggacaa gggccgcgac ttcgcaaccg ttcggaaagt    2460
cttgtccatg cctcaagtca acatcgtcaa gaagactgag gtcaaacag gcgggtccc    2520
gaaggagtcc atactgccca gaggaactc gacaagctc atagcacgca aaaaagactg    2580
ggatccaaag aaatacggcg ggttcgactc gccgacagtc gcatactccg tgttagtggt    2640
ggctaaagtg gaaaaggga agtccaagaa gctcaagtcc gtcaaggagt tgctcggat     2700
caccattatg gaacggtcct cattcgagaa gaatccccatt gacttcctag aggcgaaggg    2760
ctacaagagg gtcaaaaagg acctaattat taagctcccc aagtattcac tcttcgaact    2820
tgaaaatggt cgtaagcgga tgttggcaag cgctggagag cttcagaagg ggaacgagct    2880
tgcactgcct tccaagtacg tgaacttcct gtacctcgcc tctcattacg agaagttgaa    2940
gggctcaccg gaggacaacg agcagaagca gttgttcgtg gagcagcaca gcactacct     3000
cgacgagatc attgagcaga taagtgagtt cagcaaacgg gtgatccttg ccgacgctaa    3060
cctggacaag gtgctgagcg cctacaacaa gcacagagac aagcccatcc gagagcaagc    3120
ggagaacatc atacacctgt tcaccctcac gaacctcggg gctccgcag ccttcaaata    3180
ttttgacacg accatcgacc gtaaacgcta cactagcacg aaggaggtgc tggacgctac    3240
ccttatccac cagtccatca ccggcctgta cgagacgaga tcgacttgt cgcagctcgg    3300
tggtgac                                                              3307
```

| SEQ ID NO: 11 | moltype = DNA length = 4101 |
|---|---|
| FEATURE | Location/Qualifiers |
| misc_feature | 1..4101 |
| | note = Cas9 polynucleotide |
| source | 1..4101 |
| | mol_type = other DNA |
| | organism = synthetic construct |

SEQUENCE: 11

```
gacaaaaaat actcaattgg tctggcaatt gggaccaaca gtgtcggatg ggccgtgatt    60
accgacgagt acaaggtgcc gtccaaaaaa ttcaaggtgc ttgggaacac cgaccgccac   120
tcgatcaaga aaaacctaat cggtgcgttg cttttcgaca gtggggagac cgccgaggca   180
acacgcttaa aacgcacagc taggaggaga tatacacggc gcaagaaccg aatatgctac   240
ttacaggaga tattctccaa tgagatggcg aaggtggacg actctttctt ccatcggctt   300
gaggaatcct tcctggtcga ggaggacaag aagcacgagc gacacccgat attcgggaac   360
atcgttgatg aggtggcgta ccacgagaag tacccaacga tataccactt acgcaagaag   420
ctcgtggact ctacggacaa ggccgacttg cgccttatct acttggcact ggcccacatg   480
attaagttcc gaggccactt cctttcgag ggtgacctga ccccgataa ctccgacgtg   540
gacaagctct tcatccaact cgtccagaca tacaaccagc tattcgagga gaatcctatc   600
aacgcctctg gggtggacgc taaagctatc ctctcagccc gcctgtcaaa gtcgaggagg   660
ttggagaacc taatcgccca gcttccaggc gagaagaaaa atgggctgtt cggaaacctt   720
atcgcactct cactgggcct aaccccgaac ttcaagtcca acttcgacct ggcagaggac   780
gcgaaattgc agttgtcgaa agacacctat gacgatgacc tggacaacct gttggcccac   840
ataggggacc agtacgccga cctgttccta gcggccaaga acctgtccga cgccatcttg   900
ctgtcggata tactgcgggt gaacaccgag atcactaaag cacctctctc cgccagcatg   960
attaagcgtt acgacgagca ccaccaagat ttgaccctgc taaaggcact tgtacggcag  1020
cagcttcccg agaagtacaa ggagatcttt tcgaccaaca gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgga gaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
aacgagctta ctaaagttaa gtatgttact gagggcatga gaaaccgc cttcctgtca  1620
ggcgagcaga agaaagctat tgtgaccctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg ggcgacaca gcccgagaa catcgtgatc  2280
gagatggcca gggagaacca gaccacccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtgaagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggaa ccgcgcttat taaaaagtac  3000
cctaagttgg agtcagagtt cgtttatggg gactacaagg tgtacgacgt ccggaagatg  3060
attgcaaagt ctgaacagga atcggggag gccaccgcca aatatttctt ctacagtaac  3120
attatgaatt ttttttaagac tgaaattact ctcgcaaacg gcgagatcag gaagcgtccc  3180
ctcatcgaga caaacgggga gaccggggag atagtctggg acaagggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgcaagc aggctgagaa catcatccac cttttcactc ttacaaacct cggtgctccc  3960
gccgccttca atacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcggga t                                            4101
```

| SEQ ID NO: 12 | moltype = DNA length = 5499 |
|---|---|

| FEATURE | Location/Qualifiers |
|---|---|
| misc_feature | 1..5499 |
| | note = base editor |
| source | 1..5499 |
| | mol_type = other DNA |
| | organism = synthetic construct |

SEQUENCE: 12

```
ggttcgaaga agagaagaat taaacaagat tcttcggaga caggcccgt tgccgttgac    60
cccacgctgc ggaggcggat tgagccccac gagttcgagg ttttcttcga cccaagggag   120
ctgaggaaag agacatgcct cctctacgag atcaactggg gcgggcggca cagcatctgg   180
aggcatacct cgcagaacac caacaagcat gtggaggtta atttcattga gaagttcaca   240
actgagaggt acttctgccc caacactagg tgctcgatta cttggttcct gagctggagc   300
ccatgcgggg agtgcagccg cgcgatcaca gagttcctgt cccgctaccc ccacgtgacg   360
ctcttcatct acattgcccg gctgtaccat catgccgatc cacggaatag gcaggggctg   420
cgggatctga tcagcagcgg ggtgacgatt cagatcatga ccgagcagga gtcggggtac   480
tgctggcgga acttcgtgaa ttactccccc tccaacgagg cgcactggcc caggtatcca   540
catctctggg tccggctgta tgtgctggag ctgtactgca tcatcctcgg cctgccccca   600
tgcctcaaca tcctcaggcg gaagcagccc cagctgacgt tcttcacgat cgctctgcaa   660
tcgtgccact accagaggct gccccctcat atcctctggg ctaccggcct caagtcggga   720
ggctcttccg gcgggagcag cggctcggaa acgccaggta cctcggagtc ggctacacca   780
gagagttccg gcgggtccag cggggcagc gacaagaagt acagcatcgg gctggcgatc   840
gggaccaact ccgtcggctg ggctgtgatt accgacgagt acaaggtgcc atccaagaag   900
ttcaaggtcc tcgcaacac tgaccggcac agcattaaga agaacctgat tggggcgctg   960
ctgttcgatt cggggagac tgcggaggcg accaggctga gcggactgc gcgccggagg   1020
tacaccagga ggaagaatcg gatctgctac ctccaggaga tttttctcgaa tgagatggcc  1080
aaggtggaga attccttctt ccatcgcctg gaggagtcgt tcctcgttga ggagacaag   1140
aagcatgaga ggcatcccat tttcgggaat atcgttgacg aggtggctta ccatgagaag  1200
tacccgacca tctaccatct gcggaagaag ctcgtcgatt cgaccgataa ggccgacctg  1260
cggctgatct acctggccct cgcgcacatg attaagttcc ggggcatttt cctcatcgag  1320
ggcgacctca acccggacaa ctcggacgtg gataagctct tcattcagct cgtgcagaca  1380
tacaaccagc tcttcgagga gaatcccatt aacgcctcgg gggtcgacgc taaggctatt  1440
ctctcggctc ggctgtcgaa gtcgcgccgg ctggagaatc tcattgccca gctcccaggc  1500
gagaagaaga acgcctcttc ggcaacctga ttgccctgt cgctgggggct cacaccgaat  1560
ttcaagtcga acttcgacct cgccgaggac gctaagctcc agctcagcaa ggatacttac  1620
gatgatgacc tcgataacct gctccgccag attgggatc agtacgcgga tctgttcctc  1680
gcggccaaga atctcagcga tgctattctc ctgtcggaca ttctccgcgt caacacagag  1740
attactaagg ccccactgtc ggcgagcatg attaagaggt acgatgagca tcatcaggac  1800
ctgacactgc tcaaggcgct ggtccggcag cagctccccg agaagtacaa ggagattttc  1860
ttcgatcagt caaagaatgg gtacgcgggc tacattgatg gcggcgcgtc ccaggaggag  1920
ttctacaagt tcattaagcc catcctggag aagatggacg gaccggagag gctgctggtg  1980
aagctcaatc gggaggacct gctccggaag cagcgcacat cgacaatgg ctcgattcct  2040
caccagatte acctgggcga gctgcacgcc attctccgca ggcaggagga cttctacccg  2100
ttcctcaagg acaaccgcga gaagatcgaa aagatcctga ccttccgaat tccatactac  2160
gtggggccgc tcgcgcgggg gaactcccgg ttcgcgtgga tgactcgcaa gtccgaagaa  2220
acgattacac cgtggaattt cgaggaggtc gtcgacaagg cgctagtgc gcagtcattc  2280
attgagagga tgaccaattt cgataagaac ctgcctaacg agaaggtgct gccgaagcat  2340
tcgctgctct acgagtactt caccgtttac aatgagctga ccaaggtgaa gtatgtgact  2400
gagggcatga ggaagccagc gttcctgagc ggcgagcaga agaaggctat cgtggacctg  2460
ctcttcaaga ctaaccggaa ggtgactgtg aagcagctca aggaggacta cttcaagaag  2520
attgagtgct cgattccgt tgagattagc ggggtgagg atcggttcaa tgcttcgctc  2580
gggacatcac acgatctcct gaagatcatt aaggataagg acttcctcga caacgaggag  2640
aacgaggaca ttctcgaaga tattgtcctg accctcaccc tcttcgagga tcgggagatg  2700
atcgaggaga ggctcaagac atacgctcat ctgttcgatg ataagtcat gaagcagctg  2760
aagcgcaggc ggtacacagg gtggggggg ctgagccgga agctgatcaa cgggattcgg  2820
gataagcagt ccgggaagac aatctctgac ttcctcaaga ccgacgggtt cgctaaccga  2880
aacttcatgc agctcattca tgatgactcg ctgacattca aggaggatat tcagaaggcc  2940
caggtttcgg ggcagggcga ctcgctccac gagcatattg cgaatctggc ggggctcccc  3000
gcgattaaga gggcattct gcaaaccgtc aagtggttg atgagctggt caaggtcatg  3060
gggcggcata agccagagaa tattgtcatc gagatggcgc gggagaatca gaccacacag  3120
aaggggcaga agaactcacg ggagcggatg aagcgcatcg agagggcat caaggagctg  3180
gggtcgcaga tcctgaagga gcatcccgtg gagaacactc agctgcaaaa tgagaagctg  3240
tacctctact acctccagaa cgggagggac atgtatgtgg atcaggagct ggatattaat  3300
aggctgagcg attacgatgt cgaccacatt gtcccacagt cgttcctgaa ggacgacagc  3360
attgacaaca aggtgctgac ccgctcggat aagaacaggg gcaagagtga taatgttcca  3420
agcgaggagg ttgtgaagaa gatgaagaac tactggcgg agctcctgaa cgcgaagctc  3480
atcacacagc ggaagttcga caacctcacc aaggctgagc gcggggggcct gagcgagctg  3540
gacaaggcgg ggttcattaa gaggcagctg gtcgagacac ggcagattac aaagcatgtt  3600
gcgcagattc tcgattcccg gatgaacacc aagtacgatg agaacgataa gctgattcgg  3660
gaggtcaagg taattaccct gaagtccaag ctggtgtcgg acttccggaa gacttccaa  3720
ttctacaagt tcggagat caacaactac caccacgcgc atgatgccta cctcaacgcg  3780
gtcgtgggaa ccgctctcat caagaagtac ccaaagctgg agtcagagtt cgtctacggg  3840
gattacaagg tttacgacgt gcggaagatg atcgctaaga gcgagcagga gattggcaag  3900
gctaccgcta agtacttctt ctactccaac atcatgaact tctcaagac agagattacc  3960
ctcgcaatg gcgagatccg gaagaggccc ctcatcgaaa caatgggaaa gacaggggag  4020
attgtctggg ataaggggcg ggattcgcg accgtccgga aggtcctgtc gatgcccag   4080
gttaatattg tcaagaagac tgaggtccag actggcggct tctcaaagga gtcgattctc  4140
ccaaagagga actccgataa gctcattgct cggaagaagg attgggaccc caagaagtac  4200
ggggggattcg actcccccac tgttgcttac tctgttctgt tgttgctaa ggtggagaag  4260
gggaagtcga gaagctgaa gagcgtgaag gagctgctcc ggattacaat tatggagagg  4320
```

```
tcatccttcg agaagaatcc catcgacttc ctggaggcca agggctacaa ggaggtgaag    4380
aaggacctga ttattaagct gcccaagtac tcgctcttcg agctggagaa tgggcggaag    4440
cggatgctgg cgtccgcggg ggagctgcaa aaggggaacg agctggcgct ccctccaag    4500
tatgtgaact tcctctacct ggcgtcgcac tacgagaagc tgaaggggtc cccagaggat    4560
aatgcagcaa agcagctctt cgtcgagcag cataagcgac acctggacga gattatcgag    4620
cagattagcg agttctcgaa gcgggtcatc ctcgcggatg cgaacctgga taaggtgctc    4680
agcgcctaca ataagcaccg ggacaagccg attcgggagc aggcggagaa tattattcac    4740
ctcttcacac tcaccaacct cggggcacca gctgcgttca agtacttcga cactactatc    4800
gaccggaagc ggtacacctc gacgaaggag gtgctcgacg ccaccctcat tcaccagtcg    4860
atcacaggcc tgtacgagac acggattgac ctgtcccagc tcgggggcga cagcggcggg    4920
tcgggcgggt cgggcggctc aaccaacctg tcggatatta ttgagaagga gacaggcaag    4980
cagctggtta tcaggagtc gatcctgatg ctcccggagg aggtgaagga ggtcatcggg    5040
aacaagccag agtcggatat tctcgtgcac accgcgtacg acgagtcgac agacgagaac    5100
gttatgctgc tcacatcgga cgcgccagag tacaagcct ggcgctggt aattcaggat    5160
tcaaatggcg agaacaagat caagatgctg tccggggga gcggcggtc cggggctcg    5220
accaacctct ccgatataat tgagaaggaa accggcaagc agctcgttat tcaggagtcg    5280
attctgatgc tccccgagga ggtcgaggag gtaattggga ataagccgga gtcggatatt    5340
ctggtgcaca ctgcttacga tgagagcaca gacgagagta ttatgctgct gaccagcgac    5400
gctcctgagt acaagccgtg ggcgctggtt attcaggatt ccaatgggga gaacaagatt    5460
aagatgctgg gatctaagaa gagaagaatt aaacaagat                          5499

SEQ ID NO: 13        moltype = DNA  length = 5499
FEATURE              Location/Qualifiers
misc_feature         1..5499
                     note = base editor
source               1..5499
                     mol_type = other DNA
                     organism = synthetic construct SEQUENCE: 13
ggttcgaaga agagaagaat taaacaagat tcttctgaga ctggcccgt tgctgttgac     60
cccacgctcc gccgccgcat tgagcccac gagttcgagg ttttcttcga cccacgcgag    120
ctgcggaagg agacatgcct cctgtacgag attaattggg gagggcggca ttcgatttgg    180
cggcacacct cgcagaatac aaacaagcac gttgaggtga acttcatcga gaagttcaca    240
accgagcggt acttctgccc caatacgcgg tgctcaatta cttggttcct gtcctggagc    300
ccctgcgggg agtgctccag ggcgatcaca gagttcctgt cccggtatcc acacgtcagc    360
ctcttcatct acatcgctcg gctctaccac catgctgatc cccgcaaccg caggggctc    420
cgcgacctca tttcgtcggg cgtgaccatc cagatcatga cggagcagga gagcggctac    480
tgctggcgca atttcgtcaa ctactcaccc tccaacgagg ctcactggcc tcggtatccc    540
caccctctgg tgcggctcta cgtgctgag ctgtactgca ttattctggg cctcccacca    600
tgcctcaata tcctccgccg gaagcagcca cagctcacct tcttcaccat gctctccag    660
tcctgccatt accagcggct ccctccacat atcctctggg ccactggcct caagtccggc    720
gggtcgagcg gcgggtcgag cggctcagag acacccggta cctcggagtc ggccacacca    780
gagtcgtccg gcggcagcag cggcggctca gacaagagat actccattgg cctggcgatt    840
gggacaaact cggtggggtg ggccgtgatt acgatgagt acaaggttcc aagcaagaag    900
ttcaaggtcc tcgggaacac agatcggcat tcgattaaga agaatctcat tgggggcgctc    960
ctcttcgact cggggggagac agcggaggct accaggctca agcggacagc caggcggcgg    1020
tacacaaggc ggaagaatcg catctgctac ctccaggaga ttttctcgaa tgagatggcg    1080
aaggtggacg acagcttctt ccatcggctg gaggagtcct tcctggtgga ggaggataag    1140
aagcacgaga ggcatccaat tttcgggaac atcgtgacg aggttgcgta ccatgagaag    1200
tacccctaca tctaccatct gcggaagaag ctggttgact ccacagacaa ggcggacctg    1260
aggctgatct acctcgctct ggcccacatg attaagttcc gcgggcattt cctgatcgag    1320
ggggacctga atcccgacaa ttcggatgtg gacaagctct tcatccagct ggtgcagacc    1380
tacaaccagc tgttcgagga gaatcccatc aatgcgtcgg gcgttgacgc taaggccatt    1440
ctgtccgcta ggctgtcgaa gagcaggagg ctggagaacc tgatcgccca gctgccaggc    1500
gagaagaaga atgggctctt cgggaatctg attgcgctca ccctggggct gacaccgaac    1560
ttcaagagca atttcgatct ggctgaggac gcgaagctcc agctctcgaa ggacacttac    1620
gacgatgacc tcgataacct cctgcgcag atcgggacc agtacgctga tctcttcctc    1680
gccgctaaga acctctcgga tgctatcctg ctctccgaca ttctccgggt taataccgag    1740
attacaaagg ccccactgtc ggcgtcatg atcaagcggt acgatgagca tcatcaggat    1800
ctcaccctgc tcaaggccct cgtgcggcag cagctgcccg agaagtacaa ggagatttc    1860
ttcgaccaga gcaagaatgg gtacgctggc tacattgacg gcgggcctc acaggaggag    1920
ttctacaagt tcatcaagcc aatcctggag aagatggatg gacagagga gctgctggtg    1980
aagctcaacc gggaggatct gctcaggaag cagcggacgt tcgacaacgg gtcgattccc    2040
catcagatcc acctggggga gctgcacgcg attctaccct ggcaggagga tttctaccct    2100
ttcctgaagg ataatcggga gaagatcgag aagattctca ccttccgat tcctactac    2160
gtcgggccac tcgcgcgggg caatagcagg ttcgcctgga tgacacgaa gagcgaggag    2220
acaatcaccc cctggaactt cgaggaggtt tcgacaagg gggcgtccgc ccagtcattc    2280
attgagcgga tgaccaattt cgacaagaat ctgccaaatg agaaggttct cccaaagcat    2340
agcctcctct acgagtactt cactgtttac aacgagtga ccaaggtga tatgtgacc    2400
gagggcatgc ggaagcccgc gttcctgtcc ggcgagctga gaaggccat tgtgacctc    2460
ctgttcaaga ccaatcgcaa ggtcacagtc aagcagctca aggaggatta cttcaagaag    2520
atcgagtgct tcgactcggt tgagattagc ggggtggagg atcggttcaa cgcgagcctc    2580
ggcacttacc acgacctcct gaagatcatc aaggataagg acttcctcga caacgaggag    2640
aacgaggata ttctggagga catcgtgctc acccgtgcg ttcggagga tcgggagatg    2700
atcgaggagc gcctgaagac ctacgctcat ctcttcgatg ataaggtcat gaagcagctg    2760
aagaggaggc ggtacaccgg gtggggccgc ctgagcagga agctcattaa cgggatcagg    2820
gacaagcaga gcggcaagac catcctggac ttcctcaaga gcgatggctt cgccaaccgg    2880
aatttcatgc agctcatcca cgacgactcc ctcaccttca aggaggacat tcagaaggct    2940
caggtcagcg gccagggcga ctcgctgcat gagcacatc ctaacctggc gggcagccca    3000
```

```
gccatcaaga agggcatcct ccagacagtg aaggtcgtgg atgagctggt gaaggtcatg    3060
ggccggcata agcccgagaa tattgtgatt gagatggcgc gggagaatca gaccactcag    3120
aagggccaga agaactcgcg ggagcgcatg aagaggatcg aggagggat taaggagctg     3180
ggcagccaga ttctcaagga gcaccccgtg gagaatacccc agctccagaa cgagaagctg    3240
tacctctact acctccagaa tgggcgggac atgtatgttg atcaggagct ggacatcaat    3300
cgcctctcgg attacgacgt ggaccacatc gtgccccaga gcttcctgaa ggatgatagc    3360
atcgacaata aggtcctgac ccgctccgac aagaatcgcg gcaagagcga caacgtgccg    3420
agcgaggagg tcgtgaagaa gatgaagaac tactggcggc agctgctgaa cgcgaagctc    3480
attacacagc ggaagttcga taacctgacg aaggcggaga ggggcggcct ctccgagctg    3540
gacaaggcgg gcttcattaa gaggcagctc gtggagactc gccagatcac caagcacgtg    3600
gctcagatcc tcgatagccg gatgaatacg aagtacgatg agaatgacaa gctcatccgg    3660
gaggtgaagg taatcaccct gaagtcaaag ctcgttagcg atttccggaa ggacttccag    3720
ttctacaagg tgcgggagat taacaactac catcatgcgc acgatgcgta cctcaatgcg    3780
gtggtgggca cagccctgat taagaagtac cccaagctgg agagcgagtt cgtctacggg    3840
gactacaagg tgtacgatgt tcggaagatg atcgccaaga gcgagcagga gattgggaag    3900
gccaccgcta agtacttctt ctactcgaat attatgaatt tcttcaagac cgagatcaca    3960
ctcgctaatg ggagattcg gaagcggccc ctcatcgaga ctaacgggga gactggcgag    4020
attgtgtggg acaaggggcg cgacttcgct accgtgcgca aggtcctctc gatgcccag    4080
gttaatattg ttaagaagac agaggtgcag acgggcgggt tctccaagga gtctatcctg    4140
ccgaagcgga actcggacaa gctgatcgcc cgcaagaagg attgggaccc caagaagtac    4200
gggggattcg atagcccaac cgtggcttac agcgtcctgg tggtcgccaa ggttgagaag    4260
gggaagtcga agaagctcaa gagcgttaag gagctgctgg gcatcaccat catggagcgg    4320
tccagcttcg agaagaatcc tatcgacttc ctggaggcta agggtacaa ggaggtcaag     4380
aaggacctga tcattaagct gcccaagtac tctctgttcg agctggagaa cgggaggaag    4440
cggatgctga cgtctgctgg cgagctacag aagggcaatg agctggcgct ccctcgaag    4500
tatgtcaact tcctctacct ggcttcccat tacgagaagc tgaaggggtc gcccgaggat    4560
aatgagcaga agcagctctt cgtggagcag cacaagcact acctcgacga gatcattgag    4620
cagatttcgg agttctcgaa gcgggtcatt ctcgcggacg cgaacctcga caaggtcctc    4680
tcggcgtaca caagcaccg ggacaagccc atccgggagc aggccgagaa cattatccac    4740
ctcttcacac tgaccaacct cggcgctccc gccgcgttca agtacttcga caccaccatt    4800
gaccgcaaga gatacacatc caccaaggag gtgctggacg cgaccctcat ccaccagagc    4860
atcacaggcc tctacgagac acggatcgac ctctcgcagc tcgggggcga tagcggcggg    4920
tctgggggct ccggcgggtc gacaaacctc agcgatatta cgagaagga gactgggaag    4980
cagctggtaa ttcaggagtc aatcctcatg ctcccagagg aggtggagga ggttatcggg    5040
aacaagccgg agtcggacat tctcgtgcac acggcgtacg atgagtccac tgacgagaat    5100
gtgatgctcc tcacctccga tgcgcccgag tacaagccct gggcgctcgt gattcaggac    5160
tccaacggcg agaataagat caagatgctc agcgggggct ccggcggcag cggcggctcg    5220
acaaacctga gcgatattat tgagaaggag acagggaagc agctggtaat ccaggagagc    5280
attctcatgc tccccgagga ggtcgaggag gtaattggga gcgatatt                5340
ctcgtgcata cagcgtacga tgagtcgaca gatgagaacg tgatgctcct cacatccgac    5400
gctcagagt acaagccgtg ggcgctcgtt attcaggatt ccaatgggga gaacaagatt    5460
aagatgctcg gatctaagaa gagaagaatt aaacaagat                          5499

SEQ ID NO: 14         moltype = DNA   length = 5499
FEATURE               Location/Qualifiers
misc_feature          1..5499
                      note = base editor
source                1..5499
                      mol_type = other DNA
                      organism = synthetic construct
SEQUENCE: 14
ggttcgaaga agagaagaat taaacaagat agcagcgaga caggcccagt tgccgtggac     60
cctactctga ggaggcgcat tgagccccat gagttcgagg tgttcttcga ccccgcgag    120
ctaaggaagg agacatgcct cctctacgag atcaactggg gcgggcggca ttcgatctgg    180
cggcatacaa gccagaacac caataagcac gtggaggtca acttcatcga gaagttcacc    240
accgagaggt acttctgccc aaacacgcgg tgctctatca catggttcct gtcgtggtca    300
ccatgcgggg agtgctcgcg ggcgattact gagttcctgt cgcgctaccc acacgtcacc    360
ctgttcatct acattgcgcg cctgtaccat catgctgacc ccaggaatag gcagggctc    420
cgggacctga tttcctctgg ggtcacaatt cagatcatga ccgagcagga gtcggggtac    480
tgctgcgga acttcgttaa ctacagccca tccaacgagg cgcactggcc acggtatcca    540
cacctgtggg ttcggctcta cgtcctggag ctgtactgca tcatcctcgg gctgccacca    600
tgcctgaaca ttctgcggcg gaagcagccg cagctcacgt tcttcactat tgctctccag    660
agctgccact accagaggct gccacccac attctgtggg cgaccgggct gaagtccggc    720
ggctccagcg gctcgtcgtc aggctcagag acaccaggta cctccgagtc agccaccccc    780
gagtcgtcgg gcgcagctc gggcggctcg acaagaagt actcgatcgg cctggcgatt    840
ggcacaaaca gcgtggggtg ggctgtgatc actgatgagt acaaggtgcc atcgaagaag    900
ttcaaggtgc tgggaataca gaccggcat tcgatcaaga gaatctcat tggcgctctc    960
ctcttcgatt ccggcgagac tgctgaggcg acccgcctga agcgcaccgc ccggcggcgc   1020
tacactcggc ggaagaatag gatttgctac ctccaggaga ttttctcgaa tgagatgccg    1080
aaggtggatg acagcttctt ccaccgcctg gaggagtcgt tcctggtcga ggaggacaag   1140
aagcatgagc ggcaccctat cttcgggaat atcgttgatg aggtcgccta ccacgagaag   1200
taccccacta tctaccatct ccgcaagaag ctcgtggaca gcacagataa ggccgacctc   1260
cgcctgatct acctcgccct cgcgcacatg attaagttcc gggggcactt cctcattgag   1320
ggggatctga atcccgataa ctccgacgtg gataagctcl tcatccagct ggtgcagaca   1380
tacaaccagc tgttcgagga gaatcccatc aacgcgagcg gcgtggacgc taaggccatt   1440
ctgtcggcta ggctctcgaa gtcgaggcgg ctggagaacc tgattgcgca gctccccggc   1500
gagaagaaga acgggctgtt cgggaatctc atcgccctct ccctcggcct cacaccaaac   1560
ttcaagagca atttcgacct ggctgaggac gctaagctgc aactctcaaa ggatacatac    1620
gatgacgacc tggacaatct cctggctcag atcggcgacc agtacgctga cctgttcctc   1680
```

```
gcggccaaga atctgtcgga cgcgattctc ctcagcgaca tcctgcgcgt caataccgag   1740
attacgaagg ctccactgtc tgcgtcaatg attaagcggt acgatgagca tcaccaggat   1800
ctgaccctcc tgaaggcgct cgtgcggcag cagctgcccg agaagtacaa ggagattttc   1860
ttcgatcaga gcaagaatgg ctacgccggc tacatcgacg ggggcgcgag ccaggaggag   1920
ttctacaagt tcatcaagcc catcctggag aagatggacg acaccgagga gctactcgtg   1980
aagctcaatc gggaggatct cctccggaag cagcggacat tcgataacgg gtctatccca   2040
caccagatcc acctcggcga gctgcatgcg attctgcggc ggcaggagga tttctaccct   2100
ttcctgaagg acaaccggga gaagatcgag aagatcctca cattccggat tccatactac   2160
gtcggccccc tggcgagggg caatagccgg ttcgcgtgga tgacaaggaa gtccgaggag   2220
actattaccc cgtggaattt cgaggaggtg gttgacaagg gcgcttccgc gcagagcttc   2280
attgagcgga tgacaaactt cgacaagaat ctccccaacg agaaggtcct gccgaagcat   2340
agcctcctgt acgagtactt caccgtctac aatgagctaa ctaaggtcaa gtatgtgaca   2400
gagggcatga ggaagccagc cttcctctca ggcgagcaga agaaggccat tgtggacctc   2460
ctgttcaaga caaaccgcaa ggtgacagtg aagcagctga gaggagatta cttcaagaag   2520
attgagtgct tcgactcagt ggagatttca ggcgtggagg atcggttcaa cgcgagcctc   2580
gggacttacc acgacctgct gaagattatt aaggacaagg acttcctgga taacgaggag   2640
aatgaggaca tcctggagga tattgtgctc accctcaccc tgttcgagga cagggagatg   2700
attgaggaga ggctcaagac ctacgcgcac ctgttcgatg acaaggtcat gaagcagctg   2760
aagaggcggc gctacactgg gtggggccgc ctgtcgcgga agctgatcaa cggcattcgg   2820
gataagcagt ccgggaagac cattctggat tcctgaagt cggacggctt cgccaacagg   2880
aatttcatgc agctgatcca cgacgactcc ctcaccttca aggaggacat tcagaaggcc   2940
caggttagcg gccagggga ctcactccac gagcatattg ccaatctgcc cggctctcca   3000
gctatcaaga agggcatcct gcaaacagtt aaggttgttg acgagctggt taaggtcatg   3060
gggcggcata agcccgagaa cattgtcatc gagatggctc gggagaacca gacaactcag   3120
aagggccaga agaactccag ggagcgcatg aagcggattg aggagggcat taaggagctg   3180
gggtcccaga tcctcaagga gcaccctgtc gagaacactc agctgcaaaa cgagaagctc   3240
tacctgtact acctccagaa cgggcgggat atgtatgtgg atcaggagct ggacatcaac   3300
aggctctccg actacgacgt ggatcacatt gtcccacagt cttttcctcaa ggatgattcc   3360
atcgacaaca aggtgctgac gcgcagcgac aagaataggg ggaagtcgga caacgttccg   3420
agcgaggagg tcgtgaagaa gatgaagaat tactggaggc agctcctgaa tgcgaagctg   3480
atcactcaga ggaagttcga caatctgaca aaggcggaga ggggcgggct ctcggactg   3540
gataaggcgg gcttcatcaa gcggcagctc gttgaaaccc ggcagatcac caagcatgtc   3600
gcccagatcc tcgatagccg catgaacacc aagtacgatg agaacgacaa gctcattcgg   3660
gaggttaagg tcattacgct gaagtccaag ctcgtcagcg acttcaggaa ggatttccag   3720
ttctacaagg ttcgggagat taacaactac caccacgcgg atgcgta cctgaacgct   3780
gttgtcggca ctgctctcat caagaagtac ccaaagctgg agtccgagtt cgtctacggg   3840
gactacaagg tctacgatgt ccggaagatg atcgccaagt cggagcagga gatcgggaag   3900
gctactgcga agtacttctt ctacagcaac attatgaatt tcttcaagac ggagattacg   3960
ctggcgaacg gggagattag gaagaggccc ctcattgaga ctaatgggga gacaggcgag   4020
attgtttggg acaagggccg cgacttcgcg actgtgcgga aggtcctgtc catgccacag   4080
gtgaatattg ttaagaagac agaggtgcag actgggggct tctcgaagga gagcattctc   4140
ccaaagcgga acagcgataa gctcatcgcg cgcaagaagg attgggaccc taagaagtac   4200
ggcggcttcg attctcccac tgtggcctac tccgttctcg tggttgccaa ggttgagaag   4260
gggaagtcga agaagctgaa gtcggtcaag gagctgctcg ggattacaat catggagcgg   4320
agcagcttcg agaagaaccc tattgatttc ctggaggcca agggctacaa ggaggttaag   4380
aaggatctca ttatcaagct ccctaagtac tctctgttcg agctggagaa tggccggaag   4440
aggatgctgg cctcggctgg cgagctacag aaggggaatg agctgccct cccgtcgaga   4500
tatgtgaatt tcctgtacct cgcgtcgcac tacgagaagc tcaagggcag cccggaggat   4560
aatgagcaga agcagctctt cgtggagcag cataagcact acctggacga gatcattgag   4620
cagatcagcg agttctcgaa gcgggttatt ctggctgatg ctaacctgga caaggttctg   4680
agcgcctaca ataagcatcg cgacaagccc attcgcaagc aggcggagaa tattatccac   4740
ctgttcaccc tcactaacct cggggctccc gcggccttca gtacttcga taccacaata   4800
gataggaagc ggtacacctc gacgaaggag gtcctcgacg ccacactcat ccatcagtcg   4860
attacaggcc tgtacgagac acggattgac ctctcgcagc tgggcggcga tagcggcggg   4920
tccggcggga gcggggcctc gaccaatctg tcggacatca ttgagaaggga aaccggggaag   4980
cagctggtta tccaggagtc catcctcatg ctccccgagg aggttgagga ggtaatcggg   5040
aataagccag agtctgacat cctcgtccac acagcgtacg atgagtcgac agacgagaat   5100
gtcatgctcc tcactagcga tgcgcccgag tacaagcctt gggcgctggt cattcaggat   5160
agcaacggcg agaataagat taagatgctg agcggcgggt cggaggctc tggcgggagc   5220
acgaacctgt ctgacatcat cgagaaggag acaggcaagc agctcgtgat ccaggagagc   5280
attctgatgc tgccggagga ggtggaggag gtaattggca ataagcccga gtctgatatt   5340
ctggtgcaca cagcgtacga cgagagcacg gatgagaatg tcatgctcct gacatccgat   5400
gctcctgagt acaagccgtg ggcgctcgtg attcaggact caaatgggga gaacaagatt   5460
aagatgctcg gatctaagaa gagaagaatt aaacaagat                         5499
```

SEQ ID NO: 15         moltype = DNA   length = 5499
FEATURE                Location/Qualifiers
misc_feature        1..5499
                        note = base editor
source                 1..5499
                        mol_type = other DNA
                        organism = synthetic construct
SEQUENCE: 15

```
ggttcgaaga agagaagaat taaacaagat tcctcggaga ccggcccgt ggcggtggac     60
ccgacgctca ggaggcgcat cgagccgcac gagttcgagg tgttttcga cccgcgcgag    120
ttgcgcaagg aaacctgcct gctctacgag atcaactggg gcggccgaca ttcgatctgg    180
cggcacacca gccagaacac caacaagcac gtggaggtca acttcatcga gaagttcacc    240
accgagcgct acttctgccc gaacacgcgg tgctcgatca cgtggttcct ctcctggtcg    300
ccctgcggcg agtgctcgcg ggccatcacc gagttcctgt cccgctaccc gcacgtcacg    360
```

```
ctcttcatct acatcgcccg gctgtaccac cacgccgacc cccggaaccg ccaggggctg  420
cgggatctca tctcctcggg cgtcacgatc cagatcatga ccgaacagga gtcgggctac  480
tgctggcgga acttcgtgaa ctactcgccg agcaacgagg cccactggcc gcgctacccg  540
cacctgtggg tccggctgta cgtgctgagc tgtactgca tcatcctcgg cctaccgccg  600
tgcctcaaca tcctccgccg gaagcagccg cagctcacat tcttccaccat cgcccttcag  660
agctgccact accagcgcct gccgccgcac atcctgtggg ccaccgggct caagagcggc  720
ggttccagcg gcggctcgtc tggctccgag actcccggca ccagcgagag cgcgacgccc  780
gagtcgagcg gcggttcatc tggcgggagc gacaagaagt attccatagg cctggctatc  840
ggcaccaaca gcgtgggctg ggccgtcatc accgacgagt acaaagtgcc gagtaaaaag  900
ttcaaagtgc tcggcaacac cgaccgccac tccataaaga aaaacctgat cggggcgctc  960
ctgttcgaca gcgcgagac ggcggaggcc acccgcttga aacgcacggc ccgacggcgc  1020
tacacgcggc gcaagaaccg gatctgttac ctacaggaga ttttctctaa cgagatggcg  1080
aaggtggacg actcgttctt tcaccgcctc gaagagtcct tcctcgtgga ggaggacaag  1140
aaacacgagc gccacccgat cttcggcaac atcgtcgagga aggtggccta ccacgagaag  1200
tacccgacca tctaccacct ccggaagaaa ctcgtggaca gcacggacaa ggccgacctg  1260
aggctcatct acctcgccct ggcgcacatg attaagttcc ggggccactt cctgatcgag  1320
ggcgacctga acccggacaa cagcgacgtg gacaagctgt tcatccagct agtccagacc  1380
tacaaccagc ttttcgagga aaaccccatc aacgccagcg gggtggacgc gaaggcgatc  1440
ctgtccgccc ggctgagcaa gtccggcgcg ctggagaacc tcatcgcgca gttgcccggc  1500
gagaagaaga acgggctgtt cgggaacctg atcgccctct ccctggggct caccccgaac  1560
ttcaagtcca acttcgacct cgccgaggac gccaaactac agctgagcaa ggacacctac  1620
gacgacgaca tcgacaacct cgcgcccag atcggggacg agtacgacag cctgttcctc  1680
gccgccaaga acctctccga cgccatcctg ctgtcggaca tcctgcgggt gaacacggag  1740
atcacgaagg ccccgctctc ggcctcgatg attaaacgct acgacgagca ccaccaggac  1800
ttgacccctc tcaaggcgct ggtccgccag cagcttcccg agaagtacaa ggaaatcttt  1860
ttcgatcaga gcaagaacgg gtacgccggg tacatcgacg gcggggcgtc ccaggaggag  1920
ttctacaagt tcatcaagcc catcctggag aaaatgacg ggaccgagga gctgctcgtg  1980
aagctcaacc gcgaagattt gctccgcaag cagcgcacgt tcgacaacgg gtcgatcccg  2040
caccagatcc acctgggcga gctgcacgcg atcctcaggc gtcaggaaga cttctacccc  2100
ttcctcaagg acaaccgcga gaagatacag aagattctga ccttcagaat tccttattac  2160
gtgggcccgc tggctcgggg caactcgcgc ttcgcctgga tgacgcgcaa gtccgaggag  2220
accatcaccc cgtggaactt cgaggaggtg gtggataagg gtgcctcggc ccagtccttc  2280
atcgagcgga tgaccaactt cgacaagaac ctgccgaacg agaaggtgct ccccaagcac  2340
agcctgctct acgaatattt cacggtgtac aacgagacc cgaaggtcaa gtacgtgacc  2400
gagggaatga ggaaacctgc attcctctcc ggggagcaga agaaagccat agtcgacctc  2460
ctgttcaaga ccaaccggaa ggtcaccgtc aagcagctca aggaggacta cttcaagaag  2520
atcgagtgct tcgattcagt ggagatcagc ggcgtcgagg accggttcaa cgccagcctg  2580
ggcacctacc acgacctgct caagatcatc aaggacaagg acttcctcga caacgaggag  2640
aacgaggaca tcctggagga catcgtcgg acctcgacg tcttcgagga ccgcgagatg  2700
atcgaggagc gcctcaagac ctacgcccac ctgttcgacg acaaggtgat gaagcagctc  2760
aagcggcgga gatatactgg gtggggccgc ctctcccgga agctcattaa cggtatcagg  2820
gataagcagt ccgggaagac gatcctcgac ttcctcaagt cggacgggtt cgccaaccgc  2880
aacttcatgc agctcatcca cgacgactcc ctgacgttca aggaggacat ccagaaggcc  2940
caagtgtctg gtcaaggtga ctcgctccac gagcacatcg ccaacctcgc gggcagcccg  3000
gccatcaaga agggaatact ccagaccgtc aagtggtgg acgagctggt gaaggtcatg  3060
ggccgccaca agcggagaa catcgtcatc gagatggcgc gggagaacca gaccacgcag  3120
aagggggaag aaaatagccg tgagcgcagt aagcgcatcg agggaggggat taaggagttg  3180
ggcagccaga tcctcaagga gcaccctgtg gagaacacgc agttgcaaaa cgagaagctc  3240
tacctgtact acctccagaa cgggagggat atgtacgtgg accaagaact ggacatcaac  3300
cgcctgtccg actacgacgt ggaccacatc gtgccgcaga gcttcctcaa ggacgacagc  3360
atcgacaaca aggtgctcac ccggtccgac aagaatcgag gcaagtccga caacgtgccc  3420
agcgaggagg tcgtcaaaaa gatgaaaaac tactggcgac aactactgaa cgccaagctc  3480
atcacccagc gcaagttcga caacctcaca aaagccgagc gcggcgggtt gagcgagctg  3540
gacaaggccg ggttcatcaa gcgccagctc gtcgagacgc cccagatcac gaagcacgtc  3600
gcgcagatac tcgacagccg gatgaacacc aagtacgacg agaacgacaa gctcatccga  3660
gaggtgaagg tcatcaccct caagtcgaag ctcgtgagcg acttccgcaa ggacttccaa  3720
ttctacaagg tccgggagat caacaactac caccacgccc acgatgctta tcttaacgcc  3780
gtggtgggga cggccctcat taagaaatac ccgaagctgg agtcggagtt cgtgtacggc  3840
gactacaagg tgtacgacgt caggaagatg atcgccaagt ccgaacagga gatcgggaag  3900
gccacggcga aatacttctt ctacagcaac atcatgaact tcttcaagac cgagatcacc  3960
ctcgccaacg gcgagatccg caagcgcccg ctcatcgaga cgaacgggga gaccggcgag  4020
atcgtctggg acaaggggcg cgacttcgcc actgtgcgga aggtgctgtc gatgcccag  4080
gtcaacatcg tcaagaagac ggaggtccag acgggcgggt tcagcaagga gagcatcctg  4140
ccgaagcgca acagccgacaa gctgatcgcc cgcaaaaagg actgggatcc aaaaaagtac  4200
ggcggcttcg acagccccac cgtcgcctac agcgtcctcg tcgtcgctaa gtcgagaag  4260
ggcaagtcca aaaagctcaa gagcgtcaag gagctgctcg gatcaccat catggagcgg  4320
tccagcttcg agaagaaccc aattgatttc ctggaggcga agggctacaa ggaggtcaag  4380
aaagacctca tcataaagct gccgaagtac tcactcttcg agctggagaa cgggcgcaag  4440
cggatgctgg cgtcggccgg agagctccaa aagggcaacg agctggcgct gccgagcaag  4500
tacgtgaact tcctctacct ggcgtcccac tacgagaagc tcaagggcag tccagaggat  4560
aacgagcaga agcagctatt cgtcgagcag cacaagcact acctggacga gatcatcgag  4620
cagatcagcg agttctccaa gcgcgtcatc ctggcggacc caacctggaa caaggtgctg  4680
tccgcgtaca acaagcaccg cgacaagccg atccgcgagc aagccgagaa catcatccac  4740
ctgttcaccc tcacgaactt cgggcacccg gccgcttca aatatttcga cacgaccatc  4800
gaccgcaagc gctacaccag cacgaaggag gtgctcgacg ccaccctgat ccaccagagc  4860
atcaccggc tgtacgagac ccgcatcgac ctctcgcagc tcggcgggga cagcggtggc  4920
tcgggcgggct cgggcgggag caccaacctg agcgacatca tcgagaagga cacgggcaag  4980
cagctcgtga tccaggagtc catcctcatg ctcccgagg aggtcgagga ggtgatcggc  5040
aacaagccag agtcggacat cctggtgcac accgcgtacg acgagtccac cgacgagaac  5100
```

```
gtcatgctgc tcaccagcga cgccccagag tacaagccct gggccctggt catacaggac    5160
tcgaacgggg agaacaagat caagatgctc tctggcggca gcggcgggag cggcggctcg    5220
accaacctca gcgacatcat cgagaaggag accggcaagc agttggtgat ccaggagagc    5280
atactgatgc tccccgagga ggtggaggag gtgatcggca caagccgga gtcggacatc    5340
ctggtgcaca cggcgtacga cgagagcacg gacgagaacg tgatgctgct gacgtctgat    5400
gcgcccgagt acaagccctg ggccctggtg atccaggaca gcaacgggga gaacaagatc    5460
aagatgctgg gatctaagaa gagaagaatt aaacaagat                           5499
```

| SEQ ID NO: 16 | moltype = DNA   length = 5499 |
|---|---|
| FEATURE | Location/Qualifiers |
| misc_feature | 1..5499 |
| | note = base editor |
| source | 1..5499 |
| | mol_type = other DNA |
| | organism = synthetic construct |

```
SEQUENCE: 16
ggttcgaaga agagaagaat taaacaagat tcgtccgaga ccggcccccgt ggctgtggac    60
ccgacccttc gcagacgtat cgagccccac gagttcgagg tgttctttga cccgagggaa    120
ctccggaagg agacgtgcct gctctacgag atcaactggg gaggaagaca ctccatctgg    180
cggcacacct cgcagaacac gaacaagcac gtggaggtca acttcatcga gaagttcacg    240
actgagcggt acttctgtcc gaacacgcgg tgctcgatca catggttcct gtcttggagc    300
ccgtgcgggg agtgctctcg ggccattacc gagttcctcc cccgctaccc gcacgtcacg    360
ctgttcatct acattgcgcg gctataccac cacgccgatc cacggaaccg caagggcctc    420
cgcgacctta tcagctccgg cgtgacgatc cagatcatga ccgagcaaga gtccgggtac    480
tgctggcgca acttcgtcaa ctactcaccg tccaacgagg cgcactggcc gcgttaccct    540
catctctggg tccggctgta cgtgctggag ctgtactgca taatcctgag cctgccgctc    600
tgcctgaaca tcctcaggcg gaagcagccc aacttacat tttttcaccat gcgctccag    660
tcctgccact accagcgtct gccgcccac atcctgtggg ccaccggctt gaagtccggt    720
ggctcgtccg gcgggctccag cgggagcgag acgccgggca ccagcgagtc cgccacgcct    780
gagtccagcg gcggctccag cggcggttcg gacaagagt acagtattgg attggccatc    840
gggacgaaca gcgtgggctg ggccgtcatc accgacgagt acaaggtgcc atccaagaag    900
tttaaggttc tggggaatac cgaccgccac tcgatcaaga aaatctcat cggggcgctg    960
ctttcgacag gcgcgagac ggcggaagcg acgcggctca agcggacggc tcgtcgccgt    1020
tacaccccgg gtaagaaccg catctgttac ctccaggaga tattcagcaa cgagatggcg    1080
aaggtggacg actccttttt ccaccgtctt gaggagtcct tcctggtcga ggaggacaag    1140
aagcacgagc gccacccgat cttcgggaac atcgtggacg aggtggccta ccacgagaag    1200
taccccacga tctaccacct ccgcaaaaaa ctcgtggact caactgacaa ggccgatttg    1260
aggcttatct acctcgccct cgcccacatg attaagttcc gtgggcactt cctaatcgag    1320
ggtgacctca accccgacaa ctctgacgtg gacaagctgt tcatccagct tgtgcagacc    1380
tacaatcagc tctttgagga gaatccgatc aacgcatctg gtgtggacgc aaaggccatc    1440
ctcagcgcgc ggctgagcaa gtctaggcgg ttggagaacc tgatcgccca actgcccggc    1500
gagaagaaaa atggcctctt cggcaacctg atcgccctgt cgctgggct cacgccgaac    1560
ttcaagagta actttgacct ggcggaggac gctaagctcc agttatctaa ggacacataa    1620
gacgacgacc tggacaacct gctgcccag atcggcgacc agtacgccga cctcttccta    1680
gccgccaaga acctgtccga cgccatcctc tcagcgaca tcctgcgcgt gaacacggag    1740
atcacgaagg ctccgctcag cgcctccatg attaagcggt acgacgagca ccaccaagac    1800
ctaactttac tcaaagccct cgtgcggcag cagcttcccg agaagtacaa agagatattt    1860
tttgatcagt ccaagaacgg ttatgcgggc tacatcgacg gcggcgcgag ccaggaggag    1920
ttctacaagt tcatcaagcc catcctggag aagatggacg gcacggagga gctgctcgtg    1980
aagctcaacc gtgaagacct cctgcgaaag cagcgaacct tcgacaacgg ttcgatcccg    2040
caccagatcc acctcgggga gctgcacgcc atcctgaggc gacaggagga cttctaccct    2100
ttcctaaagg acaaccgcga gaagattgaa aaaatcctga cgtttcgcat acctactac    2160
gtcggccgc tggcgcgcgg caactcccgg ttcgcctgga tgaccgtaa gagcgaggag    2220
acgatcaccc cgtggaactt cgaggaggtc gtggacaagg cgcgagcgc gcagagcttc    2280
atcgagcgca tgaccaactt cgacaagaac ctcccgaacg agaaggtgct cccaaagcac    2340
tccctcctgt acgagtattt caccgtgtac aacgagttga caaaggtgaa gtacgtgacg    2400
gagggaatgc ggaagcctgc gttcctctcg ggcgagcaga gaaggcaat cgtggacctg    2460
ctcttcaaga ccaaccggaa ggtgacggtg aagcagctca aggaggacta cttcaaaaaa    2520
atcgagtgct tcgactccgt ggagataagc ggcgtggagg accgattcaa cgcctccctc    2580
ggcacctacc acgaccttcct taagatcatc aaggacaagg acttcctgga caacgaggag    2640
aacgaggaca tcctggagga catcgtgctc accctgaccc tcttcgagga ccgggagatg    2700
atcgaggagc gcctcaagac gtacgcccac ttgttcgacg acaaggtgat gaagcagctc    2760
aagcggcggc gatacaccgg gtggggccgc ctatcccgca acttatcaa cggcatccgc    2820
gacaagcagt ccggcaagac gatcctggat ttcctcaagt cggacggtt cgccaaccgg    2880
aacttcatgc agctcatcca cgacgacagc ctcacgttca aggaggacat ccagaaggcc    2940
caagtgagcg gtcaagggga cagcctccac gagcacattg cgaacttgc tgggagccct    3000
gcgatcaaga aggggatatt gcaaaccgtg aaggtcgtgg acgagttggt gaaggtcatg    3060
gggcgacaca gcccgagaa catcgtgatc gagatggcca gggaaaatca gaccacgcag    3120
aagggccaaa aaaaccccg cgagcggatg aagcggatcg aagagggaat caaggagctg    3180
gggtcgcaga tcctcaagga gcacccggtg gagaacacgc agctccagaa cgagaagctg    3240
tacctctatt acctacagaa cggcggggat atgtacgtgg accaggagct agacatcaac    3300
cgcctgtccg actacgacgt ggaccatatc gtcccgcagt cgttcttgaa ggacgacagc    3360
atcgacaaca aggtgctcac aagatcggat aagaatcgag gcagtccga caacgtgccc    3420
tcggaggtga tggtcaagaa aatgaaaaac tactgcagg agttgctgaa cgccaagctg    3480
attacgcagc ggaagttcga caacctgacg aaggctgaac gtggtgggct cagcgagcta    3540
gacaaggcgg ggttcatcaa gcggcagctc gtcgagaccc ggcagatcac caagcacgtg    3600
gcgcagatcc tggactcgcg catgaacacc aagtacgacg agaacgacaa gctcatccgt    3660
gaggtgaagg tcatcacccct taagtctaag ctggtcagtg acttccgcaa ggacttccag    3720
ttctacaagt tccggggagat caacaactac caccacgcgc acgacgccta cctcaacgcg    3780
```

| | | | | |
|---|---|---|---|---|
| gtggtgggga | cggcgcttat | taagaaatat | cccaagctgg | aaagcgagtt cgtttacggc | 3840 |
| gactacaagg | tgtacgacgt | ccgcaagatg | atcgcaaagt | cggaacagga aatcggaaag | 3900 |
| gcgacggcca | aatatttctt | ttactccaac | atcatgaatt | tttttaagac ggagatcacc | 3960 |
| ctggcgaacg | gggagatccg | caagcggccc | ctcatcgaga | ccaacgggga gacgggcgag | 4020 |
| atcgtctggg | acaagggccg | ggacttcgcc | accgtgcaga | aggtgctttc tatgcctcaa | 4080 |
| gtcaatatcg | tcaaaaagac | agaggtgcag | accggcgggt | tcagcaagga gtctatcctg | 4140 |
| ccgaagcgca | actcggacaa | gctcatcgcg | cgcaagaaag | actgggaccc caaaaaatat | 4200 |
| ggcgggttcg | actcgccgac | cgtcgcctac | agcgtcctcg | tggtggctaa ggtcgagaag | 4260 |
| ggcaagagca | aaaagctaaa | gtcggtgaag | gagctgctgg | gcatccaccat catggagcgc | 4320 |
| tcgtctttcg | agaagaatcc | aatcgacttc | ctagagcgaa | aggggtacaa ggaggtcaaa | 4380 |
| aaggatctta | tcatcaaact | gccgaagtac | agtctgttcg | agctggagaa cgggcggaag | 4440 |
| cggatgctga | ctagtgcggg | cgagttgcag | aagggcaacg | agttggcact gcctccaag | 4500 |
| tacgtgaact | tcctgtacct | ggcctccac | tacgagaagc | tcaaggggag ccccgaggac | 4560 |
| aacgagcaga | agcagctatt | cgtcgagcaa | cacaagcact | acctgacgac gatcatcgag | 4620 |
| cagatcagtg | agttctccaa | gcgggtcatc | ctcgcggacg | ccaacctgga caaggtgctg | 4680 |
| agcgcgtaca | acaagcacag | ggacaagcca | atcagggaac | aggccgagaa catcatccac | 4740 |
| ctgttcaccc | tgaccaacct | gggtgcaccg | gctgccttca | agtactttga cacgaccatc | 4800 |
| gaccgaaagc | gctacacctc | cacgaaggag | gtgctgaacg | ccacgctgat ccaccagacg | 4860 |
| atcaccgggc | tctacgagac | acggatcgac | ctgagccagc | ttggcgggga ctcgggcggc | 4920 |
| agcggcggta | gcggcgggag | caccaacctc | tccgacatca | tcgagaagga gacggggaag | 4980 |
| cagttggtga | tccaggagag | catcctcatg | ctgccggagg | aggtcgagga ggtgatcggg | 5040 |
| aacaagccgg | agtcggacat | tctcgtgcac | acagcctacg | acgagtccac gacgagaac | 5100 |
| gtcatgctcc | tgacctcgga | cgccccggag | tacaagccct | gggcgctggt gatccaggac | 5160 |
| agcaacggcg | agaacaagat | caagatgctg | tccggcggca | gcggtggcag cggcgggagc | 5220 |
| accaacctga | gcgacatcat | cgagaaggag | acaggcaagc | agctcgtgat ccaggagtcg | 5280 |
| atactgatgc | tccccgagga | ggtcgaggag | gtcatcggga | acaagcccga gtcagacatc | 5340 |
| ctcgtgcaca | ccgcctacga | cgagagcacg | gacgagaacg | tgatgctcct gacctcgac | 5400 |
| gcaccggagt | acaagccctg | ggccctggtc | atccaggaca | gcaacggcga gaacaagatc | 5460 |
| aagatgctcg | gatctaagaa | gagaagaatt | aaacaagat | | 5499 |

SEQ ID NO: 17        moltype = DNA  length = 5499
FEATURE              Location/Qualifiers
misc_feature       1..5499
                       note = base editor
source               1..5499
                       mol_type = other DNA
                       organism = synthetic construct
SEQUENCE: 17

| | | | | |
|---|---|---|---|---|
| ggttcgaaga | agagaagaat | taaacaagat | tcatccgaga | cggggcccgt cgccgtggac | 60 |
| cccacgctca | gacgccggat | cgagcccac | gagttcgagg | tcttttcga cccgagagag | 120 |
| ctacgaaagg | agacctgcct | gctgtacgag | atcaactggg | gcgggcggca ttcgatctgg | 180 |
| cggcacacga | gccagaacac | gaacaagcac | gtggaggtca | acttcatcga gaagttcacg | 240 |
| acggacggt | acttcgtgcc | caacacccgc | tgctctatca | cctggttcct gtcgtggagc | 300 |
| ccgtgcggcg | agtgcagccg | cgccatcacg | gagttcctca | gccgctatcc tcacgtgacc | 360 |
| ctgttcatct | acatcgcgcg | gctctaccac | cacgccgacc | cacgcaaccg ccaggggctg | 420 |
| cgcgacttaa | tcagctccgg | ggtcacgatc | cagatcatga | cggaacaaga gtccggctat | 480 |
| tgctgggaca | acttcgtcaa | ctacagcccg | agtaacgagg | cccactggcc gcgctacccg | 540 |
| cacctctggg | tccggctgta | cgtcctggag | ctgtactgca | tcatattggg gctcccgccg | 600 |
| tgtctcaaca | tcctccggcg | gaagcagccc | cagctcacat | tctttactat agcccttgcag | 660 |
| tcgtgccact | accagcgcct | cccgccgcac | atccctcggg | cgaccgggct taagagcggt | 720 |
| ggctcgagcg | gcggtagcag | cggcggcgag | acgcccggca | gcgagcgtc tgccactcca | 780 |
| gaatcatctg | gcggctccag | cggcggttcc | gacaaaaagt | attccattgg actcgctatc | 840 |
| ggcacgaaca | gcgtcgggtg | ggcggtcatc | actgacgagt | acaaggtgcc gagcaagaag | 900 |
| tttaaggtgc | tggaaacac | gacaggcac | tcgatcaaga | aaaatcttat cggggcccta | 960 |
| ctcttcgact | ccggagaaac | cgccgaggcc | acccggttga | agcgcacggc ccgccgtgcg | 1020 |
| tacaccaggc | gcaagaaccg | gatctgctac | ctccaggaga | tattcagcaa tgagatggcc | 1080 |
| aaggtggacg | actcgttttt | tcacaggcta | gaggagtctt | tcctcgtgga ggaggacaag | 1140 |
| aaacacgagc | gccaccccat | cttcggcaac | atcgtggatg | aggtggcata tcacgagaag | 1200 |
| taccaacca | tctaccacct | ccgcaaaaag | ctcgtggact | ctaccgacaa ggccgacctc | 1260 |
| cgtctgatct | acctcgcgct | ggcccacatg | attaagttcc | gaggacactt tctgatcgag | 1320 |
| ggcgacctga | acccagacaa | cagcgacgtg | gacaagctgt | tcatccaact tgtccagacc | 1380 |
| tacaatcagc | tcttcgagga | aaccctatc | aacgcctcgg | gcgtggacgc gaaggccatc | 1440 |
| ctgtccgccc | gcctgagcaa | gtcgcggcgg | ctggagaacc | tgatcgccca gctccccggc | 1500 |
| gaaaaaaaga | acggcctctt | cggcaacctc | atcgcgttgt | cgctggggct caccccgaac | 1560 |
| ttcaagtcca | acttcgacct | ggccgaggac | gctaaactcc | agctctcgaa ggataccac | 1620 |
| gacgacgacc | tcgacaacct | gctggcccag | atcggcgacc | agtacgcgga ccttttcctg | 1680 |
| gcggccaaga | acctgagcga | cgcgatcctc | cttagcgaca | tactccgtgt gaacaccgag | 1740 |
| atcacgaagg | cccccgctctc | cgcgtccatg | attaagcgct | acgacgagca ccaccaagac | 1800 |
| cttaccctgc | ttaaggcgct | ggtcaggcag | cagttaccgg | agaagtacaa ggagatcttt | 1860 |
| tttgatcaat | ctaagaacgg | ttacgccggg | tacatcgacg | gcgcgcgtc ccaggaggag | 1920 |
| ttctacaagt | tcatcaagcc | gatcttggag | aaaatggacg | gaccgaggag gctgctcgtg | 1980 |
| aagctcaacc | gcgaagacct | cctccgcaag | cagcgcacct | tcgacaacgg gagcatcccg | 2040 |
| caccagatcc | acctgggaga | gctgcacgcg | atcctgcgga | gacaagagga cttctacccc | 2100 |
| ttcctcaaga | acaaccggga | agattgaa | aaaatacttga | cttttcgtat cccgtactac | 2160 |
| gtcgggcccc | ttgcgagggg | caactccaga | ttcgcgtgga | tgaccgcaa gtccgaggag | 2220 |
| accatcaccc | cgtggaactt | cgaggaggtg | gtggacaagg | gcgcgtcggc ccagtcgttc | 2280 |
| atcgagcgca | tgaccaactt | cgacaagaac | cttccgaacg | agaaggtgct cccgaagcac | 2340 |
| agcctgctct | acgaatattt | tactgtgtac | aacgagctga | cgaaggtcaa gtacgttacg | 2400 |
| gagggggatga | ggaagcccgc | cttcctctcc | ggcgagcaga | agaaagccat tgtggatctc | 2460 |

```
ctgttcaaga ccaaccgcaa ggtgacggtg aaacagctca aagaggacta cttcaagaag 2520
atcgagtgct tcgactccgt agagatcagc ggggtcgagg accgcttcaa cgcctcgctg 2580
ggcacgtacc acgacctgct aaagattatc aaggacaaag acttcctaga caatgaggag 2640
aacgaggaca ttctggagga catcgtgctg actctgacgc tgttcgaaga ccgcgagatg 2700
atcgagtgca ggcttaagac gtacgcccac ctgttcgacg acaaggtgat gaagcagttg 2760
aaacggcggc gctacaccgg gtggggccgc ctctcccgca agctcatcaa cggcatccgc 2820
gacaagcagt cggggaagac gatcctggac ttcctcaaga gcgacggctt cgccaaccga 2880
aacttcatgc agctaatcca cgacgacagc ctgacgttca aggaggacat ccagaaggcc 2940
caagtgagcg gccagggaga ctcgctacac gagcatatcg ccaacctggc tggcagccgg 3000
gcgattaaga aggaatcct ccaaaccgtc aaagtggtgg acgagctggt gaaggtgatg 3060
ggccgccaca agcccgagaa cattgtgatc gagatggcgc gggagaacca gacgacgcag 3120
aagggccaaa aaatagcag ggaaaggatg aagcgaatag aggaggggat caaggagctg 3180
gggagccaga ttctcaaaga gcaccggtc gagaacacac agctccagaa cgagaagctg 3240
tacctctact acctccaaaa cggccgcgat atgtacgtcg accagaact agacatcaac 3300
cggctgagcg actatgacgt ggaccacatc gtgccgcagt ccttcctcaa ggacgactcg 3360
attgacaaca aagtgctcac tagatccgac aagaacagag gcaagagcga taacgtcccg 3420
tcggaggagg tcgtcaagaa aatgaaaaac tactggcggc agctcctaaa cgccaagctc 3480
atcacgcagc gtaagttcga caacctgacg aaggcggagc ggggcgggct gagcgagctg 3540
gacaaagcgg ggttcatcaa gcggcagctc gttgagacgc ggcagatcac aaagcacgtc 3600
gcgcaaatcc tcgactcccg catgaacacc aagtacgacg agaacgacaa gctcatccgg 3660
gaggtgaagg tcattaccct taaatcgaag ctcgtcagcg actttcgtaa ggacttccag 3720
ttctacaagg tcagagagat caacaactac caccacgccg acgacgccta tctgaacgcc 3780
gtggtgggca ccgcgcttat taagaagtac cccaagctgg agtccgagtt cgtgtacggc 3840
gactacaagg tttatgacgt caggaagatg atcgccaagt cggaacagga gatcggaaaa 3900
gctaccgcca aatatttctt ctatagcaac atcatgaact tcttcaaaac cgagatcacc 3960
ctcgccaacg gcgagatccg gaagcgcccg ctcatcgaaa ccaacggcga gaccgggaag 4020
atcgtctggg acaaggggcg ggacttcgct actgtccgaa aggtgctctc catgccacaa 4080
gtgaatatcg tcaagaaaac agaggtgcag accggagggt tcagtaagga gtccatcctg 4140
cccaagcgga actccgacaa gctaattgct cgcaaaaagg attgggatcc taaaaaatat 4200
ggcggcttcg actcgcccac ggtcgcctac tctgtgctgg tcgtggcgaa ggtggagaag 4260
ggcaagtcca agaagctcaa gagcgtcaag gagctgctgg ggatcacgat catggagcgt 4320
agttcgtttg agaagaatcc catcgacttc ctggaggcta agggctacaa ggaggtcaaa 4380
aaggacctca tcattaagct gccgaagtac agcctcttcg agctggagaa cgggcggaag 4440
cgtatgctcg cctccgctgg ggagttacaa aaggggaacg agctgcgct gccgtctaag 4500
tacgtcaact tcctgtacct ggcctcccac tacgagaagc tcaagggtc gccggaggac 4560
aacgagcaga agcagctctt cgtagagcag cacaagcact acctggacga gatcatcgag 4620
cagatttcag agttctcaaa gcgggtcatc ctcgccgacg ccaacctgga caaggtgctc 4680
tcggcctaca acaagcaccg ggacaagccg atccgcgaac aggccgaaaa catcatccac 4740
ctgttcacgc tcaccaacct cggtgcccg gcggccttca agtactttga cacgaccatc 4800
gaccggaagc gctataccct gacgaaggag gtgctggacg ccacgctgat ccaccagtcc 4860
atcaccgggc tttacgagac ccggatcgac ctctcgcagc taggcgggga ctcgggcggc 4920
tcgggcggct ccggcgggag caccaacctg tccgacatca tcgagaagga gacgggaag 4980
cagctcgtca tccaggagtc gatcctcatg ctccccgagg aggtcgagga ggtgatcggc 5040
aacaagccgg agtccgacat cctggtccaa acggcgtacg acgagagcac ggacgagaac 5100
gtgatgctcc tgacctccga cgccccggag tacaagccct gggcgctcgt catccaggac 5160
agcaacggcg agaacaagat caagatgctc tccggcggct ccggcggcag cggagggagc 5220
acgaacctca gcgacatcat cgagaaggcg accggagga agctcgtgat ccaggagtcc 5280
atcctcatgc tgccggagga ggtggaggag gtgatcggca acaagccgga gtcggacata 5340
ctcgtgcaca ccgcgtatga cgagagcacc gacgagaacg tgatgctgct gacaagcgac 5400
gcgccagagt acaagccctg ggcccctcgtg atccaggact ccaacggcga gaacaagatt 5460
aagatgctgg atctaagaa gagaagaatt aaacaagat 5499
```

SEQ ID NO: 18        moltype = DNA  length = 5499
FEATURE               Location/Qualifiers
misc_feature       1..5499
                        note = base editor
source                1..5499
                        mol_type = other DNA
                        organism = synthetic construct
SEQUENCE: 18

```
ggatctaaga agagaagaat taaacaagat tcatcagaga caggaccagt tgccgttgac 60
cccaccctta ggagaagaat agaaccccac gagtttgaag tgttttcga cccaagagaa 120
ttgaggaagg aaacatgtct tctgtatgag ataaattggg gaggtaggca cagcatttgg 180
agacatacca gccagaatac aaacaagcat gttgagtcta attttattga aagttcact 240
accgaaagat attttgtcc aaacactaga tgtagtataa cctggttct cagttggagc 300
ccatgtgggg aatgtagcag ggcaataccc gagtttctct caagataccc tcacgtgacc 360
ttgtttatct acatagccag actttatcat cacgcagacc caagaaacag acaaggtctg 420
agagatttga tttcttcagg agtgactatt cagatcatga ccgaacaaga gagcggttac 480
tgctggagaa actttgttaa ttattcact agtaacgaag cacattggcc tagataccct 540
caccgtgtgg ttaggctcta cgtgttggaa ctctattgca ttattcttgg cttgcctccc 600
tgcctgaaca tactgagaag gaagcagccc caactcacat tcttcactat agctctgcaa 660
agttgtcact accagaggct ccctcctcac atcctgtggg ccacaggttt gaagtcaggg 720
ggctccagtg gaggtagttc aggctccgag actccggaa cttccgagtc agctacaccc 780
gaatgattgg gtggtaagttc tggcggcagt gacaagaggt atagtattgg actcgccatc 840
ggaaccaact ctgtggggtg ggctgttatt acagatgaat ataaggtgcc atccaaaaag 900
tttaaagttc tggcaatac tgatagacac tcaatcaaga agaatctgat aggtgcactt 960
ctgtttgata gtgagagac tgccgaggca accagactta aaaggactgc aagaagaaga 1020
tataccagaa gaaagaatag gatttgctat ttgcaggaaa tcttcagcaa cgaaatggcc 1080
aaggttgatg actcattttt ccataggttg gaggagagtt ttcttgtgga ggaagataag 1140
```

```
aagcacgaaa gacacccaat tttcgggaat atagtggacg aggtggctta tcatgagaag   1200
tatcccacta tctaccacct gagaaagaaa cttgtggact caaccgataa ggctgatctt   1260
aggcttatat acttggcect tgcacatatg atcaaattca ggggccattt tcttatcgaa   1320
ggcgatctta atcccgataa ctcagatgtg acaagctgt ttataacaact tgtgcaaacc    1380
tacaatcaac tcttcgagga gaatcccatt aacgcctccg gcgtggatgc aaaagccata   1440
ctgtcagcca gactgagcaa aagtaggaga ctggagaatc ttatagccca actgccggt    1500
gaaaagaaga atgggctctt cggaaatctg atcgctcttt cattgggtt gacacccaac    1560
tttaagagta actttgactt ggcagaagat gcaaagttgc agctcagtaa agacacatat   1620
gacgatgacc ttgacaatct cttggcacaa ataggggatc aatacgctga cctttcctc    1680
gctgccaaga accctcagcga cgctatactg ttgtccgaca ttcttaggg taataccgaa   1740
attacaaagg cccctcttag tgcaagtatg atcaaaaggt atgatgagca tcaccaagac   1800
cttacactgc tgaaggctct ggttagacag caactccctg aaaagtataa ggaaatattc   1860
ttcgaccaaa gtaagaacgg gtacgccggt tatattgatg ggggcgcaag tcaagaagaa   1920
ttttacaaat tcatcaagcc aattcttgaa aagatggacg ggactgagga attgctggtg   1980
aaactgaata gagaggacct tcttagaaaa cagaggacat ttgacaatgg gtccatccca   2040
caccagattc atctggggga actccacgca atattgagga gacaagaaga cttttaccca   2100
ttccttaagg ataatagaga gaaatcgaa aaatcctga ctttcaggat tccttactat     2160
gttgggccac tggccaggg gaactcaaga ttcgcttgga tgacaaggaa gtcagaagaa   2220
accataaccc cttggaattt tgaagaggtg gttgataagg gggcatcagc ccagtctttc   2280
atagagagga tgaccaactt tgataaaaat cttccaaatg agaaggtttt gccaaaacat   2340
agtcttttgt acgagtactt tactgtttat aacgaattga ccaaggtgaa gtatgtgacc   2400
gagggaatga ggaagccagc atttttgtcc ggggagcaaa gaaaagcaat cgttgatctt   2460
ctcttcaaga ccaacagaaa agtgaccgtg aaacaactga aggaagacta cttcaaaaag   2520
atagaatgtt tcgattcagt ggaaattagc ggtgttgaag acaggttcaa tgcttcattg   2580
ggtacttacc acgacctgtt gaagataatc aaagacaagg actttctcga taatgaggag   2640
aacgaagaca tcttggaaga catttgtgctt acactcactt tgtttgagga caggaaatg    2700
attgaggaaa gactcaaaac ttacgctcat ttgtttgatg ataagttat gaaacaacta    2760
aaaagaagaa ggtacaccgg ctggggaaga ttgagtagga aactgatcaa cggtattaga   2820
gataaacaat ccgaaagac tatcctcgat ttccttaaga gtgatggctt tgcaaatagg   2880
aattttatgc agctgattca tgacgactca cttaccttca agaagacat caaaaagct    2940
caggtgtctg ggcaaggcga cagtctgcat gaacatatag ctaacttggc tgggagtccc   3000
gccatcaaga aggggatact tcaaacagtt aaagttgtgg acgaattggt gaaggtaatg   3060
ggaaggcaca agcctgaaaa tatagtgata gaaatggcaa gggaaatca acaacccag     3120
aagggacaga agaacagtag ggaaaggatg aaaaggatag aagaggggat caaagagctt   3180
ggtagccaga tcctcaagga acatccagtg gagaatccc aacttcaaaa cgagaaactc    3240
tatttgtact acttgcagaa cggaagagat atgtatgtgg accaagagct tgatattaac   3300
aggctgagcg attatgacgt tgaccacata gtgccccaat cattcctcaa ggatgactct   3360
attgataata aggtgctgac aaggagtgac aagaatagag ggaaatccga caacgttcca   3420
tccgaggaag ttgtgaagaa gatgaagaac tactggaggc agttgctgaa cgctaagctc   3480
attacccaga ggaaattcga taacctgacc aaagcagaga gaggcgggct gagcgaactc   3540
gataaagcag gtttcatcaa gagacaactc gtggagacta ggcaaattac taagcacgtg   3600
gctcaaaatac tcgacagcag gatgaacaca aagtacgacg agaacgacaa gctcattaga   3660
gaggttaagg ttattactct gaaaagtaaa ttggttagcg atttcagaaa ggatttccaa   3720
ttctataagg ttagagagat caacaattat catcatgcac atgatgccta tctgaatgct   3780
gtggttggta cagcccttat caagaagtac cctaagctag agagcgagtt tgtgtacgga   3840
gattataagg tgtatgatgt gaggaaaatg atcgctaaaa gtgagcaaga gattggaaag   3900
gctaccgcca aatacttctt ttattccaat attatgaatt tcttcaagac agaaatcacc   3960
ctggctaacg gcgagataag gaagaggccg cttatcgaaa ctaatgggga gacaggcgaa   4020
atagtgtggg acaaagggag ggatttcgca actgtgagga aggttttgag catgcctcag   4080
gtgaatatcg ttaagaaaac cgaagttcaa actggagggt tctctaagga aagcattctc   4140
cccaagagga actccgacaa gctgattgct agaaagaaga actgggaccc caagaagtat   4200
ggcggattcg actcacccac tgtggcatat agccgttctcg tggtggcaaa ggttgaaaag   4260
ggtaaatcca aaaaactcaa atccgtgaag gaactccttg gcataactat tatggaaagg   4320
agtagctttg aaaagaatcc catcgacttt ctcgaagcta agggctataa ggaagttaag   4380
aaggaccta taatcaaact tccaaaatac tccctttttg agttgaaaa cggcagaaag      4440
agaatgttgg ccagtgccgg ggagcttcaa aagggcaacg aactggctct gcctagcaaa   4500
tatgtgaact ttttgtatct ggcatcacac tacgagaaac ttaaaggctc tcctgaggac   4560
aacgagcaaa aacagctctt tgttaacag cataagcact acctcgacga gattattgag    4620
cagatcagcg agttctcaaa gagagttatt ctggctgacg ctaatcttga caaggttttg   4680
tccgcttaca acaaacacag ggataagcca atcagggagc aggcagaaaa cataatccat   4740
ctctttaccc tgacaaacct cggtgccccc gctgctttca gtattttga tactaccatt    4800
gacaggaaga gatatacttc cactaaggaa gtgctcgacg caaccctcat acaccaaagt   4860
atcacaggcc tctatgaaac taggatagat ttgtctcaac ttgggggcga ttccggaggt   4920
tctgggggct ccggagggag tactaatctg atgtatataa ttgaaaagga aaccgataaa   4980
caactcgtta tccaggaatc catacttatg ttgcccgaag aggtggaaga ggttattggt   5040
aataagcctg aaagtgatat tttggttcac actgcctacg acgaatccac tgacgagaac   5100
gtgatgctgc tgacctctga cgctcccgag tataagcctt gggctctggt aattcaagac   5160
tccaacggag aaaataagat caaaatgctt tcaggggaa gtggtggttc cggcggtagt    5220
actaacctca gcgatattat tgaaggaa accggcaagc aactagttat acaagagagt     5280
attctcatgc tgcctgagga agttgaagag gttataggac acaagcccga gtctgatat     5340
ctggttcaca ctgcctatga cgaaagtaca gacgaaaacg tgatgcttct acatccgac    5400
gcacccgaat acaaacctg ggcactcgtg attcaagact ctaacgggga aaacaagatt    5460
aaaatgctcg gatctaagaa gagaagaatt aaacaagat                          5499

SEQ ID NO: 19        moltype = DNA   length = 5499
FEATURE              Location/Qualifiers
misc_feature         1..5499
                     note = base editor
source               1..5499
```

```
                    mol_type = other DNA
                    organism = synthetic construct
SEQUENCE: 19
ggatctaaga agagaagaat taaacaagat tcttccgaga ctggacccgt tgctgtggac    60
cctacactga gggaaaggat agagccccat gagtttgagg ttttctttga ccctagagaa   120
cttaggaagg agacatgcct gttgtacgag attaattggg gcggcaggca cagcatatgg   180
agacacacca gtcagaacac aaataagcac gtggaggtga acttcatcga gaaattcacc   240
accgagagat atttttgccc aaacaccaga tgttcaataa cttggttcct ttcttggagc   300
ccctgtggag agtgttccag ggcaattaca gagttcctca gtaggtatcc acacgttacc   360
cttttatct atatcgccag gctttatcac cacgctgacc caaggaatag acagggcctt    420
agggacctca tatctagcgg tgttacaatt cagataatga ctgagcaaga atctggttac   480
tgttggagaa attttgtgaa ttactcccct agcaacgagg cacactggcc aagatacccca  540
cacctctggg ttaggcttta tgttctggaa ctttactgca tcatacttgg tctacctccc   600
tgtcttaaca tcctcaggag aaagcaacct caactcacat ttttcaccat agcccttcaa   660
agctgccact atcagaggtt gccaccacat attctctggg ccactgggct gaagagtgga   720
ggctcctcag ggggaagttc tggcagcgaa acaccaggta ctagcgaaag cgccaccccc   780
gaaagcagtg gaggctcctc cggcggtagc gacaaaaagt attccatcgg gcttgctatc   840
ggaaccaact ctgtggggtg ggcagttatt accgacgaat acaaggtgcc cagcaagaag   900
tttaaggttc tggggaacac agatagacat agcataaaga aaaacctgat aggcgcactg   960
ttgttcgact ccggggaaac agccgaagct accaggctga agagaactgc aagaagaagg  1020
tacaccagaa gaaaaaacag aatatgttat ctccaagaga ttttctctaa cgagatggcc  1080
aaggtggacg actcattctt tcacagactg gaagaatctt tccttgtgga agaagataag  1140
aaacacgaga ggcaccctat ttttggcaat atcgtggatg aggtggctta ccacgaaaaa  1200
taccctacaa tataccacct caggaaaaaa ttggttgata gtacagacaa ggccgacctc  1260
aggctcatct atttggccct ggcccatatg attaaattca gggggcactt tctcatcgag  1320
ggagatttga accccgacaa cagtgatgtt gataagctct ttattcagct cgtgcagact  1380
tacaatcagt tgtttgagga aaaccccatt aatgcttccg gggtggacgc caaggcaatc  1440
ctttctgcaa gactctcaaa gtcaaggaga ctcgaaaatc tgatagcaca gcttccagga  1500
gagaagaaga acgggctctt tggaaacctg atcgctctgt cactcggact cacacccaat  1560
ttcaaaagca attttgattt ggcagaggac gctaagctgc aactcagtaa ggatacctac  1620
gacgatgact tggataatct gctcgcacaa attggggacc agtatgcaga cctgtttctc  1680
gcagctaaga acttgagtga cgccatattg ctcagtgaca tcctcagggt taataccgag  1740
attacaaaag ctccactctc tgcaagcatg atcaagaggt atgacgagca ccatcaagac  1800
ctgacactcc ttaaggcgtt ggttaggcag caacttcctg aaaagtataa ggaaatcttc  1860
ttcgatcaaa gcaaaaacgg ctacgccggc tatatagacg ggggagcatc ccaagaagaa  1920
ttttataagt tcataaaacc tatattggag aagatggacg ggacagagga attgctcgtg  1980
aaactgaaca gggaggatct cctcaggaag caaaggacct tcgacaatgg ctccatccca  2040
catcagattc acctcggcga actgcacgca atactgagaa gacaagagga ctttttatcct 2100
ttcctgaagg acaacaggga gaaaatcgag aaaatccttga cattcagaat cccatactac  2160
gttgggcctc tggccagagg taacagtagg ttcgcctgga tgactaggaa atcagaggag  2220
actattacac cctggaactt tgaagaagtt gttgataagg gagcttcagc acaatcattc  2280
atcgaaagaa tgacaaactt tgacaaaaat ctgcctaatg agaaagtgct cccaaaacat  2340
tccctgctgt atgagtattt taccgtttat aacgagctca ccaaggtgaa atacgttact  2400
gaaggtatga gaaagccagc ttttctttca ggggagcaaa agaaggctat cgtggatctt  2460
ctctttaaga ccaacagaaa ggttaccgtg aagcagctta aggaagacta ctttaaaaag  2520
atcgagtgtt tgactcagt ggaaataagc ggtgttgaag atagattcaa cgcatccttg   2580
ggaacttatc atgatcttct taagataatc aaggataaga acttctctga caacgaggaa  2640
aacgaagata tactgaggag catagttctg acacttactt tgttcgagga tagggagatg  2700
atcgaggaaa gactgaaaac atatgctcac ctttttgacg acaaagttat gaaacaactc  2760
aagagaagga gatatacagg gtgggggaga ttgagcagga aactgattaa tggtatcaga  2820
gacaaacagt caggaaaaac aatactcgac tttttgaaat cagacgggtt cgcaaatagg  2880
aatttcatgc agcttataca cgacgattca cttactttta aagaggacat tcaaaaggct  2940
caagttagtg gacaaggtga ctccctccac gaacacatcg caaatctcgc tggcagccct  3000
gcaattaaga agggtatact ccagacagtt aaggttgttg acgagctggt taaagtgatg  3060
ggaagacaca aacccgagaa catagtgata gagatgccca gggaaaacca aaccactcaa  3120
aaagggcaga aaaattccag agagaggatg aaaaggattg aagaaggtat caaggagctg  3180
ggtagccaaa ttctgaaaga acatcctgtg gaaacactc aactccagaa tgagaaactc   3240
tatctgtact atctgcaaaa tgggagagat atgtatgtgg accaggaact ggacataaac  3300
aggctctcag attacgatgt ggatcatatc gtgccacagt cctttcttaa ggatgatagc  3360
atcgacaata aggtgcttac caggtccgac aagaacaggg gaaagtcaga taacgtgcct  3420
tctgaagaag ttgttaaaaa gatgaagaac tactggagac agctgcttaa cgctaagctc  3480
ataacacaga ggaagtttga aacttgacc aaggccgaga gaggcggact ctcagaattg   3540
gataaggcag ggttcataaa aaggcagctg gtggaaacaa ggcagataac taaacatgtg  3600
gctcagatcc tcgatagtag gatgaataca aaatacgatg aaaatgaaaa tgctcataagg 3660
gaggttaaag tgataactct gaaatccaaa ctggttagcg atttttaggaa ggatttccag 3720
ttttacaaag ttagggagat caacaattat catcacgccc acgatgccta cttgaacgca  3780
gttgtgggta ctgcacttat caaaaagtac cctaagctgg aatccgagtt tgtttatgga  3840
gactataagg tgtacgacgt tagaaaaatg attgcaaagt cagacagga gatgggaaa    3900
gccactgcaa aatatttctt ttatagcaat atcatgaatt tctttaagac agaaatcaca  3960
ctggccaatg ggaaataag gaagaggccc ctgatcgaaa ctaatggcga gacagggag    4020
attgtgtggg ataaaggtag ggactttgca acagtgagga agtgctgag catgcccaa    4080
gttaatatcg ttaaaaagac cgaggttcaa acagggggct ttagtaagga aagcattttg  4140
cccaagagga atagtgacaa attgattgct aggaaaaaag attgggaccc caaaaagtat  4200
ggcggatttg atagccccac tgttgcttac tccgtgcttg tggttgcaaa ggtggagaag  4260
ggaaagagca agaaactgaa gtcagttaag gaactccttg gtatcactat catggaaaga  4320
agctcctttg agaagaaccc tattgacttc ctggaggcta agggtacaa agaggttaag   4380
aaagaccttca tcattaaatt gcccaaaatat agtctttcg agcttgaaaa cggaagaaag  4440
aggatgcttg catccgctgg cgaattgcaa aagggcaatg agcttgctct cccttccaag  4500
tatgtgaact tcctttatct tgcctcacac tatgaaaaac tcaaaggttc acccgaagac  4560
```

```
aacgaacaaa agcaactatt tgtggaacaa cacaagcact acctggacga aatcattgag   4620
caaatttctg agttttcaaa aagggtaatc ttggctgacg caaatctcga caaagttttg   4680
tcagcttaca caaacatag agataagcca attagagagc aagctgagaa tatcatccat    4740
ctgtttaccc tgactaacct tggagcgcct gctgctttta aatatttcga caccacaatc   4800
gacaggaaga ggtacactag cactaaggaa gttctcgacg ccaccctcat ccaccagagt   4860
attacaggcc tgtacgagac aagaattgat cttctcaac ttggtggtga cagcggcggt    4920
agtgggggtt caggggggcag tactaacctc agcgatataa ttgaaaagga aaccgggaaa  4980
cagcttgtta ttcaagagtc tatcctcatg ctgcccgaag aagtggagga agtgattggt   5040
aacaaacccg aatccgacat tctggttcat acagcatacg acgagtctac cgatgagaac   5100
gttatgcttc tcaccagtga tgcccctgag tacaagcctt gggccttggt aattcaagac   5160
tccaacgggg agaacaagat caagatgctt agcggtggca gtgggggaag cggcggtagt   5220
acaaatctgt ccgacatcat agaaaaggag actgggaaac aactcgtgat acaagagtct   5280
attcttatgc ttcctgaaga agttgaagaa gtgatcggta taagcccga atcagacata    5340
ctcgttcata ccgcatacga cgaatctacc gatgagaacg tgatgctcct cacatccgat   5400
gctcccgagt acaaaccttg ggctctcgtg atacaggact ctaatgggga aaataagata   5460
aaaatgcttg gatctaagaa gagaagaatt aaacaagat                          5499

SEQ ID NO: 20             moltype = DNA     length = 5499
FEATURE                   Location/Qualifiers
misc_feature              1..5499
                          note = base editor
source                    1..5499
                          mol_type = other DNA
                          organism = synthetic construct
SEQUENCE: 20
ggatctaaga agagaagaat taaacaagat agcagcgaga caggaccagt tgccgttgac   60
cctacattga gaagaagaat tgaaccccac gagtttgaag tgttttttcga tcccagggaa  120
ctcagaaaag agacttgcct cctgtatgag atcaactggg gtgggaggca cagcatctgg   180
aggcacacct cacagaacac taacaaacac gttgaagtga atttcattga gaagttcact   240
accgagaggt acttctgccc aaatacaagg tgttccatca cttggttttct ttcctggagc  300
ccatgtggtg aatgttcaag ggcaatcaca gagtttttgt caagataccc acacgttacc   360
ctctttatat atatcgcaag actgtaccac acgccgatc caaggaatag caagggcttt    420
agggaccttca tatcctccgg ggttactatc cagattatga ctgaacagga aagcgggtac  480
tgttggagga atttcgtgaa ttattcccca tcaaacgaag cacactggcc aagatacca   540
cacctgtggg tgaggcttta tgtgttggag ctatactgca tcatcctggg gctcccacct   600
tgtcttaata ttttgagaag aaaacaacca caactcacct ttttcacaat cgctctccag   660
agctgccatt atcaaaggct gccccctcac atcttgtggg ctactgggct gaaatccggg   720
ggtagctccg ggggttccag tgggtccgaa acacctggga cttcagaatc cgcaacagtt   780
gagagcaggc ggggcagcag cggcggaagt gataagaaact actcaatcgg tctggcaatc   840
ggaaccaact ctgtggggtt ggcagtgatt acagatgagt ataaggtgcc aagcaaaaaa   900
ttcaaggtgc tgggtaatac cgacagacac agcattaaga agaatttgat tggagcactc   960
ctctttgact caggggaaac agcagaggca caaggctga agaggacagc aaggcggagg   1020
tacacaaggc ggaaaaacag gatatgctac ctccaggaaa tctttagcaa cgagatggct   1080
aaagtggatg atagctttttt ccatagactc gaagaatcct ttcttgttga agaggacaaa  1140
aagcatgaaa ggcatcccat cttcggcaat atagttgatg aggttgcata ccatgagaag  1200
taccccacaa tctaccacct cagaaagaaa cttgtggact ccacagataa agcagacctg  1260
aggctcatat acctcgcact cgcacacatg ataagttca gggcacttt tctcatcgaa    1320
ggtgacctga atcagataa ttcagatgtg gataaactgt ttatacgct ggtgcaaaca   1380
tacaaccaac ttttcgagga aaacccaatc aatgcctccg tgttgatgc aaaggccatc    1440
ctgtcagcaa gactcagcaa aagcaggcgg ctcgaaaacc tcatcgccca gcttcccggt  1500
gaaaagaaga acgggctctt tggtaatctc atcgcattga gccttggtct tactccaaca  1560
ttcaagagca attttgatct ggcagaggat gctaaactgc aactctcaaa ggacacatat  1620
gacgatgacc ttgacaatct gttggcccag atcgggacc aatatgcaga cctcttcctg   1680
gccgcaagaa atctgtcaga tgcaatcctc ttgtccgaca tactgagagt taacactgag   1740
atcacaaagg caccctctgtc cgcctccatg attaagagat acgatgaaca tcaccaggat   1800
ctgactttgc tcaaagcccct cgttagacag cagttgccag aaaagtacaa agaaatattc   1860
tttgatcaat caaaaacgg atatgcaggg tacatcgacg gtgggcaag ccaggaagag    1920
ttctacaaat tcatcaaacc tatcctgaaa aagatggatg ggacagaaga gctgctggtt   1980
aagctgaata gggaagacct cctcagaaag caggacacat ttgataacgg agcatccct    2040
catcaaatcc acctcggtga actccatgct atcctgagaa ggcaggaaga ctttttatcca  2100
tttttgaagg acaatagga gaaaatcgaa aaaatcctga cattcagaat ccctatactac   2160
gttggtcctc tggcaagagg taacagtagg ttcgcatgga tgacaaggaa aagcgaggag    2220
acaatcacac cctggaattt tgaggaagtt gttgacaagg tgccagcgc acaatccttt     2280
atcgaaagaa tgcaaattt cgacaagaat ctgcctaacg aaaaggttct cccaaagcat    2340
tcactcctgt acgaatattt tacagttat aacgaactga ctaaagttaa atacgttacc   2400
gagggtatga ggaagccagc attccttttcc ggggaacaga agaaagctat tgtggacctc   2460
ctgttcaaga caaatagaaa aagtgacagtt aagcaactca agaggatta cttcaaaaag   2520
atcgaatgtt ttgactctgt ggagatcagc ggggtggagg atagattcaa cgccagcctg   2580
ggtacatatc atgatctcct gaaaatcatt aaagacaagg acttccttga caaccggaga   2640
aacgaggaca ttctggaaga cattgttctg accctcacac tctttgagga tagggagatg   2700
attgaggaaa gactgaagac ctacgcccac ctctttgacg ataaagtgat gaaacagctc   2760
aagagaagaa ggtatacagg ttgggggaga ctgagcagga agttgatcaa tgggattagg   2820
gacaaacagt ccggaaaaac aatcctcgat tttctgaagt cagacggttt cgcaaacaga   2880
aattttatgc agctcattca cgatgacagc ttgaagacat caaaaggct                2940
caagtgagcg gccaagggga tagcctccac gagcatattg caaatctggc aggttcacca   3000
gccatcaaaa agggcatact tcagacagtt aaggttgtgg acgaattggt taaagttatg   3060
ggcaggcata agcagagaa tatcgttatc gaaatggcaa gggagaacca aacaactcaa   3120
aaagggcaga aaaatagcag agagaggatg aaaagaatcg aggaagggat caaggaactt   3180
gggtcccaaa tcctcaagga gcacccagtt gaaaatactc aactgcaaaa cgagaagctc   3240
```

```
tatctctact atctccaaaa cgggagggat atgtatgttg accaggagct ggatattaac   3300
agactgtcag attatgatgt tgatcatatc gtgccccagt cattcctgaa ggacgattcc   3360
atcgacaaca aagttctcac aaggtccgat aaaaacaggg gcaagtccga taacgttcca   3420
agcgaagaag tggtgaaaaa gatgaaaaac tattggagac aacttctgaa tgcaaagttg   3480
attactcaga gaaagtttga caacctcaca aaagcagaaa gaggcgggct tagcgaactc   3540
gataaggcag ggtttatcaa agacagctg gttgagacaa ggcagatcac aaaacatgtg   3600
gcacagatcc ttgactcaag gatgaatacc aagtatgatg agaatgataa gttgatcagg   3660
gaggttaaag ttatcacact caaatccaaa ctggtgtcag acttcaggaa agactttcaa   3720
ttttataagg tgagggagat caataactac caccatgcac atgacgccta cctgaacgca   3780
gtggtgggta cagcattgat taaaaaatac cctaagctgg agtctgagtt tgtgtacggg   3840
gactacaagg tgtacgacgt gaggaaaatg atagccaagt ccgagcagga gatcgggaaa   3900
gcaacagcta agtatttctt ttacagtaat atcatgaatt tctttaaaac tgagattact   3960
ctggcaaacg gggagatcag gaaaagaccc ctcatcgaga ctaatggtga aacaggtgag   4020
atcgtttggg acaagggag ggattttgct actgttagaa aagttctgag tatgccacaa   4080
gtgaatattg tgaaaagac agaagttcag acaggtgggt tctccaaaga atccatcctg   4140
cccaagagaa attcagacaa gctcatcgca agaaagaagg actgggaccc taagaagtac   4200
ggaggatttg acagccccac cgtggcctat tccgtgcttg ttgtggcaaa ggtggagaaa   4260
gggaaagaca aaaaactgaa atccgtgaaa gaactgctgg gaattaccat catggaaaga   4320
agctcctttg agaagaaccc aatcgacttc ctggaagcaa aaggatataa ggaagtgaaa   4380
aaggacctca ttatcaagct cccaaaatac tcacttttcg agttggagaa cggtagaaag   4440
aggatgctgg caagcgcagg ggaacttcag aaaggcaatg agctggcatt gccatcaaag   4500
tatgtgaact tcctctactt ggccagccat tacgaagatc ttaaaggtag ccagaagat   4560
aacgagcaaa aacagctctt tgtggaacag cataagcatt atctggatga gatcatagaa   4620
caaatctcag agttttccaa gagagttatc ctcgcagatg caaacctgga taaggttctc   4680
tcagcctata ataagcatag agacaagcca attagagagc aagcagagaa cattatccac   4740
ttgttcactc ttacaaacct gggggcacca gccgccttca aatatttcga tacaacaata   4800
gacagaaaga ggtataccag caccaaagaa gttctcgacg ccacactgat ccatcaatca   4860
atcacaggcc tttcgaaaac taggatcgac ttgtcacaac tgggtgggga tagcggtgga   4920
tcagggggct ccggtggttc aacaaatctc tccgacataa tcgaaaaga gactggcaaa   4980
cagctcgtga tccaagagag catcctgatg ctgccagaga aggtggaaga agtgatcggt   5040
aacaaaccag agagtgacat actggttcac actgcttacg atgagagcac agatgagaac   5100
gtgatgctgc ttacaagcga tgcacctgag tacaaaccct gggctctggt tatccaagac   5160
tccaacggag agaacaagat taaaatgctg agcggtggta gcgggggtag cggcggaagc   5220
actaacctca gcgacataat cgagaaagac acaggtaaga gctcgtgat tcaggaatcc   5280
atcctcatgc tcccagagga agtggaggaa gttatcggca acaaaccaga atcagacatc   5340
ctggttcata cagcctatga cgagagcact gacgaaaatg tgatgctgct caccagcgac   5400
gcacccgagt acaaaccttg gcactcgtg atacaggatt caaatggcga aaataagatt   5460
aagatgctgg gatctaagaa gagaagaatt aaacaagat                           5499

SEQ ID NO: 21          moltype = DNA  length = 5469
FEATURE                Location/Qualifiers
misc_feature           1..5469
                       note = base editor
source                 1..5469
                       mol_type = other DNA
                       organism = synthetic construct
SEQUENCE: 21
ggatctaaga agagaagaat taaacaagat tcaagtgaga cgggcccggt cgcggtggac     60
cccacgctcc gacggcgtat cgagccccac gagttcgagg tgttttttcga cccgcgcgag   120
cttcgtaagg agacctgctt gctttacgag atcaactggg gaggacggca ctccatctgg   180
cggcacacct cgcagaacac caacaagcac gtcgaggtca actttatcga gaaattcaca   240
accgagcgct acttctgccc caacacacgg tgttcaatca catggttcct gagctggtcg   300
ccttgcggag agtgctcacg cgccatcacg gagttcctgt ctcgctaccc gcacgtcacc   360
ctctttatct atatcgcacg cctctaccac acgccgatcc gcgtaatcg ccaggggttg   420
cgcgacctaa tctcatccgg cgtaaccatt cagatcgtga ccgaacaaga atctggttac   480
tgctggagga atttcgtaaa ctactccccg tcgaacgagg cccactggcc ccgctatccc   540
cacctttggg tgcgccttta cgtgctggag ctgtactgca tcatactcgg tcttcctcct   600
tgcctgaaca tccttcggcg aaagcagccg cagttgactt tcttcaccat tgcacttcaa   660
agctgccact accagtctct ccctccacat atttctctgg cgaccggctt gaagtctggt   720
ggttcaagcg gaggctcatc tggcagcaa actccggagtc agctactcct   780
gagtctagcg gcgggtcgtc aggagggtct gacaagaaat acagtattgg ccttgcaatt   840
gggactaact ctgtgggatg ggccgtgatt acagacgagt acaaggtgcc gagcaagaag   900
tttaaggtgc ttgggaacac cgaccggcac tcgattaaga gaacctaat aggggcactt   960
ctgttcgact ccggagaaac cgcagaggcc accgccctta acgcaccgc acgacgacga   1020
tacacccggc gtaagaaccg gatctgctat ctacaggaaa tcttcagtaa tgagatggca   1080
aaggtgatga cagctttttt tcacaggctt gaggagtcgt tcctagttga ggaggacaaa   1140
aagcacgaac gccatcccat cttcgggaac atcgtggatg aggtcgccta ccacgagaag   1200
taccgacca tctaccacct ccgcaagaaa gtcgtggaca gcacagaaga ggctgacctg   1260
cgactgatct acttagccct ggcccacatg attaagttcc ggggtcactt cctaatcgag   1320
ggagacctca cccccgataa cagtgacgtg gacaagctct tcatccaact tgtgcagacc   1380
tacaaccagt tgttcgagga aaccctatc acgccagcg ggtgacgc gaaagctatc   1440
ctgtccgcca ggctgtcgaa gtctaggcgt ctggagaacc taatcgctca gctaccgggc   1500
gaaaaaaaga atgactgtt cggcaacctc atagccctga gctgggggct gacgcccaac   1560
ttcaaaagca acttcgacct ggccgaggac gccaagctcc aattgagcaa ggacacctac   1620
gacgacgact tggacaacct attgcccag ataggtgacc agtatgcaga cctcttcctt   1680
gcggccaaga acttgagtga cgctatactg ctcagtgaca tcctgaggrt gaacactgag   1740
atcactaagg cccctctctc tgcctcaatg attaagcgtt acgacgagca tcaccaggat   1800
ctcacccctg ttaaggccct tgttcggcag cagctcctg agaagtacaa ggagatattt   1860
tttgaccagt ctaagaacgg ctacgccggt tacattgacg tgggggcaag ccaggaggag   1920
```

-continued

```
ttctacaagt tcatcaagcc gatccttgag aagatggacg gcaccgagga gctacttgtc    1980
aagttgaacc gggaagacct gctccggaaa cagcgtacat tcgacaacgg cagcatccct    2040
caccagatcc acctgggcga actacacgcc atcctccgac gtcaggagga cttctatcca    2100
ttcttgaaag ataacaggga aaaatcgaa aaaatactta cgtttcgaat accttactac    2160
gtggggcccc ttgctcgggg aaactccaga ttcgcatgga tgaccaggaa gtcagaggag    2220
accatcacac cctggaactt tgaggaggtg gttgacaaag gtgcttctgc ccagtccttc    2280
attgagcgga tgactaactt cgacaagaac ctgcccaacg agaaggtgct gccaaagcac    2340
agcctgctct acgaatactt tactgtgtac aatgagctga cgaaggtgaa gtacgtgaca    2400
gagggggatgc ggaagcccgc tttcctgagc ggcgagcaaa aaaaagcaat cgtggaccta    2460
ctgttcaaga ccaaccgaaa ggtgacagtg aagcagctca aggaggacta cttcaaaaaa    2520
atcgagtgct tcgactctgt tgagataagc ggcgtggagg accgattcaa cgcctcattg    2580
ggaacctatc acgacctgct caagatcatt aaggacaagg acttcctgga taatgaggag    2640
aatgaggaca tcctggagga tattgtgctg acccttactc tattcgagga cagggagatg    2700
atcgaggagc gactcaagac ctacgctcac ctgttcgacg caaggttat gaagcaattg    2760
aagcgtaggc gatacacggg gtggggaaga ctctcccgaa aactgataaa cggcatcagg    2820
gacaagcagt cagggaagac gatcttggac ttcctgaaat ccgacgggtt cgccaaccgc    2880
aacttcatgc agctcattca cgacgactca ctaacgttca aagaggacat tcagaaggct    2940
caagtcagtg gacaaggcga ctccctgcac gagcacatta caaaccttgc gggctcccg    3000
gcgattaaaa agggcattct ccaaacggtt aaggtggtgg acgagctggt gaaggtgatg    3060
ggccgacaca agcctgagaa catcgtgatc gagatggcca gggagaacca gactacccag    3120
aagggtcaga agaactctcg ggaacgtatg aagcgtattg aggaggggat taaggagttg    3180
ggctctcaaa tcctcaagga gcaccctgtg gagaacactc agtccaaaa cggaaagctg    3240
tacctgtact acctgcaaaa cgggcgcgat atgtacgtgg atcaggagtt ggacatcaac    3300
aggcttagcg attacgacgt ggaccacatc gtgccacagt cattcttaaa ggacgacagc    3360
atcgacaaca aggttctgac gaggagcgac aagaatcgag ggaaaagtga caatgttcca    3420
tccgaggagg tggtcaagaa aatgaagaac tattggcgtc agcttctgaa cgccaagctc    3480
atcacccagc ggaaattcga caacctgact aaggctgagc gaggcggact ctccgagctt    3540
gacaaggctg gcttcatcaa gcggcagttg gtcgaaaccc gacagataac gaagcacgtt    3600
gcccagatac ttgactcccg tatgaacacc aagtacgacg agaacgacaa gctcatcagg    3660
gaggtgaagg tcattaccct taagtccaaa ctcgtcgtgg actttcgtaa ggacttccag    3720
ttctacaagg tgcgcgagat caataactac caccacgcac acgacgccta cctgaacgca    3780
gtggttggaa ccgcgttgat taaaaagtac cccaagttgg agtcggagtt cgtttacggg    3840
gactacaagg tgtacgacgt tcggaagatg atcgccaagt ctgaacagga gatcgggaaa    3900
gcaaccgcca agtatttctt ctatagcaac atcatgaact tctttaaaac cgagatcaca    3960
cttgccaatg gcgagatccg taagaggccg ctgatcgaga caaatgggga gactggcgag    4020
atcgtgtggg acaagggccg cgacttcgca accgttcgga aagtcttgtc catgcctcaa    4080
gtcaacatcg tcaagaagac tgaggtgcaa acaggcgggt tctcgaagga gtccatactg    4140
cccaagagga actcagacaa gctcatagca cgcaaaaaag actgggatcc aaagaaatac    4200
ggcgggttcg actcgccgac agtcgcatac tccgtgttag tggtggctaa agtggaaaag    4260
gggaagtcca agaagctcaa gtccgtcaag gagttgctcg ggatcaccat tatggaacgg    4320
tcctcattcg agaagaatcc cattgacttc ctagaggcga agggctacaa agaggtcaaa    4380
aaggacctaa ttattaagct ccccaagtat tcactcttcg aacttgaaaa tggtcgtaag    4440
cggatgttgg caagcgctgg agagcttcag aaggggaacg agcttgcact gccttccaag    4500
tacgtgaact tcctgtacct cgcctctcat tacgagaagt tgaagggctc accggaggac    4560
aacgagcaga agcagttgtt cgtggagcag cacaagcact acctgacga gatcattgag    4620
cagataagtg agttcagcaa acgggtgatc cttgccgacg ctaacctgga caaggtgctg    4680
agcgcctaca acaagcacag agacaagccg atccgagagc aggagaa catcatacac    4740
ctgttcaccc tcacgaacct cggggctccc gcagccttca aatattttga cacgaccatc    4800
gaccgtaaac gctacactag cacgaaggag gtgctggacg ctacccttat ccaccagtcc    4860
atcaccggcc tgtacgagac gagaatcgac ttgtcgcagc tcggtggtga ctctggcggt    4920
agtggaggaa gcggcgggag taccaacctc agcgacatta tcgagaagga gaccggcaag    4980
caactcgtga tccaggagag catactgatg ctccccgagg aggtcgagga ggtgattggc    5040
aataagcccg agtccgatat actggttcat actgcgtatg acgaaagcac agacgagaac    5100
gtcatgctac ttaccagcga cgccccggag tacaagcccg ggccctagt catccaagac    5160
agcaacggtg agaaccaagat caagatgctt accaacctga gcgacatcat tgaaaaggag    5220
accggaaagc agcttgtgat ccaggagtcc atcctaatgt tgcccgagga ggtccggagg    5280
gtcatcggaa acaagcccga gtcggacatc ctagtgcaca ccgcctacga cgaatcgacc    5340
gacgagaacg tgatgctcct cacctccgac gcacctgagt acaagccgtg ggccctcgtt    5400
atccaagact ctaatggtga gaacaagatc aagatgctcg gatctaagaa agaagaattt    5460
aaacaagat                                                           5469
```

SEQ ID NO: 22        moltype = DNA  length = 5499
FEATURE               Location/Qualifiers
misc_feature       1..5499
                      note = base editor
source                1..5499
                      mol_type = other DNA
                      organism = synthetic construct
SEQUENCE: 22

```
ggatctaaga agagaagaat taaacaagat tcgtccgaga ccggcccgt cgccgttgac     60
ccgaccctcc gccgccgcat cgagcccat gagttcgagg tgttttcga cccacgtgaa    120
ctccgcaagg aaacttgcct cctgtacgag atcaactggg gtggacgtca ctccatctgg    180
agacacacca gccagaacac gaacaagcac gtcgaggtca acttcatcga gaagttcacc    240
accgagcgct acttctgccc caacacgcgg tgctcgatca cgtggttcct gtcgctgtcc    300
ccatgcgggg agtgcagccg cgccatcacc gagttcctct cccgatacc gcacgtcacc    360
ctcttcatct acattgcccg gctctaccac acgcagacc cgcgaaaccg ccagggcctc    420
cgcgacctca tatcctccgg cgtgaccata cagatcatga ccgaacagga gtctggctac    480
tgctggcgca acttcgtgaa ctacagcccc tcgaacgagg cccactggcc gcgttacccg    540
cacttgtggg tgaggctgta cgtcctggag ttgtactgca tcatcctggg cctgcctccc    600
```

```
tgcctaaaca tcctccgccg gaagcagccc cagctcacgt tcttcacaat tgcgttgcaa    660
tcctgtcact accagcggct tccacctcac atcctctggg ctaccggcct caagagcggc    720
ggtagctccg gaggctcatc tgggagcgag acacccggca cttccgagtc tgcaaccccg    780
gagagtagtg gtggctcctc tggtggatct gacaaaaaat actcaattgg tctggcaatt    840
gggaccaaca gtgtcggatg ggccgtgatt accgacgagt acaaggtgcc gtccaaaaaa    900
ttcaaggtgc ttgggaacac cgaccgccac tcgatcaaga aaaacctaat cggtgcgttg    960
cttttcgaca gtggggagac cgccgaggca acacgcttaa aacgcacagc taggaggaga   1020
tatacacggc gcaagaaccg aatatgctac ttacaggaga tattctccaa tgagatggcg   1080
aaggtggacg actctttctt ccatcggctt gaggaatcct tcctggtcga ggaggacaaa   1140
aagcacgagc gacacccgat attcgttgaa atcgttgcta aggtggcgta ccacgagaag   1200
tacccaacga tataccactt acgcaagaag ctcgtggact ctacggacaa ggccgacttg   1260
cgccttatct acttggcact ggcccacatg attaagttcc gaggccactt ccttatcgag   1320
ggtgacctga accccgataa ctccgacgtg acaagctct catccaact cgtccagaca    1380
tacaaccagc tattcgagga gaatcctatc aacgcctctg gggtggacgc taaagctatc   1440
ctctcagccc gcctgtcaaa gtcgaggagg ttggagaacc taatcgccca gcttccaggc   1500
gagaagaaaa atgggctgtt cggaaacctt atcgcactct cactgggcct aaccccgaac   1560
ttcaagtcca acttcgacct ggcagaggac gcgaaattgc agttgtcgaa agacacctat   1620
gacgatgacc tggacaacct gttggcccag ataggggacc agtacgccga cctgttccta   1680
gcggccaaga acctgtccga cgccatcttg ctgtcggata tactgcgggt gaacaccgag   1740
atcactaaag cacctctctc cgccagcatg attaagcgtt acgacgagca ccaccaagat   1800
ttgaccctgc taaaggcact tgtacggcag cagcttcccg agaagtacaa ggagatcttt   1860
ttcgaccaaa gcaagaacgg ctacgccggg tacatcgacg gaggtgccag ccaggaggag   1920
ttctacaagt tcattaagcc catcctggag aagatgacg ggactgagga actacttgtg   1980
aagctgaacc gggaagactt actacgcaag cagcgtacct tcgacaacgg ttctatccca   2040
catcagatcc atcttgggga gttgcacgcg atcctgcgac gccaggagga ctttaccccc   2100
ttcctgaaag acaaccgcga gaaaatcgaa aagtactga ccttcagaat accttactac   2160
gtcggacccc ttgcgcgagg caactcaaga ttcgcgtgga tgaccaggaa atcagaggac   2220
accatcacac cctggaattt cgaggaggtg gttgacaagg gtgcctccgc ccagtccttt   2280
atcgaacgaa tgaccaactt cgacaagaac ttgcccaacg agaaggtgct ccccaaaacc   2340
agcctcctct acgaatattt cacagtgtac aacgagctta ctaaagttaa gtatgttact   2400
gagggcatga ggaaacccgc cttcctgtca ggcgagcaga agaaagctat tgtggacctc   2460
cttttcaaga ccaaccggaa ggtgacagtg aagcagctca aggaggacta cttcaagaag   2520
atagagtgct tcgacagcgt ggagatcagc ggggtgagg acagattcaa tgcctctctc   2580
ggaacatacc acgacttgct taagatcatc aaggacaagg acttcctcga caacgaggaa   2640
aacgaggata ttctggagga tattgttctg actcttaccc tgttcgagga ccgggagatg   2700
atcgaggagc gtctcaagac ctacgcccac ctgttcgacg acaaagttat gaagcagctc   2760
aagcgtcgga gatataccgg atggggccgt ctgtctcgga agctcatcaa cgggatcagg   2820
gacaagcagt cagggaagac gatcttagac ttccttaagt ctgacggctt cgccaacagg   2880
aacttcatgc agttgatcca cgacgacagc cttacctctca aggaggacat ccagaaggcc   2940
caagtgagtg gccagggtga cagcctccac gagcatattg ctaatcttgc gggttcccca   3000
gcgattaaaa agggcatact tcaaaccgtt aaggtggtgg acgagcttgt caaggtgatg   3060
gggcgacaca agcccgagaa catcgtgatc gagatgccca gggagaacca gaccaccag   3120
aaggggcaga agaatagccg agaacgcatg aagcgcatag aggagggat taaggagcta   3180
gggagccaga tcctcaagga acatccgtc gagaacaccc agctccagaa cgagaagcta   3240
tacctctact acttgcaaaa cgggagggat atgtacgtgg atcaggagtt ggacattaac   3300
cgcctaagcg actacgacgt agatcacatc gtgcctcagt cattcctcaa agacgacagc   3360
attgacaaaa aagtcttgac ccgatccgac aagaaccgaa gaaaatccga caatgtgccc   3420
tcagaggagg tcgtcaagaa aatgaagaac tattggaggc agctacttaa cgccaaactc   3480
ataacccagc ggaagttcga caacctgaca aaggctgagc ggggtgggct cagcgagctt   3540
gacaaggctg gcttcatcaa gcggcagttg gtggagacaa gacagataac gaagcacgtg   3600
gctcagatcc tggactctcg catgaacacg aagtacgacg agaacgacaa attgatccgc   3660
gaggtcaagg ttattacgct caagagcaaa cttgtcagcg atttccgcaa ggacttccag   3720
ttctacaagg tgagggagat taacaactac caccatgcac atgatgccta cttgaacgca   3780
gtggtgggga ccgcgcttat taaaagtac cctaagttgg agtcagagtt cgtttatggg   3840
gactacaagg tgtacgacgt ccggaagatg attgcaaagt ctgaacagga aatcgggaag   3900
gccaccgcca aatattcctt ctacagtaac attatgaatt ttttaagac tgaaattact   3960
ctcgcaaacg gcgagatcag gaagcgtccc ctcatcgaga caaacgggga gaccggggag   4020
atagtctggg acaaggggcg ggacttcgct acgtgagga aggtgctctc gatgccacaa   4080
gtgaacatcg tcaaaaagac agaggtgcag accggtggct tctcaaagga gtcaatcctg   4140
ccaaaacgta acagcgacaa gctcatcgcc cgcaagaaga actgtgaccc taagaagtat   4200
ggtgggttcg actcaccgac ggtcgcatac tccgttctgg tcgtggcaaa ggtgaaaaag   4260
ggcaagtcca aaaaactgaa atccgtgaag gagttgcttg gcattaccat catggaacgc   4320
agcagcttcg agaagaaccc cattgacttc ctggaggcta aggggtacaa ggaggtcaag   4380
aaagatttaa ttattaagct acctaagtac agcttgttcg agctggagaa cggccgaaaa   4440
cgaatgctcg catccgccgg ggaacttcaa aagggcaacg agcttgcgct gccctccaag   4500
tacgtgaact tcctgtactt ggcatcccac tacgagaaac tcaagggtag cccagaggac   4560
aacgagcaga agcagctatt cgtggagcag cacaagcact acctcgacga gataatcgag   4620
cagatcagtg agttcagtaa gcgggtgata ctcgcggacg ccaacttgga caaggtgctt   4680
agtgcctaca acaagcaccg tgacaagccc atccgagaac aagggagaag catcatccac   4740
ctttcactc tgacaaacct cggtgctccc gccgccttca aatacttcga cactaccatc   4800
gacaggaagc gctacacatc tacgaaggaa gttcttgacg ctacgcttat tcatcagtct   4860
atcacagggc tgtacgagac aaggatcgac cttagccaac tcggcgggga ttccggagga   4920
agcggcggct ccggtggttc tacaaacctg tccgacatca tcgagaagga aaccggcaag   4980
cagcttgtga tcaaggagag catactcatg ctccccgagg aggtgatcga   5040
aacaagcccg agtcagacat tctggtccac acagcctacg acgagtcaac cgacgagaac   5100
gtgatgctcc tgacaagcga cgcgcccgag tacaagccct gggcccctggt gatccaggac   5160
tcgaatgggg agaacaagat caagatgctt agtggaggct ctggagggag cggtggatca   5220
actaacctgt ctgacattat cgaaaaggag acgggcaagc agcttgtgat ccaagaatct   5280
atcctaatgt tgccggagga ggtcgaggag gtgattggaa acaagccgga aagcgacatc   5340
```

```
ctcgtccaca ccgcctatga cgagagcacg gacgagaatg tgatgctcct gacatcagac   5400
gcgccggagt acaagccgtg ggccctggtc atacaggaca gcaacgggga gaacaagatc   5460
aagatgctag gatctaagaa gagaagaatt aaacaagat                          5499

SEQ ID NO: 23           moltype = DNA   length = 3987
FEATURE                 Location/Qualifiers
misc_feature            1..3987
                        note = Cas12a polynucleotide
source                  1..3987
                        mol_type = other DNA
                        organism = synthetic construct
SEQUENCE: 23
atggccggga gcaagaagcg ccggataaag caggacacgc agttcgaggg cttcaccaac     60
ctgtaccaag tctccaagac gctccggttc gagcttatcc cgcaagggaa gaccctgaaa    120
cacatccagg aacaaggttt catcgaggag gacaaggccc gcaacgacca ctacaaggag    180
ctcaagccca taatcgatcg gatctacaag acgtacgccg accagtgcct ccaactggtg    240
cagctcgact gggagaacct gagcgccgcc attgacagct accgcaagga aaagacggag    300
gagacgcgca acgcccttat tgaggagcaa gccacctacc gcaacgccat ccacgactac    360
ttcatcgggc gcaccgacaa cctgacggac gcgatcaaca agcgccacgc ggaaatctac    420
aagggccttt tcaaggccga gctcttcaac gggaaggtcc taaaacagct cgggactgtc    480
acgacaaccg agcatgagaa cgccctcctt cgcagcttcg acaagttcac cacatacttc    540
tcgggcttct accggaaccg caagaacgtt ttcagcgcgg aggacatctc caccgccatc    600
ccgcacagga tcgtccagga caacttcccc aagttcaagg agaactgcca catcttcacg    660
cgcctgatta cagccgtacc ttcacttcgt gagcacttcg agaacgtcaa aaaggccatc    720
gggatcttcg tctccacgtc catcgaggag gtattctctt tcccgttcta taaccagctc    780
ctgacccaga cgcagatcga cctctacaac cagctactgg gcggcatcag ccgggaggcc    840
gggaccgaga aaataaaggg cctcaacgaa gttctcaacc tggccatcca gaagaacgac    900
gagaccgcgc atatcatcgc atccctgccg catcgcttca ttcctttgtt caagcagata    960
ttgagcgacc ggaacaccct ctcgttcatc ctcgaagaat tcaagagcga cgaggaggtc   1020
attcagtctt tctgcaagta caagacgctc tacggaatcg agaatgtgct ggagaccgcg   1080
gaggcactct tcaatgagct gaactccatt gacctgaccc acatcttcat tagccacaag   1140
aaactggaga cgatctccag cgccctgtgc gaccactggg acactctccg caacgccctc   1200
tacgaacgcc ggatctccga acttaccggc aagataacta agtcggctaa ggagaaggtg   1260
caacggagcc tcaagcacga ggacatcaac cttcaggaaa tcatctcagc cgcgggcaag   1320
gagctgagcg aggcgtttaa gcagaaaaca tcggagatac tgagccacgc gcacgcggcc   1380
ctggatcaac cgctgccgac gactctcaag aagcaagagg agaaggaaat ccttaagtcc   1440
cagctcgact cgctgctcgg cctctatcac ttgctcgact ggttcgcggt tgatgagtcc   1500
aacgaggtgg acccggagtt ctccgcgcgc ctcacgggta ttaagctgga gatggagcca   1560
agcttaagct tctacaacaa ggcccgcaac tacgcgacca aaaaaccgta ctcagtcgag   1620
aaattcaagc tgaatttcca gatgcctaca ttggcgaggg ggtgggacgt gaaccgcgag   1680
aagaacaatg gagccatcct gttcgtcaaa aatgggttgt actacctggg catcatgccc   1740
aagcagaagg gccgttacaa ggcccgtcaa ttcgagccta ccgagaagac ctcggagggc   1800
ttcgacaaga tgtactacga ctatttcccg gacgccgaca aatgatccc gaagtgctcc   1860
acgcagctca agccgtcac ggcccacttc cagacgcata ccacgccgat acttctgagc   1920
aacaacttca ttgagccgct agagatcacg aaggagatat cgacctaaaa caccccgaa   1980
aaggagccca agagttcca gacagcctac gctaagaaga caggtgatca aagggatat   2040
agggagcgca tctgcaagtg gatcgacttc acgcgcgagt tcctgtcgaa atatacaaag   2100
acgaccagca ttgacctaag ttctctccgc ccatcctccc agtacaagga tctgggcgag   2160
tattatgcgg agctgaaccc attgctgtac cacatcagct tccagaggat cgccgagaag   2220
gagattatgc acgcggtgga gacggggaaa ctatacctgt tccaaatata taacaaggac   2280
ttcctaaag ggcaccacgg gaagcccaac ctgcacacac tctactggac gggcttgttt   2340
tcgccagaaa atttggccaa gacttcgatc aagctcaacg gccaggcgga gttgttttac   2400
cgtcccaagt ctcgcatgaa gcgcatggcg catcgcctcg gagagaaaat gcttaacaag   2460
aagctcaagg atcagaagac gcccatacct gatacgttgt accaggaatt gtacgactac   2520
gtgaaccacc gcctatcgca cgacctctca gacgaggccc gcccctcct cccaaacgtg   2580
attactaagg aggtttccca tgaaataatc aaggaccgac ggttcaccag cgacaaattt   2640
ttttcacg tgcctatcac gctcaattac caggcggcca actccccatc gaagttcaac   2700
cagcgcgtga acgcctacct taaggagcac ccggagaccc caatcatcgg gatcgaccgt   2760
ggcgagcgga acctgatcta tattacggtg atcgatagca ccgggaagat cctggagcgg   2820
cgctccctga acacaatcca gcagtttgac taccagaaga actcgacaa ccgggagaag   2880
gagcgcgtcg cagcccggca agcatggagt gtggtcggca ccataaagga cctggaaacag   2940
ggttacctaa gtcaagttat ccacgagatc gttgacctga tgatacacta tcaagccgta   3000
gtcgtgctgg agaaccctcaa cttcgggttt aagtccaagc gcaccggcat cgcggagaag   3060
gcggtgtacc agcagttcga gaagatgctg atcgacaaag tcgaactgca ag          3120
gactaccctg cggagaaggt cggcgggggtc ttgaacccgt accagctaac cgaccagttc   3180
acgagcttcg ccaaaatggg cacgcagtcc ggattcttgt tttatgtcc ggctccatat   3240
acaagtaaga tcgacccgct gacagggttt gttgacccat cgtgtggaa gaccatcaag   3300
aaccacgaa gcaggaaaca cttcttagag ggcttcgact tcctgcatta cgacgttaag   3360
acaggcgact tcatcctgca cttcaagatg aaccgcaacc tgtcgttcca gaggggcgtg   3420
cccggcttca tgcccgcctg ggatatcgtc tttgagaaga atgagacgca gttcgacgcg   3480
aaggggacgc cgttcatcgc tggaaagcgg atcgtgccgg tcatcgagaa ccaccgcttc   3540
acgggtcgct accgagattt ataccccgcc aacgaactaa ttgcgctgct ggaggagaag   3600
gggatcgtgt tccgagatgg cagcaacatt ctccgaagc tgctggagaa cgacgactcg   3660
cacgtcatg acacgatggt cgccctcata cggacgctgc ttcagtgcg gaacagtaac   3720
gctgccacgg gcgaggacta cattaactcc cccgtccgcg acctcaacgg ggtctgcttc   3780
gatagccgct tccagaaccc ggagtggcct atggatgcgg acgcgaacgg gcctaccac   3840
atcgccctca agggccaact cctgctcaac cacttgaagg aaagcaaaga cctcaaattg   3900
cagaatggca tcagtaacca ggactggctc cgtacatcc aggaactgag aaacgggtcc   3960
aagaagcggc gtatcaagca agattga                                       3987
```

```
SEQ ID NO: 24          moltype = DNA  length = 3987
FEATURE                Location/Qualifiers
misc_feature           1..3987
                       note = Cas12a polynucleotide
source                 1..3987
                       mol_type = other DNA
                       organism = synthetic construct
SEQUENCE: 24
atggcgggaa gcaaaaagcg ccggattaag caagacacgc agttcgaggg cttcacgaac   60
ctctaccaag tcagcaagac cctccggttc gagctgatac acagggaaa gacgctcaag  120
cacatccagg aacagggctt catcgaggag acaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga agagactgag  300
gagacccgca acgccctgat cgaggagcaa gcaacctacc ggaacgccat ccacgactac  360
ttcatcggcc gcaccgacaa cctcaccgac gcgatcaaca gcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagtt tccccttcta caaccagctc  780
ctcacccaga cgcagatcga cctgtacaat cagttgctcg gcgggataag ccgcgaggcc  840
ggaaccgaaa aaatcaaggg gctgaacgaa gtgttgaacc tcgccatcca agaacgac    900
gagaccgcgc acatcatcgc ctcccgcccc accggttca tcccgctgtt caagcagatc  960
ctctctgacc ggaacaccct gtccttcatt cttgaggagt tcaagtcgga cgaggagtc 1020
atccagagct tctgcaagta caagacgctg ctacggaacg agaacgtgct ggagacggcg 1080
gaggcactgt tcaacgagct aaacagcatc gacctcacgc acatcttcat cagtcacaag 1140
aaactggaga ccatctcctc cgcgctgtgc gaccactggg acacgctcag gaacgcgctc 1200
tacgacgcc gaatcagtga gctgacgggc aagatcacga gtccgcgaa ggagaaggtg 1260
cagcggtccc tcaagcacga ggacatcaac ctccaggaga tcatctcagc ggctgggaaa 1320
gagctgtccg aggcgttcaa gcagaaaacg agcgaaatcc tgtcccacgc gcacgcggcc 1380
ctggatcagc tctgccgac gaccctcaag aaacaagaag aaaaggaaat cctcaagtcg 1440
cagctcgact cgctgctggg cctgtaccat ctcctcgact ggttcgccgt ggacgagagc 1500
aacgaggtgg accccgagtt ctccgcgcgg cttacgggga tcaagctgga gatggagccc 1560
agcctgtcct tctacaacaa ggcgcgcaac tacgccacca gaagcccta cagcgtggag 1620
aagttcaagc tcaacttcca gatgcccact ctcgcacgtg ggtgggacgt caaccgcgaa 1680
aaaaataatg gggcgatcct gttcgtcaag aacggctgt actacttggg catcatgccg 1740
aaacagggca gccgctacaa ggccctgagc ttcgaaccga ccgagaaaac gagcgagggg 1800
ttcgacaaga tgtactacga ctacttcccc gacgccgcga agatgattcc aaagtgctcc 1860
acgcagctta aggccgtgac ggcccacttc cagacgcaca cgaccccgat cctcctcagc 1920
aacaacttca tcgagcccct ggagatcacg aaggagatat acgacctgaa caacccggag 1980
aaggagccca agaaattcca gaccgcctac gccaagaaga caggcgacca aaagggttac 2040
agggaggccc tctgcaagtg gatcgacttc actagggact tcctgtccaa gtacaccaag 2100
actacctcta tcgacctgtc cagcctccgc ccgtcgtccc agtacaagga tttgggcgag 2160
tattacgcgg agctgaaccc actgctctac cacatcagct ccagcgcat cgcggagaag 2220
gagatcatgg acgcagtgga gacggcaag ctataccata ttcagatata caacaaagac 2280
ttcgctaagg gacaccacgg caagcctaac ctgcacaccc tctactggac ggggctcttc 2340
agccccggaga acctcgccaa gacctcgatc aagctcaacg gccaggcga gctgttctac 2400
cggcccaagt cccgcatgaa gcggatggc caccggctcg gggagaaaat gctcaacaag 2460
aaattgaagg accaaaaaac gccgataccc gacaccctat accaggagct gtacgactat 2520
gtgaaccacc gcctgagcca cgacctcagc gacgaggcgc gggcccttcct gccgaacgtc 2580
atcacaaagg aggtcagcca cgagatcatc aaggaccggc gcttcacctc gacaagttt 2640
ttctttcacg tgcccatcac gctcaactac caggccgcca actcgccgtc caagttcaac 2700
cagcgcgtga acgcctacct caaggagcac cccgagaccc gatcatcgg gattgaccga 2760
ggggagcgga acctcatcta catcaccgtc atcgacagca ccggaagat ccttgaacag 2820
cggtcgctca acaccatcca gcagttcgac taccagaaga aactcgacaa ccgggagaag 2880
gagagagtgc cggccccgca ggcttggtcc gtcgtcggga cgattaagga cttgaaacaa 2940
ggttacctgt cgcaagtgat ccacgagatc gttgacctga tgatccacta ccaagccgtc 3000
gtggtcctgg agaacctcaa cttcggcttc aagagcaaac gaaccggcat cgccgagaag 3060
gccgtgtacc agcagttcga aaaatgctg atcgacaagc tgaactgcct cgtgctcaag 3120
gactaccccg ctgagaaggt cggcggggtg ctgaacccgt accagctcac tgaccagttc 3180
accagcttcg caaagatggg cacccagtcc ggcttcctgt tctacgtgcc tgcgccatac 3240
acctcgaaga tcgaccgct caccgggttc gtggaacctcc tcgtctggaa gaccatcaag 3300
aaccacgaga gccgcaagca cttcctggag ggcttcgact cctccacta cgacgtcaag 3360
accgggggact tcatcctgca cttcaagatg aaccgcaacc tcagtttcca gcgcggcctg 3420
ccgggggttca tgcccgcttg ggatatagtc ttcgagaaga tgagacgca gttcgacgcg 3480
aagggcacc cgttcatcgc cgggaagcgc atcgtgccgg tcatcgagaa ccaccggttc 3540
accgggcgct accgcgacct atacccggcg aacgagttga tgcccctcct ggaggagaaa 3600
ggcatcgtgt tccgcgacgg ctccaacatc ctcccgaagc tgctcgaaaa agacgactcc 3660
cacgccatcg acacgatggt cgcgctgatc cggtcggtgc tccagatgcg gaactccaac 3720
gccgcgacgg gcgaggacta catcaacagt ccggtccgcg atctgaacgg cgtctgcttc 3780
gactccggt tccagaaccc cgagtggccg atggacgcgg acgcgaacgg cgcataccac 3840
atcgcctaa aagggcaatt gctgctcaac cacctcaagg aatcccaaaga cctaaagctc 3900
cagaacggca tctcgcaacca ggactggctg gcgtacatcc aggaactgcg gaacggggagc 3960
aaaaaacgtc ggatcaacga agcaagattga                                  3987

SEQ ID NO: 25          moltype = DNA  length = 3987
FEATURE                Location/Qualifiers
```

| misc_feature | 1..3987 |
| | note = Cas12a polynucleotide |
| source | 1..3987 |
| | mol_type = other DNA |
| | organism = synthetic construct |

SEQUENCE: 25

```
atggcgggct ccaagaaacg ccggattaag caagatacCC agttcgaggg gttcacgaac    60
ctctaccaag tgagcaagac cctccgattc gaactgattc tcaggggaa gaccctcaag    120
cacatccagg agcaagggtt catcgaggag gacaaggcgc ggaacgacca ctacaaggaa    180
ctcaaaccca tcatcgaccg catctacaag acctacgccg atcagtgcct ccagctcgtg    240
cagttggact gggagaacct cagcgcggcc attgactcct accggaagga gaaaacggag    300
gagacgcgca acgcgctcat cgaggaacag gcaacctatc gcaacgccat ccacgactac    360
ttcatcggga ggactgacaa cctcactgac gcgattaaca agcgccacgc ggagatatac    420
aagggactct tcaaagcgga gctgtttaac ggcaaggttc tcaagcaact cggcactgtg    480
accacgaccg agcatgagaa cgccctgctc cgctccttcg acaagttcac cacctacttc    540
tccgggttct accgcaaccg caagaatgtc ttcagcgcgg aggacatcag cacggccatt    600
ccacatcgaa tcgtccaaga taacttcccg aagttcaagg agaactgcca catcttcacc    660
cgactcatta ctgctgtacc gtcgttacgc gaacacttcg agaacgtcaa gaaggcaatt    720
ggaatcttcg tctctacgtc aatagaggag gtgttcagct ccctttcta caaccagctc    780
cttacgcaga cccagataga cctgtacaat cagctcctcg gtgggatcag ccggaggcg    840
gggactgaga agattaaagg gctcaacgag gtcttgaacc tggccatcca aaaaaacgat    900
gagacggcgc acatcatcgc ctcgctgccc caccggttca tcccgctgtt caagcagatc    960
ctcagtgaca ggaacacctt gagctttatc ctagaggagt tcaagagcga cgaggaggtg   1020
atccagagct tctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactgga cacccctccg caacgcgtca   1200
tacgagcgcc gcatctcgga gctgaccggg aagatcacca atccgcgaa ggaaaaggtc   1260
cagcgttccc tcaaacacga ggatattaac ttacaggaga ttatctcagc ggctgggaag   1320
gagttgtcag aggcgttcaa gcagaaaact tccgagatcc tgagccacgc gcacgcagcg   1380
ctcgaccagc ctctgcccac caccctcaaa aagcaggaag aaaaagagat cctcaagagc   1440
cagttggact ccctgctggg gctctatcac cttctcgact ggttcgccgt cgatgagtcg   1500
aacgaggtgg accccgagtt ctccgcccgg ctgaccggca tcaagctaga gatggagccg   1560
tccctcagct tctacaataa ggccgcaac tacgcgacca aaaaaccta cagcgtggag   1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggcccttttcc ttcgagccga cggagaaaac ctccgagggg   1800
ttcgacaaga tgtactacga ctacttcccc gacgccgcca agatgatccc gaagtgctca   1860
acgcagctaa agccgtgac cgcccacttc cagacccaca cgaccgcgat cctgctgagc   1920
aacaacttca tcgagcccct tgagatcact aaggagatat acgacctgaa caacccgag   1980
aaggagccca agaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgagc agcttaatcc actactctac cacatctcat tccagcgcat cgctgagaag   2220
gaaatcatgg acgcggtgga gacaggcaaa ctgtacctct tccagatata caacaaagac   2280
ttcgctaagg gcaccacgg gaagcccaac cttcatcgc tctactggac gggcctattc   2340
agccccgaaa atctggccaa gacctccatc aagctgaacg ccaagcgga gctgttctac   2400
agacccaaga gccggatgaa gcggatggcc cacaggctcg gcgagaaaat gcttaacaaa   2460
aagttgaagg accagaaaac ccctatcccc gacaccctct accaggaact gtacgactac   2520
gtgaaccaca ggctctcgca cgaccttttcc gacgaggccc gtgccctact cccgaacgtc   2580
attaccaaaa aggtttcgca cgagatcatc aaggaccggc ggttcacgag cgacaagttt   2640
ttctttcacg tccccatcac ccttaactac caggcggcca actccccatc caagttcaac   2700
cagcgtgtga atgcctacct caaggagcac ccagagaccc cgatcattgg gatcgaccgg   2760
ggcgagcgga acctgatcta catcaccgtc atcgactcga cggcgcaagat tcttgagcag   2820
agatcgttga ataccataca gcagttcgac taccagaaga aactcgacaa ccgcgagaag   2880
gagcgcgtgg cggcccgcca ggcgtggtcc gtcgttggga cgattaagga cttgaaacaa   2940
ggttatctgt cccaagtcat ccacgagatc gttgatctga tgatccacta tcaggcagtg   3000
gtggtgctgg agaatctcaa cttcggcttc aagagtaagc ggacgggaat cgccgagaag   3060
gccgtgtacc agcagttcga gaagatgctg atcgacaagc tcaactgcct tgtgctgaaa   3120
gactacccgg ccgagaaggt cggcggcgtc ctcaaccgt accaacttac cgaccagttc   3180
acctccttcg ccaagatggg cactcagtcc gggttcttgt tctacgtccc cgcaccttac   3240
acctctaaga tcgaccctct gactggcttc gtagatccat tcgtgtggaa gaccattaag   3300
aaccacgaga gccgcaagca cttcctggag ggcttcgact tcctgcacta cgacgtgaag   3360
accggggact tcatccttca cttcaagatg aaccggaacc tcagcttcca gcggggcctg   3420
ccggggttca tgcccgcctg ggacatcgtt ttcgagaaga ggaaccagcc gttcgacgtg   3480
aagggcacgc ccttcatcgc cgggaagcgt atcgtgccgg tgatcgagaa ccatcgttc   3540
acgggtcgct accgtgacct ctaccgcgcg aacgagctta tcgcactcct ggaggagaag   3600
ggcatcgtct tccgggacgg ctccaacatc ctcccgaaac tgctgaaaa cgacgactct   3660
cacgccatcg acacgatggt ggccctcatc cggtccgtgc tccaaatgcg gaacagcaac   3720
gccgccaccg gtgaggacta catcaacagc ccggtccggg atctgaacgg ggtgtccttc   3780
gattcgcggt tccagaatcc tgagtggccc atggacgcgg atgcaaacgg ggcgtaccac   3840
atcgcgctca agggccagtt acttctgaac cacttaaggg agtctaaaga tttgaaactc   3900
cagaacggga tctcgaacca ggactggctg gcctacatcc aagagttgcg gaacggcagc   3960
aagaagcggc ggattaagca agattag                                      3987
```

| SEQ ID NO: 26 | moltype = AA length = 1228 |
| FEATURE | Location/Qualifiers |
| REGION | 1..1228 |
| | note = Lachnospiraceae bacterium |
| source | 1..1228 |

```
                        mol_type = protein
                        organism = unidentified
SEQUENCE: 26
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IPGEWNIVRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 27           moltype = AA   length = 1307
FEATURE                 Location/Qualifiers
source                  1..1307
                        mol_type = protein
                        organism = Acidaminococcus sp.
SEQUENCE: 27
MTQFEGFTNL YQVSKTLRFE LIPQGKTLKH IQEQGFIEED KARNDHYKEL KPIIDRIYKT    60
YADQCLQLVQ LDWENLSAAI DSYRKEKTEE TRNALIEEQA TYRNAIHDYF IGRTDNLTDA   120
INKRHAEIYK GLFKAELFNG KVLKQLGTVT TTEHENALFR SFDKFTTYFS GFYENRKNVF   180
SAEDISTAIP HRIVQDNFPK FKENCHIFTR LITAVPSLRE HFENVKKAIG IFVSTSIEEV   240
FSFPFYNQLL TQTQIDLYNQ LLGGISREAG TEKIKGLNEV LNLAIQKNDE TAHIIASLPH   300
RFIPLFKQIL SDRNTLSFIL EEFKSDEEVI QSFCKYKTLL RNENVLETAE ALFNELNSID   360
LTHIFISHKK LETISSALCD HWDTLRNALY ERRISELTGK ITKSAKEKVQ RSLKHEDINL   420
QEIISAAGKE LSEAFKQKTS EILSHAHAAL DQPLPTTLKK QEEKEILKSQ LDSLLGLYHL   480
LDWFAVDESN EVDPEFSARL TGIKLEMEPS LSFYNKARNY ATKKPYSVEK FKLNFQMPTL   540
ASGWDVNKEK NNGAILFVKN GLYYLGIMPK QKGRYKALSF EPTEKTSEGF DKMYYDYFPD   600
AAKMIPKCST QLKAVTAHFQ THTTPILLSN NFIEPLEITK EIYDLNNPEK EPKKFQTAYA   660
KKTGDQKGYR EALCKWIDFT RDFLSKYTKT TSIDLSSLRP SSQYKDLGEY YAELNPLLYH   720
ISFQRIAEKE IMDAVETGKL YLFQIYNKDF AKGHHGKPNL HTLYWTGLFS PENLAKTSIK   780
LNGQAELFYR PKSRMKRMAH RLGEKMLNKK LKDQKTPIPD TLYQELYDYV NHRLSHDLSD   840
EARALLPNVI TKEVSHEIIK DRRFTSDKFF FHVPITLNYQ AANSPSKFNQ RVNAYLKEHP   900
ETPIIGIDRG ERNLIYITVI DSTGKILEQR SLNTIQQFDY QGKLDNREKE RVAARQAWSV   960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 28           moltype = AA   length = 1241
FEATURE                 Location/Qualifiers
source                  1..1241
                        mol_type = protein
                        organism = Butyrivibrio proteoclasticus
SEQUENCE: 28
MLLYENYTKR NQITKSLRLE LRPQGKTLRN IKELNLLEQD KAIYALLERL KPVIDEGIKD    60
IARDTLKNCE LSFEKLYEHF LSGDKKAYAK ESERLKKEIV KTLIKNLPEG IGKISEINSA   120
KYLNGVLYDF IDKTHKDSEE KQNILSDILE TKGYLALFSK FLTSRITTLE QSMPKRVIEN   180
FEIYAANIPK MQDALERGAV SFAIEYESIC SVDDYYNQILS QEDIDSYNRL ISGIMDEDGA   240
KEKGINQTIS EKNIKIKSEH LEEKPFRILK QLHKQILEER EKAFTIDHID SDEEVVQVTK   300
EAFEQTKEQW ENIKKINGFY AKDPGDITLF IVVGPNQTHV LSQLIYGEHD RIRLLLEEYE   360
KNTLEVLPRR TKSEDARYDK FVNAVPKKVA KESHTFDGLQ KMTGDDRLFI LYRDELARNY   420
MRIKEAYGTF ERDILKSRRG IKGNRDVQES LVSFYDELTK FRSALRIINS GNDEKADPIF   480
YNTFDGIFEK ANRTYKAENL CRNYVTKSPA DDARIMASCL GTPARLRTHW WNGEENFAIN   540
DVAMIRRGDE YYYFVLTPDV KPVDLKTKDE TDAQIFVQRK GAKSFLGLPK ALFKCILEPY   600
FESPEHKNDK NCVIEEYVSK PLTIDRRAYD IFKNGTFKKT NIGIDGLTEE KFKDDCRYLI   660
DVYKEFIAVY TRYSCFNMSG LKRADEYNDI GEFFSDVDTR LCTMEWIPVS FERINDMVDK   720
KEGLLFLVRS MFLYNRPRKP YERTFIQLFS DSNMEHTSML LNSRAMIQYR AASLPRRVTH   780
KKGSILVALR DSNGEHIPMH IREAIYKMKN NFDISSEDFI MAKAYLAEHD VAIKKANEDI   840
IRNRRYTEDK FFLSLSYTKN ADISARTLDY INDKVEEDTQ DSRMAVIVTR NLKDLTYVAV   900
VDEKNNVLEE KSLNEIDGVN YRELLKERTK IKYHDKTRLW QYDVSSKGLK EAYVELAVTQ   960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
```

```
LLEDKAVFDG NMAEKFLDKT AISGKSVELI YKWFANALYG IITKKDGEKI YRSPITGTEI   1200
DVSKNTTYNF GKKFMFKQEY RGDGDFLDAF LNYMQAQDIA V                      1241

SEQ ID NO: 29              moltype = AA  length = 1238
FEATURE                    Location/Qualifiers
source                     1..1238
                           mol_type = protein
                           organism = Candidatus Methanoplasma termitum
SEQUENCE: 29
MNNYDEFTKL YPIQKTIRFE LKPQGRTMEH LETFNFFEED RDRAEKYKIL KEAIDEYHKK    60
FIDEHLTNMS LDWNSLKQIS EKYYKSREEK DKKVFLSEQK RMRQEIVSEF KKDDRFKDLF   120
SKKLFSELLK EEIYKKGNHQ EIDALKSFDK FSGYFIGLHE NRKNMYSDGD EITAISNRIV   180
NENFPKFLDN LQKYQEARKK YPEWIIKAES ALVAHNIKMD IVFSLEYFNK VLNQEGIQRY   240
NLALGGYVTK SGEKMMGLND ALNLAHQSEK SSKGRIHMTP LFKQILSEKE SFSYIPDVFT   300
EDSQLLPSIG GFFAQIENDK DGNIFDRALE LISSYAEYDT ERIYIRQADI NRVSNVIFGE   360
WGTLGGLMRE YKADSINDIN LERTCKKVDK WLDSKEFALS DVLEAIDRTG NNDAFNEYIS   420
KMRTAREKID AARKEMKFIS EKISGDEESI HIIKTLLDSV QQFLHFFNLF KARQDIPLDG   480
AFYAEFDEVH SKLFAIVPLY NKVRNYLTKN NLNTKKIKLN FKNPTLANGW DQNKVYDYAS   540
LIFLRDGNYY LGIINPKRKK NIKFEQSGSN GPFYRKMVYK QIPGPNKNLR PVFLTSTKGK   600
KEYKPSKEII EGYEADKHIR GDKFDLDFCH KLIDFFKESI EKHKDWSKFN FYFSPTESYG   660
DISEFYLDVE KQGYRMHFEN ISAETIDEYV EKGDLFLFQI YNKDFVKAAT GKKDMHTIYW   720
NAAFSPENLQ DVVVKLNGEA ELFYRDKSDI KEIVHREGEI LVNRTYNGRT PVPDKIHKKL   780
TDYHNGRTKD LGEAKEYLDK VRYFKAHYDI TKDRRYLNDK IYFHVPLTLN FKANGKKNLN   840
KMVIEKPLSD EKAHIIGIDR GERNLLYYSI IDRSGKIIDQ QSLNVIDGFD YREKLNQREI   900
EMKDARQSWN AIGKIKDLKE GYLSKAVHEI TKMAIQYNAI VVMEELNYGF KRGRFKVEKQ   960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                         1238

SEQ ID NO: 30              moltype = AA  length = 1281
FEATURE                    Location/Qualifiers
source                     1..1281
                           mol_type = protein
                           organism = Eubacterium eligens
SEQUENCE: 30
MNGNRSIVYR EFVGVIPVAK TLRNELRPVG HTQEHIIQNG LIQEDELRQE KSTELKNIMD    60
DYYREYIDKS LSGVTDLDFT LLFELMNLVQ SSPSKDNKKA LEKEQSKMRE QICTHLQSDS   120
NYKNIFNAKL LKEILPDFIK NYNQYDVKDK AGKLETLALF NGFSTYFTDF FEKRKNVFTK   180
EAVSTSIAYR IVHENSLIFL ANMTSYKKIS EKALDEIEVI EKNNQDKMGD WELNQIFNPD   240
FYNMVLIQSG IDFYNEICGV VNAHMNLYCQ QTKNNYNLFK MRKLHKQILA YTSTSFEVPK   300
MFEDDMSVYN AVNAFIDETE KGNIIGKLKD IVNKYKSIN DVNDLVEKYI DEKERNEFKN   360
WNLITGCVEN FYDENIHAKG KSKEEKVKKA VKEDKYKSIN DVNDLVEKYI DEKERNEFKN   420
SNAKQYIREI SNIITDTETA HLEYDDHISL IESEEKADEM KKRLDMYMNM YHWAKAFIVD   480
EVLDRDEMFY SDIDDIYNIL ENIVPLYNRV RNYVTQKPYN SKKIKLNFQS PTLANGWSQS   540
KEFDNNAIIL IRDNKYYLAI FNAKNKPDKK IIQGNSDKVN DNDYKKMVYN LLPGANKMLP   600
KVFLSKKGIE TFKPSDYIIS GYNAHKHIKT SENFDISFCR DLIDYFKNSI EKHAEWRKYE   660
FKFSATDSYS DISEFYREVE MQGYRIDWTY ISEADINKLD EEGYKYLFQI YNKDFAENST   720
GKENLHTMYF KNIFSEENLD KIIKLNGQAE LFYRRASVKN PVKHKKDSVL VNKTYKNQLD   780
NGDVVRIPIP DDIYNEIYKM YNGYIKESDL SEAAKEYLDK VEVRTAQKDI VKDYRYTVDK   840
YFIHTPITIN YKVTARNNVN DMVVKYIAQN DDIHVIGIDR GERNLIYISV IDSHGNIVKQ   900
KSYNILNNYD YKKKLVEKEK TREYARKNWK SIGNIKELKE GYISGVVHEI AMLIVEYNAI   960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSSIT NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                           1281

SEQ ID NO: 31              moltype = AA  length = 1300
FEATURE                    Location/Qualifiers
source                     1..1300
                           mol_type = protein
                           organism = Francisella novicida
SEQUENCE: 31
MSIYQEFVNK YSLSKTLRFE LIPQGKTLEN IKARGLILDD EKRAKDYKKA KQIIDKYHQF    60
FIEEILSSVC ISEDLLQNYS DVYFKLKKSD DDNLQKDFKS AKDTIKKQIS EYIKDSEKFK   120
NLFNQNLIDA KKGQESDLIL WLKQSKDNGI ELFKANSDIT DIDEALEIIK SFKGWTTYFK   180
GFHENRKVNY SSNDIPTSII YRIVDDNLPK FLENKAKYES LKDKAPEAIN YEQIKKDLAE   240
ELTFDIDYKT SEVNQRVFSL DEVFEIANFN NYLNQSGITK FNTIIGGKFV NGENTKRKGI   300
NEYINLYSQQ INDKTLKKYK MSVLFKQILS DTESKSFVID KLEDDSDVVT TMQSFYEQIA   360
APKTVEEKSI KETLSLLFDD LKAQKLDLSK IYFKNDKSLT DLSQQVFDDY SVIGTAVLEY   420
ITQQIAPKNL DNPSKKEQEL IAKKTEKAKY LSLETIKLAL EEFNKHRDID KQCRFEEILA   480
NFAAIPMIFD EIAQNKDNLA QISIKYQNQG KKDLLQASAE DDVKAIKDLL DQTNNLLHKL   540
KIFHISQSED KANILDKDEH FYLVFEECYF ELANIVPLYN KIRNYITQKP YSDEKFKLNF   600
ENSTLANGWD KNKEPDNTAI LFIKDDKYYL GVMNKKNNKI FDDKAIKENK GEGYKKIVYK   660
LLPGANKMLP KVFFSAKSIK FYNPSEDILR IRNHSTHTKN GSPQKGYEKF EFNIEDCRKF   720
IDFYKQSISK HPEWKDFGFR FSDTQRYNSI DEFYREVENQ GYKLTFENIS ESYIDSVVNQ   780
```

```
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLLEKAND VHILSIDRGE RHLAYYTLVD GKGNIIKQDT FNIIGNDRMK TNYHDKLAAI    960
EKDRDSARKD WKKINNIKEM KEGYLSQVVH EIAKLVIEYN AIVVFEDLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDADANGAY   1260
HIGLKGLMLL GRIKNNQEGK KLNLVIKNEE YFEFVQNRNN                         1300

SEQ ID NO: 32           moltype = AA  length = 1206
FEATURE                 Location/Qualifiers
REGION                  1..1206
                        note = Lachnospiraceae bacterium
source                  1..1206
                        mol_type = protein
                        organism = unidentified
SEQUENCE: 32
MYYESLTKQY PVSKTIRNEL IPIGKTLDNI RQNNILESDV KRKQNYEHVK GILDEYHKQL     60
INEALDNCTL PSLKIAAEIY LKNQKEVSDR EDFNKTQDLL RKEVVEKLKA HENFTKIGKK    120
DILDLLEKLP SISEDDYNAL ESFRNFYTYF TSYNKVRENL YSDKEKSSTV AYRLINENFP    180
KFLDNVKSYR FVKTAGILAD GLGEEEQDSL FIVETFNKTL TQDGIDTYNS QVGKINSSIN    240
LYNQKNQKAN GFRKIPKMKM LYKQILSDRE ESFIDEFQSD EVLIDNVESY GSVLIESLKS    300
SKVSAFFDAL RESKGKNVYV KNDLAKTAMS VIVFENWRTF DDLLNQEYDL ANENKKKDDK    360
YPFEKRQELK KNKSYSLEHL CNLSEDSCNL IENYIHQISD DIENIIINNE TFLRIVINEH    420
DRSRKLAKNR KAVKAIKDFL DSIKVLEREL KLINSSGQEL KDLIVYSAH EELLVELKQV     480
DSLYNMTRNY LTKKPFSTEK VKLNFNRSTL LNGWDRNKET DNLGVLLLKD GKYYLGIMNT    540
SANKAFVNPP VAKTEKVFKK VDYKLLPVPN QMLPKVFFAK SNIDFYNPSS EIYSNYKKGT    600
HKKGNMFSLE DCHNLIDFFK ESISKHEDWS KFGFKFDTQA SYNDISEFYR EVEKQGYKLT    660
YTDIDETYIN DLIERNELYL FQIYNKDFSM YSKGKLNLFT LYPMMLFDQR NIDDVVYKLN    720
GEAEVFYRPA SISEDELIIH KAGEEEIKNKN PNRARTKETS TFSYDIVKDK RYSKDKFTLH   780
IPITMNFGVD EVKRFNDAVN SAIRIDENVN VIGIDRGERN LLYVVIDSK GNILEQISLN     840
SIINKEYDIE TDYHALLDER EGGRDKARKD WNTVENIRDL KAGLYLQVVN VVAKLVLKYN    900
AIICLEDLNF GFKRGRQKVE KQVYQKFEKM LIDKLNYLVI DKSREQTSPK ELGGALNALQ    960
LTSKFKSFKE LGKQSGVIYY VPAYLTSKID PTTGFANLFY MKCENVEKSK RFFDGFDFIR   1020
FNALENVFEF GFDYRSFTQR ACGINSKWTV CTNGERIIKY RNPDKNNMFD EKVVVVTDEM   1080
KNLFEQYKIP YEDGRNVKDM IISNEEAEFY RRLYRLLQQT LQMRNSTSDG TRDYIISPVK   1140
NKREAYFNSE LSDGSVPKDA DANGAYNIAR KGLWVLEQIR QKSEGEKINL AMTNAEWLEY   1200
AQTHLL                                                              1206

SEQ ID NO: 33           moltype = AA  length = 1233
FEATURE                 Location/Qualifiers
REGION                  1..1233
                        note = Lachnospiraceae bacterium
source                  1..1233
                        mol_type = protein
                        organism = unidentified
SEQUENCE: 33
MDYGNGQFER RAPLTKTITL RLKPIGETRE TIREQKLLEQ DAAFRKLVET VTPIVDDCIR     60
KIADNALCHF GTEYDFSCLG NAISKNDSKA IKKETEVEK LLAKVLTENL PDGLRKVNDI     120
NSAAFIQDTL TSFVQDDADK RVLIQELKGK TVLMQRFLTT RITALTVWLP DRVFENFNIF    180
IENAEKMRIL LDSPLNEKIM KFDPDAEQYA SLEFYGQCLS QKDIDSYNLI ISGIYADDEV    240
KNPGINEIVK EYNQQIRGDK DESPLPKLKK LHKQILMPVE KAFFVRVLSN DSDARSILEK    300
ILKDTEMLPS KIIEAMKEAD AGDIAVYGSR LHELSHVIYG DHGKLSQIIY DKESKRISEL    360
METLSPKERK ESKKRLEGLE EHIRKSTYTF DELNRYEAKN VMAAYIAAVE ESCAEIMRKE    420
KDLRTLLSKE DVKIRGNRHN TLIVKNYFNA WTVFRNLIRI LRRKSEAEID SDFYDVLDDS    480
VEVLSLTYKG ENLCRSYITK KIGSDLKPEI ATYGSALRPN SRWWSPGEKF NVKFHTIVRR    540
DGRLYYFILP KGAKPVELED MDGDIECLQM RKIPNPTIFL PKLVFKDPEA FFRDNPEADE    600
FVFLSGMKAP VTITRETYEA YRYKLYTVGK LRDGEVSEEE YKRALLQVLT AYKEFLENRM    660
IYADLNFGFK DLEEYKDSSE FIKQVETHNT FMCWAKVSSS QLDDLVKSGN GLLFEIWSER    720
LESYYKYGNE KVLRGYEGVL LSILKDENLV SMRTLLNSRP MLVYRPKESS KPMVVHRDGS    780
RVVDRFDKDG KYIPPEVHDE LYRFFNNLLI KEKLGEKARK ILDNKKVVK VLESERVKWS     840
KFYDEQFAVT FSVKKNADCL DTTKDLNAEV MEQYSESNRL ILIRNTTDIL YYLVLDKGN     900
VLKQRSLNII NDGARDVDWK ERFRQVTKDR NEGYNEWDYS RTSNDLKEVY LNYALKEIAE    960
AVIEYNAILI IEKMSNAFKD KYSFLDDVTF KGFETKKLAK LSDLHFRGIK DGEPCSFTNP   1020
LQLCQNDSNK ILQDGVIFMV PNSMTRSLDP DTGFIFAIND HNIRTKKAKL NFLSKFDQLK   1080
VSSEGCLIMK YSGDSLPTHN TDNRVWNCCC NHPITNYDRE TKKVEFIEEP VEELSRVLEE   1140
NGIETDTELN KLNERENVPG KVVDAIYSLV LNYLRGTVSG VAGQRAVYYS PVTGKKYDIS   1200
FIQAMNLNRK CDYYRIGSKE RGEWTDFVAQ LIN                                1233

SEQ ID NO: 34           moltype = AA  length = 1227
FEATURE                 Location/Qualifiers
REGION                  1..1227
                        note = Lachnospiraceae bacterium
source                  1..1227
                        mol_type = protein
                        organism = unidentified
SEQUENCE: 34
MSKLEKFTNC YSLSKTLRFK AIPVGKTQEN IDNKRLLVED EKRAEDYKGV KKLLDRYYLS     60
```

```
FINDVLHSIK LKNLNNYISL FRKKTRTEKE NKELENLEIN LRKEIAKAFK GNEGYKSLFK      120
KDIIETILPE FLDDKDEIAL VNSFNGFTTA FTGFFDNREN MFSEEAKSTS IAFRCINENL      180
TRYISNMDIF EKVDAIFDKH EVQEIKEKIL NSDYDVEDFF EGEFFNFVLT QEGIDVYNAI      240
IGGFVTESGE KIKGLNEYIN LYNQKTKQKL PKFKPLYKQV LSDRESLSFY GEGYTSDEEV      300
LEVFRNTLNK NSEIFSSIKK LEKLFKNFDE YSSAGIFVKN GPAISTISKD IPGEWNVIRD      360
KWNAEYDDIH LKKKAVVTEK YEDDRRKSFK KIGSFSLEQL QEYADADLSV VEKLKEIIIQ      420
KVDEIYKVYG SSEKLFDADF VLEKSLKKND AVVAIMKDLL DSVKSFENYI KAFFGEGKET      480
NRDESFYGDF VLAYDILLKV DHIYDAIRNY VTQKPYSKDK FKLYFQNPQF MGGWDKDKET      540
DYRATILRYG SKYYLAIMDK KYAKCLQKID KDDVNGNYEK INYKLLPGPN KMLPKVFFSK      600
KWMAYYNPSE DIQKIYKNGT FKKGDMFNLN DCHKLIDFFK DSISRYPKWS NAYDFNFSET      660
EKYKDIAGFY REVEEQGYKV SFESASKKEV DKLVEEGKLY MFQIYNKDFS DKSHGTPNLH      720
TMYFKLLFDE NNHGQIRLSG GAELFMRRAS LKKEELVVHP ANSPIANKNP DNPKKTTTLS      780
YDVYKDKRFS EDQYELHIPI ANINKCPKNI FKINTEVRVL LKHDDNPYVI GIDRGERNLL      840
YIVVVDGKGN IVEQYSLNEI INNFNGIRIK TDYHSLLDKK EKERFEARQN WTSIENIKEL      900
KAGYISQVVH KICELVEKYD AVIALEDLNS GFKNSRVKVE KQVYQKFEKM LIDKLNYMVD      960
KKSNPCATGG ALKGYQITNK FESFKSMSTQ NGFIFYIPAW LTSKIDPSTG FVNLLKTKYT     1020
SIADKKFISS FDRIMYVPEE DLFEFALDYK NFSRTDADYI KKWKLYSYGN RIRIFRNPKK     1080
NNVFDWEEVC LTSAYKELFN KYGINYQQGD IRALLCEQSD KAFYSSFMAL MSLMLQMRNS     1140
ITGRTDVDFL ISPVKNSDGI FYDSRNYEAQ ENAILPKNAD ANGAYNIARK VLWAIGQFKK     1200
AEDEKLDKVK IASNKEWLEY AQTSVKH                                        1227

SEQ ID NO: 35           moltype = AA  length = 1264
FEATURE                 Location/Qualifiers
source                  1..1264
                        mol_type = protein
                        organism = Leptospira inadai
SEQUENCE: 35
MEDYSGFVNI YSIQKTLRFE LKPVGKTLEH IEKKGFLKKD KIRAEDYKAV KKIIDKYHRA       60
YIEEVFDSVL HQKKKKDKTR FSTQFIKEIK EFSELYYKTE KNIPDKERLE ALSEKLRKML      120
VGAFKGEFSE EVAEKYNKNL FSKELIRNEI EKFCETEDER KQVSNFKSFT TYFTGFHSNR      180
QNIYSDEKKS TAIGYRIIHQ NLPKFLDNLK IIESIQRRFK DFPWSDLKKN LKKIDKNIKL      240
TEYFSIDGFV NVLNQKGIDA YNTILGGKSE ESGEKIQGLN EYINLYRQKN NIDRKNPLNV      300
KILFKQILGD RETKSFIPEA FPDDQSVLNS ITEFAKYLKL DKKKKSIIAE LKKFLSSFNR      360
YELDGIYLAN DNSLASISTF LFDDWSFIKK SVSFKYDESV GDPKKKIKSP LKYEKEKEKW      420
LKQKYYTISF LNDAIESYSK SQDEKRVKIR LEAYFAEFKS KDDAKKQFDL LERIEEAYAI      480
VEPLLGAEYP RDRNLKADKK EVGKIKDFLD SIKSLQFFLK PLLSAEIFDE KDLGFYNQLE      540
GYYEEIDISG HLYNKVRNYL TGKIYSKEKF KLNFENSTLL KGWDENREVA NLCVIFREDQ      600
KYYLGVMDKE NNTILSGDIPK VKPNELFYEK MVYKLIPTPH MQLPRIIFSS DNLSIYNPSK      660
SILKIREAKS FKEGKNFKLK DCHKFIDFYK ESISKNEDWS RFDFKFSKTS SYENISEFYR      720
EVERQGYNLD FKKVSKFYID SLVEDGKLYL FQIYNKDFSI FSKGKPNLHT IYFRSLFSKE      780
NLKDVCLKLN GEAEMFFRKK SINYDEKKKR EGHHPELFEK LKYPILKDKR YSEDKFQFHL      840
PISLNFKSKE RLNFNLKVNE FLKRNKDINI IGIDRGERNL LYLVMINQKG EILKQTLLDS      900
MQSGKGRPEI NYKEKLQEKE IERDKARKSW GTVENIKELK EGYLSIVIHQ ISKLMVENNA      960
IVVLEDLNIG FKRGRQKVER QVYQKFEKML IDKLNFLVFK ENKPTEPGGV LKAYQLTDEF     1020
QSFEKLSKQT GFLFYVPSWN TSKIDPRTGF IDFLHPAYEN IEKAKQWINK FDSIRFNSKM     1080
DWFEFTADTR KFSENLMLGK NRVWVICTTN VERYFTSKTA NSSIQYNSIQ ITEKLKELFV     1140
DIPFSNGQDL KPEILRKNDA VFFKSLLFYI KTTLSLRQNN GKKGEEEKDF ILSPVVDSKG     1200
RFFNSLEASD DEPKDADANG AYHIALKGLM NLLVLNETKE ENLSRPKWKI KNKDWLEFVW     1260
ERNR                                                                 1264

SEQ ID NO: 36           moltype = AA  length = 1373
FEATURE                 Location/Qualifiers
source                  1..1373
                        mol_type = protein
                        organism = Moraxella bovoculi
SEQUENCE: 36
MLFQDFTHLY PLSKTVRFEL FIDRTLEHIH AKNFLSQDET MADMHQKVKV ILDDYHRDFI       60
ADMMGEVKLT KLAEFYDVYL KFRKNPKDDE LQKAQLKDLQ AVLRKEIVKP IGNGGKYKAG      120
YDRLFGAKLF KDGDLA KFVIAQEGES SPKLAHLAHF EKFSTYFTGF HDNRKNMYSD      180
EDKHTAIAYR LIHENLPRFI DNLQILTTIK QKHSALYDQI INELTASGLD VSLASHLDGY      240
HKLLTQEGIT AYNTLLGGIS GEAGSPKIQG INELINSHHN QHCHKSERIA KLRPLHKQIL      300
SDGMSVSFLP SKFADDSEMC QAVNEFYRHY ADVFAKVQSL FDGFDDHQKD GIYVEHKNLN      360
ELSKQAFGDF ALLGRVLDGY YVDVVNPEFN ERFAKAKTDN AKAKLTKEKD KPIKGVHSLA      420
SLEQAIEHYT ARHDDESVQA GKLGQYFKHG LAGVDNPIQK IHNNHSTIKG FLERERPAGE      480
RALPKIKSGK NPEMTQLRQL KELLDNALNV AHFAKLLTTK TTLDNQDGNF YGEFGVLYDE      540
LAKIPTLYNK VRDYLSQKPF STEKYKLNFG NPTLLNGWDL NKEKDNFGVI LQKDGCYYLA      600
LLDKAHKKVF DNAPNTGKSI YQKMIYKYLE VRKQFPKVFF SKEAIAINYH PSKELVEIKD      660
KGRQRSDDER LKLYRPILEC LKIHPKYDKK FEGAIGDIQL RDKDKKGREV PISEKDLFKD      720
INGIFSSKPK LEMEDFFIGE FKRYNPSQDL VDQYNIYKKI DSNDNRKKEN FYNNHPKFKK      780
DLVRYYYESM CKHEEWEESF EFSKKLQDIG CYVDVNELFT EIETRRLNYK ISFCNINADY      840
IDELVEQGQL YLFQIYNKDF SPKAHGKPNL HTLYFKALFS EDNLADPIYK LNGEAQIFYR      900
KASLDMNETT IHRAGEVLEN KNPDNPKKRQ FVYDIIKDKR YTQKDFMLHV PITMNFGVQG      960
MTIKEFNKKV NQSIQQYDEV NVIGIDRGER HLLYLTVINS KGEILEQCSL NDITTASANG    1020
TQMTTPYHKI LDKREIERLN ARVGWGEIET IKELKSGYLS HVVHQISQLM LKYNAIVVLE    1080
DLNFGFKRGR FKVEKQIYQN FENALIKKLN HLVLKDKADD EIGSYKNALQ LTNNFTDLKS    1140
IGKQTGFLFY VPAWNTSKID PETGFVDLLK PRYENIQASQ AFFGKFDKIC YNADKDYFEF    1200
HIDYAKFTDK AKNSRQIWTI CSHGDKRYVY DKTANQNKGA AKGINVNDIL KSLFARHHIN    1260
EKQPNLVMDI CQNNDKEFHK SLMYLLKTLL ALRYSNASSD EDFILSPVAN DEGVFFNSAL    1320
ADDTQPQNAD ANGAYHIALK GLWLLNELKN SDDLNKVKLA IDNQTWLNFA QNR            1373
```

```
SEQ ID NO: 37          moltype = AA  length = 1352
FEATURE                Location/Qualifiers
REGION                 1..1352
                       note = Parcubacteria bacterium
source                 1..1352
                       mol_type = protein
                       organism = unidentified
SEQUENCE: 37
MENIFDQFIG KYSLSKTLRF ELKPVGKTED FLKINKVFEK DQTIDDSYNQ AKFYFDSLHQ    60
KFIDAALASD KTSELSFQNF ADVLEKQNKI ILDKKREMGA LRKRDKNAVG IDRLQKEIND   120
AEDIIQKEKE KIYKDVRTLF DNEAESWKTY YQEREVDGKK ITESKADLKQ KGADFLTAAG   180
ILKVLKYEFP EEKEKEFQAK NQPSLFVEEK ENPGQKRYIF DSFDKFAGYL TKFQQTKKNL   240
YAADGTSTAV ATRIADNFII FHQNTKVFRD KYKNNHTDLG FDEENIFEIE RYKNCLLQRE   300
IEHIKNENSY NKIIGRINKK IKEYRDQKAK DTKLTKSDFP FFKNLDKQIL GEVEKEKQLI   360
EKTREKTEED VLIERFKEFI ENNEERFTAA KKLMNAFCNG EFESEYEGIY LKNKAINTIS   420
RRWFVSDRDF ELKLPQQKSK NKSEKNEPKV KKFISIAEIK NAVEELDGDI FKAVFYDKKI   480
IAQGGSKLEQ FLVIWKYEFE YLFRDIEREN GEKLLGYDSC LKIAKQLGIF PQEKEAREKA   540
TAVIKNYADA GLGIFQMMKY FSLDDKDRKN TPGQLSTNFY AEYDGYYKDF EFIKYYNEFR   600
NFITKKPFDE DKIKLNFENG ALLKGWDENK EYDFMGVILK KEGRLYLGIM HKNHRKLFQS   660
MGNAKGDNAN RYQKMIYKQI ADASKDVPRL LLTSKKAMEK FKPSQEILRI KKEKTFKRES   720
KNFSLRDLHA LIEYYRNCIP QYSNWSFYDF QFQDTGKYQN IKEFTDDVQK YGYKISFRDI   780
DDEYINQALN EGKMYLFEVV NKDIYNTKNG SKNLHTLYFE HILSAENLND PVFKLSGMAE   840
IFQRQPSVNE REKITTQKNQ CILDKGDRAY KYRRYTEKKI MPHMSLVLNT GKGEIKQVQF   900
NKIINQRISS SDNEMRVNVI GIDRGEKNLL YYSVVKQNGE IIEQASLNEI NGVNYRDKLI   960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 38          moltype = AA  length = 1260
FEATURE                Location/Qualifiers
source                 1..1260
                       mol_type = protein
                       organism = Porphyromonas crevioricanis
SEQUENCE: 38
MDSLKDFTNL YPVSKTLRFE LKPVGKTLEN IEKAGILKED EHRAESYRRV KKIIDTYHKV    60
FIDSSLENMA KMGIENEIKA MLQSFCELYK KDHRTEGEDK ALDKIRAVLR GLIVGAFTGV   120
CGRRENTVQN EKYESLFKEK LIKEILPDFV LSTEAESLPF SVEEATRSLK EFDSFTSYFA   180
GFYENRKNIY STKPQSTAIA YRLIHENLPK IEPIAKELE HIRADFSAGG               240
YIKKDERLED IFSLNYYIHV LSQAGIEKYN ALIGKIVTEG DGEMKGLNEH INLYNQQRGR   300
EDRLPLFRPL YKQILSDREQ LSYLPESFEK DEELLRALKE FYDHIAEDIL GRTQQLMTSI   360
SEYDLSRIYV RNDSQLTDIS KKMLGDWNAI YMARERAYDH EQAPKRITAK YERDRIKALK   420
GEESISLANL NSCIAFLDNV RDCRVDTYLS TLGQKEGPHG LSNLVENVFA SYHEAEQLLS   480
FPYPEENNLI QDKDNVVLIK NLLDNISDLQ RFLKPLWGMG DEPDKDERFY GEYNYIRGAL   540
DQVIPLYNKV RNYLTRKPYS TRKVKLNFGN SQLLSGWDRN KEKDNSCVIL RKGQNFYLAI   600
MNNRHKRSFE NKMLPEYKEG EPYFEKMDYK FLPDPNKMLP KVFLSKKGIE IYKPSPKLLE   660
QYGHGTHKKG DTFSMDDLHE LIDFFKHSIE AHEDWKQFGF KFSDTATYEN VSSFYREVED   720
QGYKLSFRKV SESYVYSLID QGKLYLFQIY NKDFSPCSKG TPNLHTLYWR MLFDERNLAD   780
VIYKLDGKAE IFFREKSLKN DHPTHPAGKP IKKKSRQKKG EESLFEYDLV KDRRYTMDKF   840
QFHVPITMNF KCSAGSKVND MVNAHIREAK DMHVIGIDRG ERNLLYICVI DSRGTILDQI   900
SLNTINDIDY HDLLESRDKD RQQEHRNWQT IEGIKELKQG YLSQAVHRIA ELMVAYKAVN   960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 39          moltype = AA  length = 1324
FEATURE                Location/Qualifiers
source                 1..1324
                       mol_type = protein
                       organism = Prevotella disiens
SEQUENCE: 39
MENYQEFTNL FQLNKTLRFE LKPIGKTCEL LEEGKIFASG SFLEKDKVRA DNVSYVKKEI    60
DKKHKIFIEE TLSSFSISND LLKQYFDCYN ELKAFKKDCK SDEEEVKKTA LRNKCTSIQR   120
AMREAISQAF LKSPQKKLLA IKNLIENVFK ADENVQHFSE FTSYFSGFET NRENFYSDEE   180
KSTSIAYRLV HDNLPIFIKN IYIFEKLKEQ FDAKTLSEIF ENYKLYVAGS SLDEVFSLEY   240
FNNTLTQKGI DNYNAVIGKI VKEDKQEIQG LNEHINLYNQ KHKDRRLPFF ISLKKQILSD   300
REALSWLPDM FKNDSEVIDA LKGFYIEDGF ENNVLTPLAT LLSSLDKYNL NGIFIRNNEA   360
LSSLSQNVYR NFSIDEAIDA QNAELQTFNN YELIANALRA KIKKETKQGR KSFEKYEEYI   420
DKKVKAIDSL SIQEINELVE NYVSEFNSNS GNMPRKVEDY FSLMRKGDFG SNDLIENIKT   480
KLSAAEKLLG TKYQETAKDI FKKDENSKLI KELLDATKQF QHFIKPLLGT GEEADRDLVF   540
YGDFLPLYEK FEELTLLYNK VRNRLTQKPY SKDKIRLCFN KPKLMTGWVD SKTEKSDNGT   600
QYGGYLFRKK NEIGEYDYFL GISSKAQLFR KNEAVIGDYE RLDYYQPKAN TIYGSAYEGE   660
NSYKEDKKRL NKVIIAYIEQ IKQTNIKKSI IESISKYPNI SDDDKVTPSS LLEKIKKVSI   720
```

```
DSYNGILSFK SFQSVNKEVI DNLLKTISPL KNKAEFLDLI NKDYQIFTEV QAVIDEICKQ   780
KTFIYFPISN VELEKEMGDK DKPLCLFQIS NKDLSFAKTF SANLRKKRGA ENLHTMLFKA   840
LMEGNQDNLD LGSGAIFYRA KSLDGNKPTH PANEAIKCRN VANKDKVSLF TYDIYKNRRY   900
MENKFLFHLS IVQNYKAAND SAQLNSSATE YIRKADDLHI IGIDRGERNL LYYSVIDMKG   960
NIVEQDSLNI IRNNDLETDY HDLLDKREKE RKANRQNWEA VEGIKDLKKG YLSQAVHQIA  1020
QLMLKYNAII ALEDLGQMFV TRGQKIEKAV YQQFEKSLVD KLSYLVDKKR PYNELGGILK  1080
AYQLASSITK NNSDKQNGFL FYVPAWNTSK IDPVTGFTDL LRPKAMTIKE AQDFFGAFDN  1140
ISYNDKGYFE FETNYDKFKI RMKSAQTRWT ICTFGNRIKR KKDKNYWNYE EVELTEEFKK  1200
LFKDSNIDYE NCNLKEEIQN KDNRKFFDDL IKLLQLTLQM RNSDDKGNDY IISPVANAEG  1260
QFFDSRNGDK KLPLDADANG AYNIARKGLW NIRQIKQTKN KDDLNLSISS TEWLDFVREK  1320
PYLK                                                              1324

SEQ ID NO: 40           moltype = AA  length = 1484
FEATURE                 Location/Qualifiers
REGION                  1..1484
                        note = Peregrinibacteria bacterium
SITE                    1073
                        note = misc_feature - Xaa can be any naturally occurring
                         amino acid
source                  1..1484
                        mol_type = protein
                        organism = unidentified
SEQUENCE: 40
MSNFFKNFTN LYELSKTLRF ELKPVGDTLT NMKDHLEYDE KLQTFLKDQN IDDAYQALKP    60
QFDEIHEEFI TDSLESKKAK EIDFSEYLDL FQEKKELNDS EKKLRNKIGE TFNKAGEKWK   120
KEKYPQYEWK KGSKIANGAD ILSCQDMLQF IKYKNPEDEK IKNYIDDTLK GFFTYFGGFN   180
QNRANYYETK KEASTAVATR IVHENLPKFC DNVIQFKHII KRKKDGTVEK TERKTEYLNA   240
YQYLKNNNKI TQIKDAETEK MIESTPIAEK IFDVYYFSSC LSQKQIEEYN RIIGHYNLLI   300
NLYNQAKRSE GKHLSANEKK YKDLPKFKTL YKQIGCGKKK DLFYTIKCDT EEEANKSRNE   360
GKESHSVEEI INKAQEAINK YFKSNNDCEN INTVPDFINY ILTKENYEGV YWSKAAMNTI   420
SDKYFANYHD LQDRLKEAKV FQKADKKSED DIKIPEAIEL SGLFGVLDSL ADWQTTLFKS   480
SILSNEKLKI ITDSQTPSEA LLKMIFNDIE KNMESFLKET NDIITLKKYK GNKEGTEKIK   540
QWFDYTLAIN RMLKYFLVKE NKIKGNSLDT NISEALKTLI YSDDAEWFKW YDALRNYLTQ   600
KPQDEAKENK LKLNFDNPSL AGGWDVNKEC SNFCVILKDK NEKKYLAMIK KGENTLFQKE   660
WTEGRGKNLT KKSNPLFEIN NCEILSKMEY DFWADVSKMI PKCSTQLKAV VNHFKQSDNE   720
FIFPIGYKVT SGEKFREECK ISKQDFELNN KVFNKNELSV TAMRYDLSST QEKQYIKAFQ   780
KEYWELLFKQ EKRDTKLTNN EIFNEWINFC NKKYSELLSW ERKYKDALTN WINFCKYFLS   840
KYPKTTLFNY SFKESENYNS LDEFYRDVDI CSYKLNINTT INKSILDRLV EEGKLYLFEI   900
KNQDSNDGKS IGHKNNLHTI YWNAIFENFD NRPKLNGEAE IFYRKAISKD KLGIVKGKKT   960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRKNW QRIGTI       KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNPFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 41           moltype = AA  length = 1245
FEATURE                 Location/Qualifiers
source                  1..1245
                        mol_type = protein
                        organism = Porphyromonas macacae
SEQUENCE: 41
MKTQHFFEDF TSLYSLSKTI RFELKPIGKT LENIKKNGLI RRDEQRLDDY EKLKKVIDEY    60
HEDFIANILS SFSFSEEILQ SYIQNLSISE ARAKIEKTMR DTLAKAFSED ERYKSIFKKE   120
LVKKDIPVWC PAYKSLCKKF DNFTTSLVPF HENRKNLYTS NEITASIPYR IVHVNLPKFI   180
QNIEALCELQ KKMGADLYLE MMENLRNVWP SFVKTPDDLC NKTYNHLMV QSSISEYNRF   240
VGGYSTEDGT KHQGINEWIN IYRQRNKEMR LPGLVFLHKQ ILAKVDSSSF ISDTLENDDQ   300
VFCVLRQFRK LFWNTVSSKE DDAASLKDLF CGLSGYDPEA IYVSDAHLAT ISKNIFDRWN   360
YISDAIRRKT EVLMPRKKES VERYAEKISK QIKKRQSYSL AELDDLLAHY SEESLPAGFS   420
LLSYFTSLGG QKYLVSDGEV ILYEEGSNIW DEVLIAFRDL QVILDKDPFE KKLGKDEEAV   480
SVIKKALDSA LRLRKFFDLL SGTGAEIRRD SSFYALYTDR MDKLKGLLKM YDKVRNYLTK   540
KPYSIEKFKL HFDNPSLLSG WDKNKELNNL SVIFRQNGYY YLGIMTPKGK NLFKTLPKLG   600
AEEMFYEKME YKQIAEPMLM LPKVFFPKKT KPAFAPDQSV VDIYNKKTFK TGQKGFNKKD   660
LYRLIDFYKE ALTVHEWKLF NFSFSPTEQY RNIGEFFDEV REQAYKVSMV NVPASYIDEA   720
VENGKLYLFQ IYNKDFSPYS KGIPNLHTLY WKALFSEQNQ SRVYKLCGGG ELFYRKASLH   780
MQDTTVHPKG ISIHKKNLNK KGETSLFNYD LVKDKRFTED KFFFHVPISI NYKNKKITNV   840
NQMVRDYIAQ NDDLQHGIDR GERNLLYISR IDTRGNLLEQ FSLNVIESDK GDLRTDYQKI   900
LGDREQERLR RRQEWKSIES IKDLKDGYMS QVVHKICNMV VEHKAIVVLE NLNLSFMKGR   960
KKVEKSVYEK FERMLVDKLN YLVVDKKNLS NEPGGLYAAY QLTNPLFSFE ELHRYPQSGI  1020
LFFVDPWNTS LTDPSTEFVN LLGRINYTNV GDARKFFDRF NAIRYDGKGN ILFDLDLSRF  1080
DVRVETQRKL WTLTTFGSRI AKSKKSGKWM VERIENSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVQRIK RGDHESIHRI GRAQWLRYVQ EGIVE                  1245

SEQ ID NO: 42           moltype = AA  length = 1250
FEATURE                 Location/Qualifiers
```

| | | |
|---|---|---|
| source | 1..1250 | |
| | mol_type = protein | |
| | organism = Smithella sp. | |

SEQUENCE: 42
```
MQTLFENFTN QYPVSKTLRF ELIPQGKTKD FIEQKGLLKK DEDRAEKYKK VKNIIDEYHK      60
DFIEKSLNGL KLDGLEKYKT LYLKQEKDDK DKKAFDKEKE NLRKQIANAF RNNEKFKTLF     120
AKELIKNDLM SFACEEDDKKN VKEFEAFTTY FTGFHQNRAN MYVADEKRTA IASRLIHENL    180
PKFIDNIKIF EKMKKEAPEL LSPFNQTLKD MKDVIKGTTL EEIFSLDYFN KTLTQSGIDI     240
YNSVIGGRTP EEGKTKIKGL NEYINTDFNQ KQTDKKKRQP KPFKQLYKQIL SDRQSLSFIA    300
EAFKNDTEIL EAIEKFYVNE LLHFSNEGKS TNVLDAIKNA VSNLESFNLT KMYFRSGASL    360
TDVSRKVFGE WSIINRALDN YYATTYPIKP REKSEKYEER KEKWLKQDFN VSLIQTAIDE    420
YDNETVKGKN SGKVIADYFA KFCDDKETDL IQKVNEGYIA VKDLLNTPCP ENEKLGSNKD    480
QVKQIKAFMD SIMDIMHFVR PLSLKDTDKE KDETFYSLFT PLYDHLTQTI ALYNKVRNYL    540
TQKPYSTEKI KLNFENSTLL GGWDLNKETD NTAIILRKDN LYYLGIMDKR HNRIFRNVPK    600
ADKKDFCYEK MVYKLLPGAN KMLPKVFFSQ SRIQEFTPSA KLLENYANET HKKGDNFNLN    660
HCHKLIDFFK DSINKHEDWK NFDFRFSATS TYADLSGFYH EVEHQGYKIS FQSVADSFID    720
DLVNEGKLYL FQIYNKDFSP FSKGKPNLHT LYWKMLFDEN NLKDVVYKLN GEAEVFYRKK    780
SIAEKNTTIH KANESIITMN PDNPKATSTF NYDIVKDKRY TIDKFQFHIP ITMNFKAEGI    840
FNMMQRVNQF LKANPDINII GIDRGERHLL YYALINQKGK ILKQDTLNVI ANEKQKVDYH    900
NLLDKKEGDR ATARQEWGVI ETIKELKEGY LSQVIHKLTD LMIENNAIIV MEDLNFGFKR    960
GRQKVEKQVY QKFEKMLIDK LNYLVDKNKK ANELGGLLNA FQLANKFESF QKMGKQNGFI   1020
FYVPAWNTSK TDPATGFIDF LKPRYENLNQ AKDPFFEKFDS IRLNSKADYF EPAFDFKNFT   1080
EKADGGRTKW TVCTTNEDRY QWNRALNNNR GSQEKYDITA ELKSLFDGKV DYKSGKDLKQ   1140
QIASQESADF FKALMKNLSI TLSLRHNNGE KGDNEQDYIL SPVADSKGRF FDSRKADDDM   1200
PKNADANGAY HIALKGLWCL EQISKTDDLK KVKLAISNKE WLEFVQTLKG             1250
```

| | | |
|---|---|---|
| SEQ ID NO: 43 | moltype = AA length = 166 | |
| FEATURE | Location/Qualifiers | |
| source | 1..166 | |
| | mol_type = protein | |
| | organism = Escherichia coli | |

SEQUENCE: 43
```
SEVEFSHEYW MRHALTLAKR AWDEREVPVG AVLVHNNRVI GEGWNRPIGR HDPTAHAEIM     60
ALRQGGLVMQ NYRLIDATLY VTLEPCVMCA GAMIHSRIGR VVFGARDAKT GAAGSLMDVL   120
HHHPGMNHRVE ITEGILADEC AALLSDFFRM RRQEIKAQKK AQSSTD                  166
```

| | | |
|---|---|---|
| SEQ ID NO: 44 | moltype = AA length = 166 | |
| FEATURE | Location/Qualifiers | |
| REGION | 1..166 | |
| | note = adenosine deaminase | |
| source | 1..166 | |
| | mol_type = protein | |
| | organism = synthetic construct | |

SEQUENCE: 44
```
SEVEFSHEYW MRHALTLAKR ARDEREVPVG AVLVLNNRVI GEGWNRAIGL HDPTAHAEIM     60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM PRQVFNAQKK AQSSTD                   166
```

| | | |
|---|---|---|
| SEQ ID NO: 45 | moltype = AA length = 166 | |
| FEATURE | Location/Qualifiers | |
| REGION | 1..166 | |
| | note = adenosine deaminase | |
| source | 1..166 | |
| | mol_type = protein | |
| | organism = synthetic construct | |

SEQUENCE: 45
```
SEVEFSHEYW MRHALTLAKR AWDEREVPVG AVLVLNNRVI GEGWNRSIGL HDPTAHAEIM     60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM RRQVFNAQKK AQSSTD                   166
```

| | | |
|---|---|---|
| SEQ ID NO: 46 | moltype = AA length = 166 | |
| FEATURE | Location/Qualifiers | |
| REGION | 1..166 | |
| | note = adenosine deaminase | |
| source | 1..166 | |
| | mol_type = protein | |
| | organism = synthetic construct | |

SEQUENCE: 46
```
SEVEFSHEYW MRHALTLAKR ALDEREVPVG AVLVLNNRVI GEGWNRAIGL HDPTAHAEIM     60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM RRQVFNAQKK AQSSTD                   166
```

| | | |
|---|---|---|
| SEQ ID NO: 47 | moltype = AA length = 166 | |
| FEATURE | Location/Qualifiers | |
| REGION | 1..166 | |
| | note = adenosine deaminase | |
| source | 1..166 | |
| | mol_type = protein | |
| | organism = synthetic construct | |

```
SEQUENCE: 47
SEVEFSHEYW MRHALTLAKR ALDEREVPVG AVLVLNNRVI GEGWNRAIGL HDPTAHAEIM      60
ALRQGGLVMQ NYRLIDATLY VTFEPCVMCA GAMIHSRIGR VVFGVRNAKT GAAGSLMDVL     120
HYPGMNHRVE ITEGILADEC NALLCYFFRM PRQVFNAQKK AQSSTD                   166

SEQ ID NO: 48            moltype = AA   length = 167
FEATURE                  Location/Qualifiers
REGION                   1..167
                         note = adenine deaminase
source                   1..167
                         mol_type = protein
                         organism = synthetic construct
SEQUENCE: 48
MSEVEFSHEY WMRHALTLAK RARDEREVPV GAVLVLNNRV IGEGWNRAIG LHDPTAHAEI      60
MALRQGGLVM QNYRLYDATL YSTFEPCVMC AGAMIHSRIG RVVFGVRNAK TGAAGSLMDV    120
LHHPGMNHRV EITEGILADE CAALLCRFFR MPRRVFNAQK KAQSSTD                  167

SEQ ID NO: 49            moltype = AA   length = 167
FEATURE                  Location/Qualifiers
REGION                   1..167
                         note = adenine deaminase
source                   1..167
                         mol_type = protein
                         organism = synthetic construct
SEQUENCE: 49
MSEVEFSHEY WMRHALTLAK RARDEREVPV GAVLVLNNRV IGEGWNRAIG LHDPTAHAEI      60
MALRQGGLVM QNYRLIDATL YVTFEPCVMC AGAMIHSRIG RVVFGVRNSK RGAAGSLMNV    120
LNYPGMNHRV EITEGILADE CAALLCDFYR MPRQVFNAQK KAQSSIN                  167

SEQ ID NO: 50            moltype = AA   length = 228
FEATURE                  Location/Qualifiers
source                   1..228
                         mol_type = protein
                         organism = Rattus norvegicus
SEQUENCE: 50
SSETGPVAVD PTLRRRIEPH EFEVFFDPRE LRKETCLLYE INWGGRHSIW RHTSQNTNKH      60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLK                  228

SEQ ID NO: 51            moltype = AA   length = 199
FEATURE                  Location/Qualifiers
source                   1..199
                         mol_type = protein
                         organism = Homo sapiens
SEQUENCE: 51
MEASPASGPR HLMDPHIFTS NFNNGIGRHK TYLCYEVERL DNGTSVKMDQ HRGFLHNQAK      60
NLLCGFYGRH AELRFLDLVP SLQLDPAQIY RVTWFISWSP CFSWGCAGEV RAFLQENTHV    120
RLRIFAARIY DYDPLYKEAL QMLRDAGAQV SIMTYDEFKH CWDTFVDHQG CPFQPWDGLD    180
EHSQALSGRL RAILQNQGN                                                 199

SEQ ID NO: 52            moltype = DNA   length = 621
FEATURE                  Location/Qualifiers
source                   1..621
                         mol_type = other DNA
                         organism = Petromyzon marinus
SEQUENCE: 52
acagatgcag agtatgtgag aattcacgaa agctggaca tctataccttt caagaagcag     60
ttcttttaaca ataagaagtc tgtgagccat aggtgctacg tgctgttcga gctgaagaga  120
aggggtgaaa gaagggcatg tttttggggg tatgctgtga acaagcccca gtctggaact   180
gagagaggca ttcacgccga aattttcagc atcagaaagg tggaggaata cctgaggat    240
aaccctggac agtttacaat taattggtat tctagctggt ctccatgcgc tgactgtgcc   300
gagaagatcc tggaatggta caaccaggag ctgagaggaa atggccatac cctgaagatt   360
tgggcctgca agctgtacta tgaaaagaac gcaagaaatc agatcggact gtggaacctg   420
agggataatg gtgtgggggct gaacgtgatg gtgtccgagc actatcagtg ctgtagaaag   480
attttcattc agtcctcaca taatcagctg aacgagaata gatggctgga aaagactctg   540
aagagggctg agaagagaag gtccgaactg tcaattatga tccaggtgaa gatcctgcac   600
accactaagt cacctgccgt g                                             621

SEQ ID NO: 53            moltype = AA   length = 160
FEATURE                  Location/Qualifiers
REGION                   1..160
                         note = cytosine deaminase
source                   1..160
                         mol_type = protein
                         organism = synthetic construct
SEQUENCE: 53
FERNYDPREL RKETYLLYEI KWGKSGKLWR HWCQNNRTQH AEVYFLENIF NARRFNPSTH      60
CSITWYLSWS PCAECSQKIV DFLKEHPNVL EIYVARLYYH EDERNRQGLR DLVNSGVTIR    120
```

```
IMDLPDYNYC WKTFVSDQGG DEDYWPGHFA PWIKQYSLKL                          160

SEQ ID NO: 54           moltype = AA  length = 207
FEATURE                 Location/Qualifiers
REGION                  1..207
                        note = cytosine deaminase
source                  1..207
                        mol_type = protein
                        organism = synthetic construct
SEQUENCE: 54
TDAEYVRIHE KLDIYTFKKQ FSNNKKSVSH RCYVLFELKR RGERRACFWG YAVNKPQSGT    60
ERGIHAEIFS IRKVEEYLRD NPGQFTINWY SSWSPCADCA EKILEWYNQE LRGNGHTLKI    120
WVCKLYYEKN ARNQIGLWNL RDNGVGLNVM VSEHYQCCRK IFIQSSHNQL NENRWLEKTL    180
KRAEKRRSEL SIMFQVKILH TTKSPAV                                       207

SEQ ID NO: 55           moltype = AA  length = 228
FEATURE                 Location/Qualifiers
REGION                  1..228
                        note = cytosine deaminase
source                  1..228
                        mol_type = protein
                        organism = synthetic construct
SEQUENCE: 55
SSKTGPVAVD PTLRRRIEPH EFEVFFDPRE LRKETCLLYE INWGGRHSIW RHTSQNTNKH    60
VEVNFIEKFT TERYFCPNTR CSITWFLSWS PCGECSRAIT EFLSRYPNVT LFIYIARLYH    120
LANPRNRQGL RDLISSGVTI QIMTEQESGY CWHNFVNYSP SNESHWPRYP HLWVRLYVLE    180
LYCIILGLPP CLNILRRKQS QLTSFTIALQ SCHYQRLPPH ILWATGLK                 228

SEQ ID NO: 56           moltype = AA  length = 162
FEATURE                 Location/Qualifiers
REGION                  1..162
                        note = cytosine deaminase
source                  1..162
                        mol_type = protein
                        organism = synthetic construct
SEQUENCE: 56
SFERNYDPRE LRKETYLLYE IKWGKSGKLW RHWCQNNRTQ HAEVYFLENI FNARRFNPST    60
HCSITWYLSW SPCAECSQKI VDFLKEHPNV NLEIYVARLY YPENERNRQG LRDLVNSGVT    120
IRIMDLPDYN YCWKTFVSDQ GGDEDYWPGH FAPWIKQYSL KL                       162

SEQ ID NO: 57           moltype = AA  length = 229
FEATURE                 Location/Qualifiers
source                  1..229
                        mol_type = protein
                        organism = Rattus norvegicus
SEQUENCE: 57
MSSETGPVAV DPTLRRRIEP HEFEVFFDPR ELRKETCLLY EINWGGRHSI WRHTSQNTNK    60
HVEVNFIEKF TTERYFCPNT RCSITWFLSW SPCGECSRAI TEFLSRYPHV TLFIYIARLY    120
HHADPRNRQG LRDLISSGVT IQIMTEQESG YCWRNFVNYS PSNEAHWPRY PHLWVRLYVL    180
ELYCIILGLP PCLNILRRKQ PQLTFFTIAL QSCHYQRLPP HILWATGLK                229

SEQ ID NO: 58           moltype = AA  length = 198
FEATURE                 Location/Qualifiers
source                  1..198
                        mol_type = protein
                        organism = Homo sapiens
SEQUENCE: 58
MDSLLMNRRK FLYQFKNVRW AKGRRETYLC YVVKRRDSAT SFSLDFGYLR NKNGCHVELL    60
FLRYISDWDL DPGRCYRVTW FTSWSPCYDC ARHVADFLRG NPNLSLRIFT ARLYFCEDRK    120
AEPEGLRRLH RAGVQIAIMT FKDYFYCWNT FVENHERTFK AWEGLHENSV RLSRQLRRIL    180
LPLYEVDDLR DAFRTLGL                                                 198

SEQ ID NO: 59           moltype = AA  length = 197
FEATURE                 Location/Qualifiers
REGION                  1..197
                        note = cytosine deaminase
source                  1..197
                        mol_type = protein
                        organism = synthetic construct
SEQUENCE: 59
MDSLLMNRRE FLYQFKNVRW AKGRRETYLC YVVKRRDSAT SFSLDFGYLR NKNGCHVELL    60
FLRYISDWDL DPGRCYRVTW FISWSPCYDC ARHVADFLRG NPNLSLRIFT ARLYFCEDRK    120
AEPEGLRRLH RAGVQIAIMT FKDYFYCWNT FVENHGRTFK AWEGLHENSV RLSRQLRRIL    180
LPLYEVDDLR DAFRTCT                                                  197

SEQ ID NO: 60           moltype = AA  length = 83
FEATURE                 Location/Qualifiers
source                  1..83
                        mol_type = protein
```

```
                        note = Bacillus phage
                        organism = unidentified
SEQUENCE: 60
TNLSDIIEKE TGKQLVIQES ILMLPEEVEE VIGNKPESDI LVHTAYDEST DENVMLLTSD   60
APEYKPWALV IQDSNGENKI KML                                          83

SEQ ID NO: 61           moltype = DNA  length = 1592
FEATURE                 Location/Qualifiers
source                  1..1592
                        mol_type = other DNA
                        organism = Medicago truncatula
SEQUENCE: 61
actgttaata attttaaac gtcagcgcac taaaaaaacg aaaagacgga cacgtgaaaa      60
taaaaaacac acactagttt atgacgcaat actattttac ttatgatttg ggtacattag   120
acaaaaccgt gaaagagatg tatcagctat gaaacctgta tacttcaata cagagactta   180
ctcatatcgg atacgtacgc acgaagtatc atattaatta ttttaatttt taataaatat   240
tttatcggat acttatgtga tactctacat atacacaagg atatttctaa gatactttat   300
agatacgtat cctagaaaaa catgaagagt aaaaaagtga gacaatgttg taaaaattca   360
ttataaatgt atatgattca atttagata tgcatcagta taattgattc tcgatgaaac   420
acttaaaatt atatttcttg tggaagaacg tagcgagaga ggtgattcag ttagacaaca   480
ttaaataaaa ttaatgttaa gttcttttaa tgatgtttct ctcaatatca catcatatga   540
aaatgtaata tgatttataa gaaaattttt aaaaaatttt tttaataat cacatgtact   600
attttttaaa aattgtatct tttataataa tacaataata aagagtaatc agtgttaatt   660
tttcttcaaa tataagtttt attataaatc attgttaacg tatcataagt cattaccgta   720
tcgtatctta attttttttt aaaaccgct aattcacgta cccgtattgt attgtaccg   780
cacctgtatc acaatcgatc ttagttagaa gaattgtctc gaggcggtgc aagacagcat   840
ataatagacg tggactctct tataccaaac gttgtcgtat cacaaagggt taggtaacaa   900
gtcacagttt gtccacgtgt cacgttttaa ttggaagagg tgccgttggc gtaatataac   960
agccaatcga ttttgctat aaaagcaaat caggtaaact aaacttcttc attcttttct  1020
tccccatcgc tacaaaaccg gttccttgg aaaagagatt cattcaaacc tagcacccaa  1080
ttccgtttca aggtataatc tactttctat tcttcgatta tttattatt attagctact  1140
atcgtttaat cgatctttc ttttgatccg tcaaatttaa attcaattag ggttttgttc  1200
ttttctttca tctgattgaa atccttctga attgaaccgt ttacttgatt ttactgttta  1260
ttgtatgatt taatccttg tttttcaaag acagtcttta ggttgtgatt aggggttcat  1320
ataaattttt agatttggat ttttgtattg tatgattcaa aaaatacgtc ctttaattag  1380
attagtacat ggatatttt tacccgattt attgattgtc agggagaatt tgatgagcaa  1440
gtttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                              1592

SEQ ID NO: 62           moltype = DNA  length = 2000
FEATURE                 Location/Qualifiers
source                  1..2000
                        mol_type = other DNA
                        organism = Zea mays
SEQUENCE: 62
gtcgtgcccc tctctagaga taaagagcat tgcatgtcta aagtataaaa aattaccaca    60
tattttttg tcacacttat ttgaagtgta gtttatctat ctctatacat atatttaaac   120
ttcactctac aaataatata gtctataata ctaaataaat attagtgttt tagaggatca   180
tataaataaa ctgctagaca tggtctaaag gataattgaa tattttgaca atctacagtt   240
ttatctttt agtgtgcatg tgatctctct gttttttttg caaatagctt gacctatata   300
atacttcatc cattttatta gtacatccat ttaggattta gggttgatgg tttctataga   360
ctaatttta gtacatccat tttattcttt ttagtctcta aatttttaa aactaaaact   420
ctattttagt ttttatttta ataatttaga tataaaatga aataaaataa attgactaca   480
aataaaacaa atacccttta agaaaataaaa aaactaagca aacattttc ttgtttcgag   540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
accccctctcg agagttccgc tccacgttg gacttgctcc gctgtcggca tcagaaaatt   720
gcgtggcgga gcggcagacg tgaggcggca cggcaggcgg cctcttcctc ctctcacggc   780
accggcagct acgggggatt cctttcccac cgctcctccg ctttccctc ctcgcccgcc   840
gtaataaata gacacccct ccacaccctc tttcccaac ctcgtgttcg ttcggagcgc   900
acacacacgc aaccagatct cccccaaatc cagccgtcgg cacctccgct tcaaggtacg   960
ccgctcatcc tcccccccc cctctctcta ccttctctag atcggcgatc cggtccatgg  1020
ttagggcccg tagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatcgtat gtatgtgcct acatcttcat agttacgagt taagatgat  1500
ggatggaaat atcgatctag ataggtata catgttgatg cgggttttac tgatgcatat  1560
acagagatgc ttttttcgc ttggttgtga tgtgtggtc tggttgggcg gtcgttctag  1620
atcggagtag aatactgttt caaactacct ggtggattta ttaattttgt atcttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggattttt  1920
agcccctgcct tcatacgcta tttatttgct tggtactgtt tcttttgtcc gatgctcacc  1980
```

```
ctgttgtttg gtgatacttc                                                  2000

SEQ ID NO: 63          moltype = DNA  length = 1594
FEATURE                Location/Qualifiers
source                 1..1594
                       mol_type = other DNA
                       organism = Medicago truncatula
SEQUENCE: 63
actgttaata attttaaac  gtcagcgcac taaaaaaacg aaaagacgga cacgtgaaaa   60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaatttt aaaaaattta tttaataat cacatgtaat  600
atttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgctc gaggcggtgc aagacagcat  840
ataatagacg tggactctct tataccaaac gttgtcgtat cacaaagggt taggtaacaa  900
gtcacagttt gtccacgtgt cacgtttaa ttggaagagg tgccgttggc gtaatataac  960
agccaatcga tttttgctat aaaagcaaat caggtaaact aaacttcttc attctttct  1020
tccccatcgc tacaaaaccg gttccttgg aaaagagatt cattcaaacc tagcacccaa  1080
ttccgtttca aggtataatc tactttctat tcttcgatta ttttattatt attagctact  1140
atcgtttaat cgatctttc ttttgatccg tcaaatttaa attcaattag ggttttgttc  1200
ttttctttca tctgattgaa atccttctga attgaaccgt ttacttgatt ttactgttta  1260
ttgtatgatt taatcctttg ttttcaaag acagtcttta tgatgtgatt aggggttcat  1320
ataaattttt agatttggat ttttgtattg tatgattcaa aaaatacgtc ctttaattag  1380
attagtacat ggatatttt tacccgatttt attgattgtc agggagaatt tgatgagcaa  1440
gtttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gggt                              1594

SEQ ID NO: 64          moltype =   length =
SEQUENCE: 64
000

SEQ ID NO: 65          moltype =   length =
SEQUENCE: 65
000

SEQ ID NO: 66          moltype =   length =
SEQUENCE: 66
000

SEQ ID NO: 67          moltype = AA  length = 1367
FEATURE                Location/Qualifiers
REGION                 1..1367
                       note = Cas9 polypeptide
source                 1..1367
                       mol_type = protein
                       organism = synthetic construct
SEQUENCE: 67
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD                1367
```

```
SEQ ID NO: 68             moltype = AA  length = 1367
FEATURE                   Location/Qualifiers
REGION                    1..1367
                          note = Cas9 polypeptide
source                    1..1367
                          mol_type = protein
                          organism = synthetic construct
SEQUENCE: 68
DKKYSIGLAI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLADDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD             1367

SEQ ID NO: 69             moltype = DNA  length = 5355
FEATURE                   Location/Qualifiers
misc_feature              1..5355
                          note = adenosine base editor construct
source                    1..5355
                          mol_type = other DNA
                          organism = synthetic construct
SEQUENCE: 69
atggcggaa gcaaaaaacg gcggattaag caagattctg aggtcgagtt tagccacgag      60
tattggatgc gccatgcctt gacgcttgcg aaacgttgcg cgaagtccca                120
gtcggagccg tgctcgtgca caataaccga gtcattggtg agggatgaa tcgtccaatc     180
gggcggcatg acccgacggc tcatgctgag atcatggctc tcagacaggg tggcttggtg    240
atgcagaact atagactcat tgatgccaca ctctacgtca ctctcgaacc gtgcgtaatg    300
tgcgcgggtg caatgattca ttccagaatt ggccgtgtcg tcttcggtgc gcgggacgcg    360
aagaccggag cggctggcag cctcatggac gtgcttcacc atcctggtat gaaccaccgg    420
gtagagatca ccgaggggat tctcgcagac gagtgcgctg cccttctctc cgatttcttc    480
cgcatgaggc gacaggagat taaggcccag aagaaagccc aatcatcgac tgattcgggt    540
ggcagctcgg gtgttctag tggttcagaa acaccgggca caagcgaatc gccaacccct    600
gaatctagcg gtgggagttc tgagggtcg tcagaggttg agtttagcca cgaatattgc    660
atgcgccatg ccctgacttt ggctaagcgc gctcgggacg agcgcgaagt accggtggga    720
gcggtgttag tgcttaacaa tcgggtcatt ggtgaaggct ggaatcgcgc aattggcctg    780
catgatccga cggcgcacgc tgagataatg gctctccgtc aaggaggtct agtgatgcag    840
aactacaggc ttatcgacgc gacactatat gtcacattcg agcctgcgt gatgtgtgcc    900
ggggcgatga tccactccag aatcgggcga gtcgtcttcg gcgtcaggaa cgccaagacc    960
ggcgcggctg gtcgctgat ggacgtgctc cattccctg ggatgaacca tcgcgttgag     1020
atcactgagg gcatactcgc cgatgagtgt gcggccctac tttgctattt cttccgaatg    1080
ccacgtcaag tattcaacgc tcagaagaag gctcagtcat ccactgacag cggtggggc    1140
agcggcggtt catcgggcag cgagactcct ggaacgtcgg aatcggctac gcccgagagc    1200
agtggcggta gttcgggcgg cagtgacaag aagtacagca tcgggctggc catcgggacc    1260
aactccgtcg gctgggctgt gattaccgac gagtacaagg tgccatccaa gaagttcaag    1320
gtcctcggca acactgaccg gcacagcatt aagaagaacc tgattgggcg gctcacacc     1380
gattcgggg agactgcgga ggcgaccagg ctgaagcgga ctgcgcgccc gaggtacacc    1440
aggaggaaga tcggatctg ctacctccag gagattttct cgaatgagat ggccaaggtg    1500
gacgattcct tcttccatcg cctggaggag tcgttcctcg ttgaggagga caagaagcat    1560
gagaggcatc ccattttcgg gaatatcgtt gacgaggtgg cttaccatga gaagtacccg    1620
accatctacc atctgcggaa gaagctcgtc gattcgacca ataaggcga cctgcggctg    1680
atctacctgg ccctcgcgca catgattaag ttccggggcc atttcctcat cgagggcgac    1740
ctcaacccgg acaactcgga cgtggataag ctcttcattc agctcgtgca gatacacaac    1800
cagctcttcg aggagaatcc cattaacgcc tcggggtcg acgctaaggc tattctctcg    1860
gctcggctgt cgaagtcgcg ccggctggag aatctcattg cccagctccc aggcgagaag    1920
aagaacgtcc tcttcggcaa cctgattgcc agctcgatgt cgcacacc gaatttcgag     1980
tcgaacttcg acctgccgga ggacgctaag ctccagctca gcaaggatac ttacgatgat    2040
gacctcgata acctgctcgc ccagattggg atcagtacg cggatctgtt cctcgcggcc    2100
aagaatctca gcgatgctat tctcctgtcg gacattctcc gcgtcaacac agagattact    2160
aaggccccac tgtcggcgag catgattaag aggtacgatg agcatcatca ggacctgaca    2220
ctgctcaagg cgctggtccg gcagcagctc cccgagaagt acaaggagat ttcttcgat     2280
```

```
cagtcaaaga atgggtacgc gggctacatt gatggcggcg cgtcccagga ggagttctac  2340
aagttcatta agcccatcct ggagaagatg gacgggaccg aggagctgct ggtgaagctc  2400
aatcgggagg acctgctccg gaagcagcgc acattcgaca atggctcgat tcctcaccag  2460
attcacctgg gcgagctgca cgccattctc cgcaggcagg aggacttcta cccgttcctc  2520
aaggacaacc gcgagaagat cgagaagatc ctgaccttcc ggattccata ctacgtgggg  2580
ccgctcgcgc gggggaactc ccggttcgcg tggatgactc gcaagtccga agaaacgatt  2640
acaccgtgga atttcgagga ggtcgtcgac aagggcgcta gtgcgcagtc attcattgag  2700
aggatgacca atttcgataa gaacctgcct aacgagaagg tgctgccgaa gcattcgctg  2760
ctctacgagt acttcaccgt ttacaatgag ctgaccaagg tgaagtatgt gactgaggcc  2820
atgaggaagc cagcgttcct gagcggccag cagaagaggg ctatcgtgga cctgctcttc  2880
aagactaacc ggaaggtgac tgtgaagcag ctcaaggagg actacttcaa gaagattgag  2940
tgcttcgatt ccgttgagat tagcggggtg gaggatcggt tcaatgcttc gctcgggaca  3000
taccacgatc tcctgaagat cattaaggat aaggacttcc tcgacaacga ggagaacgag  3060
gacattctcg aagatattgt cctgaccctc accctcttcg aggatcggga gatgatcgag  3120
gagaggctca agacatacgc tcatctgttc gatgataagg tcatgaagca gctgaagcgc  3180
aggcggtaca cagggtgggg gcggctgagc cggaagctga tcaacgggat tcgggataag  3240
cagtccggga agacaattct cgacttcctc aagtccgacg ggttcgctaa ccggaacttc  3300
atgcagctca ttcatgatga ctcgcagcta ttcaaggagg atattcagaa ggcgcaggtt  3360
tcggggcagg gcgactcgct ccacgagcat attgcgaatc tggcgggctc ccccgcgatt  3420
aagaaggca ttctgcaaac cgtcaaggtg gttgatgagc tggtcaaggt catggggcgg  3480
cataagccag agaatattgt catcgagatg gcgcgggaga atcagaccac acagaagggg  3540
cagaagaact cacgggagcg gatgaagcgc atcgagaggg gctgtcaagga ggctgggtcg  3600
cagatcctga aggagcatcc cgtggagaac actcagctgc aaaatgagaa gctgtacctc  3660
tactacctcc agaacgggag ggacatgtat gtggatcagg agctggatat taataggctg  3720
agcgattacg atgtcgacca cattgtccca cagtcgttcc tgaaggacga cagcattgac  3780
aacaaggtgc tgacccgctc ggataagaac agggcaagg gcgataagtt tccaagcgag  3840
gaggttgtga agaagatgaa gaactactgg cggcagctcc tgaacgcgaa gctcatcaca  3900
cagcggaagt tcgacaacct caccaaggct gagcgcgggg gcctgagcga gctgacaag  3960
gcgggggttca ttaagaggca gctggtcgag acacggcaga ttacaaagca tgttgcgcag  4020
attctcgatt cccggatgaa caccaagtac gatgagaacg ataagctgat tcgggaggtc  4080
aaggtaatta ccctgaagtc caagctggtg tccgacttca ggaaggactt ccagttctac  4140
aaggttcggg agatcaacaa ctaccaccac gcgcatgatg cctacctcaa cgcggtcgtg  4200
gggaccgctc tcatcaagaa gtacccaaag ctggagtcag agttcgtcta cggggattac  4260
aaggtttacg acgtgcggaa gatgatcgct aagagcgagc aggagattgg caaggctacc  4320
gctaagtact tcttctactc caacatcatg aacttcttca agacagagat taccctcgcg  4380
aatggcgaga tccggaagag gcccctcatc gagacaaatg gggagacagg ggagattgtc  4440
tgggataagg ggcgggattt cgcgaccgtc cggaaggtcc tgtcgatgcc ccaggttaat  4500
attgtcaaga agactgaggt ccagactggc ggcttctcaa aggagtcgat tctcccaaag  4560
aggaactccg ataagctcat tgctcggaag aaggattggg accccaagaa gtacgggtga  4620
ttcgactccc ccactgttgc ttactctgtt ctggttgttg ctaaggtgga gaaggggaag  4680
tcgaagaagc tgaagagcgt gaaggagctg ctcgggatta caattatgga gaggtcatcc  4740
ttcgagaaga tcccatcga cttcctggag gccaagggct acaaggaggt gaagaaggac  4800
ctgattatta agctgcccaa gtactcgctc ttcgagctgg agaatgggcg gaagcggata  4860
ctggcgtccg cggggggagct gcaaaagggg aacgagctgg cgctcccctc caagtatgtg  4920
aacttcctct acctggcgtc gcactacgag aagctgaagg ggtccccaga ggataatgag  4980
cagaagcagc tcttcgtcga gcagcataag cactacctgg acgagattat cgagcagatt  5040
agcggttct cgaagcgggt catcctcgcg gatgcgaacc tggacaaggt gctcagcgcc  5100
tacaataagc accgggacaa gccgattcgg gagcaggcgg agaatattat tcacctcttc  5160
acactcacca acctcgggc accagctgcg ttcaagtact tcgacactac tatcgaccgg  5220
aagcggtaca cctcgacgaa ggaggtgctc gacgccaccc tcattcacca gtcgatcaca  5280
ggcctgtacg agacacggat tgacctgtcc cagctcgggg gcgacggatc taagaagaga  5340
agaattaaac aagat                                                  5355
```

| SEQ ID NO: 70 | moltype = DNA  length = 5358 |
|---|---|
| FEATURE | Location/Qualifiers |
| misc_feature | 1..5358 |
| | note = adenosine base editor construct |
| source | 1..5358 |
| | mol_type = other DNA |
| | organism = synthetic construct |

SEQUENCE: 70

```
atggcgggca gcaagaaacg ccggattaag caagattccg aagtcgagtt ctcacacgaa    60
tattggatga gacacgcgct tacactagct aaaagggcgt gggacgagcg ggaagtacct   120
gttggtgccg ttctagtgca caacaatcgg gtcatcgtg aaggtgaa taggccgatt      180
ggcagacatg atcctacagc acacgctgag atcatggcgc tgcgccaggg aggactcgtt   240
atgcagaact acagactaat tgacgctacc ctctatgtca ctttggaacc atgtgtaatg   300
tgtgctgggg ctatgatcca ctccagaatt ggtagagtag tctttggcgc aagggatgct   360
aagaccggag ccgctggttc attgatggac gtcctgcacc atcccggtat gaaccatcgc   420
gttgagatta ctgagggcat tctggctgac gagtgttgcc cgctcttgtc agatttttt   480
cgaatgagga gacaggagat taaggcacag aagaaggcac agtcaagtac ggatagcgga   540
ggatcatctg gtgaagtag cggctcagag acacctggaa catcagagtc tgcaacacct   600
gaaagttccg cgggtctag cggcggatct tcagaagttg agtttagtca gaatattgg    660
atgcgtcacg ctttgaccct tgccaagcgc gcccgcgacg agcgcgaagt tccgttgga    720
gcagttctga tgctcaacaa ccgtgttatt ggtgaaggtt ggaacaggc tattggacta   780
catgaccccca ccgctcatgc tgagattatg gcccttcgac aagcgggct tgtgatgcag   840
aactacaggc ttattgacgc taccctctat gttactttcg agccatgtgt catgtgtgcg   900
ggagcaatga tacacagtag aatcgggcgg gtggtgttcg gggttcggaa cgcaaagact   960
ggagcggctg ggtcattgat ggatgtgttg cattatccag gatgaaccca cagagttgag  1020
attacagagg gcatattagc tgacgagtgt gctgccctcc tctgctactt cttcagaatg  1080
```

```
ccaagacaag tgtttaacgc ccagaagaag gctcaatcct ccacagactc tggaggatct  1140
agtggcggtt caagtgggtc tgaaacacct gggacatccg agagtgctac tcccgaatca  1200
tcaggaggtt catctggagg atctgacaag aagtatagta ttggactcgc tatcggaacc  1260
aactctgtgg ggtgggctgt tattacagat gaatataagg tgccatccaa aaagtttaaa  1320
gttctgggca atactgatag acactcaatc aagaagaatc tgataggtgc acttctgttt  1380
gatagtggag agactgccga ggcaaccaga cttaaaagga ctgcaagaag aagatatacc  1440
agaagaaaga ataggatttg ctatttgcag gaaatcttca gcaacgaaat ggccaaggtt  1500
gatgactcat ttttccatag gttggaggag agttttcttg tggaggaaga taagaagcac  1560
gaaagacacc caattttcgg gaatatagtg gacgaggtgg cttatcatga gaagtatcca  1620
actatctacc acctgagaaa gaaacttgtg gactcaaccg ataaggctga tcttaggctt  1680
atatacttgg cccttgcaca tatgatcaaa ttcaggggcc attttcttat cgaaggcgat  1740
cttaatcccg ataactcaga tgtggacaag ctgtttatac aacttgtgca aacctacaat  1800
caactcttcg aggagaatcc cattaacgcc tccggcgtgg atgcaaaagc catactgtca  1860
gccagactga gcaaaagtag gagactggag aatcttataq cccaactggc cggtgaaaag  1920
aagaatgggc tcttcggaaa tctgatcgct ctttccattgg ggttgacacc caactttaag  1980
agtaactttg acttggcaga agatgcaaag ttgcagctca gtaaagacac atatgacgat  2040
gaccttgaca atctcttggc acaaataggg gatcaatacg ctgacctttt cctcgctgcc  2100
aagaacctca gcgacgctat actgttgtcc gacattctta gggttaatac cgaaattaca  2160
aaggcccctc ttagtgcaag tatgatcaaa aggtatgatg agcatcacca agaccttaca  2220
ctgctgaagg ctctggttag acagcaactc cctgaaaagt ataaggaaat attcttcgac  2280
caaagtaaga acgggtacgc cggttatatt gatgggggcg caagtcaaga agaattttac  2340
aaattcatca agccaatttc tgaaaagatg gacgggactg aggaattgct ggtgaaactg  2400
aatagagagg accttcttag aaaacagagg acatttgaca atgggtccat cccacaccag  2460
attcatctgg gggaactcca cgcaatattg aggagacaag aagacttttta cccattcctt  2520
aaggataata gagagaaaat cgaaaaaatc ctgactttca ggattcctta ctatgttggg  2580
ccactggcca gggggaactc aagattcgct tggatgaaca gaagtcaga agaaaccata  2640
accccttgga attttgaaga ggtggttgat aaggggggcat cagcccagtc tttcatagag  2700
aggatgacca actttgataa aaatcttcca aatgagaagg ttttgccaaa acatagtctt  2760
ttgtacgagt actttactgt ttataacgaa ttgaccaagg tgaagtatgt gaccgaggga  2820
atgaggaagc cagcattttt gtccggggag caaaagagaa caatcgttga tcttctcttc  2880
aagaccaaca gaaagtgac cgtgaaacaa ctgaaggaag actacttcaa aagatagaa  2940
tgtttcgatt cagtggaaat tagccggtgtt gaagacaggt tcaatgcttc attgggtact  3000
taccacgacc tgttgaagat aatcaaagac aaggactttc tcgataatga ggagaacgaa  3060
gacatcttgg aagacattgt gcttacactc actttgtttg aggacaggga aatgattgag  3120
gaaagactca aaacttacgc tcatttgttt gatgataagg ttatgaaaca actaaaaaga  3180
agaaggtaca ccggctgggg aagattgagt aggaaactga tcaacggtat tagagataaa  3240
caatccggaa agactatcct cgatttcctt aagagtgatg gctttgcaaa taggaatttt  3300
atgcagctga ttcatgacga ctcacttacc ttcaaagaag acatccaaaa agctcaggtg  3360
tctgggcaag gcgacagtct gcatgaacat atagctaact tggctgggag tccgccatc  3420
aagaaggga tacttcaaac agttaaagtt gtggacgaat tggtgaaggt aatgggaagg  3480
cacaagcctg aaaatatagt gatagaaatg gcaaggaaa atcaaacaac ccagaaggga  3540
cagaagaaca gtagggaaag gatgaaaagg atagaagagg ggatcaaaga gcttggtagc  3600
cagatcctca aggaacatcc agtggagaat acccaacttc aaaacgagaa actctatttg  3660
tactacttgc agaacggaag agatatgtat gtggaccaag agcttgatat taacaggctg  3720
agcgattatg acgttgacca catagtgccc caatcattcc tcaaggatga ctctattgat  3780
aataaggtgc tgacaaggag tgacaagaat agagggaaat ccgacaacgt tccatccgag  3840
gaagttgtga agaagtgaa gaactactgg aggcagttgc tgaacgctaa gctcattacc  3900
cagaggaaat tcgataacct gaccaaagca gagagaggcg gctgagcga actcgataaa  3960
gcaggtttca tcaagagaca actcgtggag actaggcaaa ttactaagca cgtggctcaa  4020
atactcgaca gcaggatgaa cacaaagtac gacgagaacg acaagctcat tagagaggtt  4080
aaggttatta ctctgaaaag taaattggtt agcgatttca gaaaggattt ccaattctat  4140
aaggttagag agatcaacaa ttatcatcat gcacatgatg cctatctgaa tgctgtggtt  4200
ggtacagccc ttatcaagaa gtaccctaag ctagagagcg agtttgtgta cggagattat  4260
aaggtgtatg atgtgaggaa aatgatcgct aaaagtgagc aagagattgg aaaggctacc  4320
gccaaatact tcttttattc caatattatg aatttcttca agacagaaat caccctggct  4380
aacggcgaga taaggaagag gccgcttatc gaaactaatg gggagacagg cgaaatagtg  4440
tgggacaaag ggagggattt cgcaactgtg aggaaggttt tgagcatgcc tcaggtgaat  4500
atcgttaaga aaaccgaagt tcaaactgga gggttctcta aggaaagcat tctccccaag  4560
aggaactccg acaagctgat tgctagaaag aaagactggg acccaagaa gtatggcgga  4620
ttcgactcac ccactgtggc atatagcgtt ctcgtggtga caaaggttga aagggtaaa  4680
tccaaaaaac tcaaatccgt gaaggaactc cttggcataa ctattatgga aaggagtagc  4740
tttgaaaaga atcccatcga ctttctcgaa gctaagggct ataaggaagt taagaaggac  4800
cttataatca aacttccaaa atactccctt tttgagttgg aaaacggcag aaagagaatg  4860
ttggccagtg ccggggagct tcaaaagggc aacgaactgg ctctgcctag caaatatgtg  4920
aacttttttgt atctggcatc acactacgag aaacttaaag gctctcctga ggacaacgag  4980
caaaaacagc tctttgttga acagcataag cactaccctcg acgagattat tgagcagatc  5040
agcgagttct caaagagagt tattctggct gacgctaatc ttgacaaggt tttgtccgct  5100
tacaacaaac acagggataa gccaatcagg gagcaggagg aaaacataat ccatctcttt  5160
accctgacaa acctcggtgc ccccgctgct ttcaagtatt ttgatactaac cattgacagg  5220
aagagatata cttccactaa ggaagtgctc gacgcaaccc tcatacacca aagtatcaca  5280
ggcctctatg aaactaggat agatttgtct caacttgggg gcgatggatc taagaagaga  5340
agaattaaac aagattga                                                 5358

SEQ ID NO: 71        moltype = DNA   length = 5358
FEATURE              Location/Qualifiers
misc_feature         1..5358
                     note = adenosine base editor construct
source               1..5358
                     mol_type = other DNA
```

SEQUENCE: 71

```
atggcgggca gcaagaaacg ccggattaag caagattccg aagtcgagtt ctcacacgaa   60
tattggatga gacacgcgct tacactagct aaaagggcgt gggacgagcg ggaagtacct  120
gttggtgccg ttctagtgca caacaatcgg gtcatcggtg aaggttggaa taggccgatt  180
ggcagacatg atcctacagc acacgctgag atcatggcgc tgcgccaggg aggactcgtt  240
atgcagaact acagactaat tgacgctacc ctctatgtca ctttggaacc atgtgtaatg  300
tgtgctgggc ctatgatcca ctccagaatt ggtagagtag tctttggcgc aagggatgct  360
aagaccggag ccgctggttc attgatggac gtcctgcacc atcccggtat gaaccatcgc  420
gttgagatta ctgagggcat tctggctgac gagtgtgccg cgctcttgtc agattttttt  480
cgaatgagga gacaggagat taaggcacag aagaaggcac agtcaagtac ggatagcgga  540
ggatcatctg gtggaagtag cggctcagag acacctggaa catcagagtc tgcaacacct  600
gaaagttccg gcgggtctag cggcggatct tcagaagtta gtttagtca cgaatattgg  660
atgcgtcacg ctttgaccct tgccaagcgc gcccgcgacg agcgcgaagt tcccgttgga  720
gcagttctag tgctcaacaa ccgtgttatt ggtgaaggtt ggaacagggc tattggacta  780
catgaccccca ccgctcatgc tgagattatg gcccttcgac aaggcgggct tgtgatgcag  840
aactacaggc ttattgacgc taccctctat gttactttcg agccatgtgt catgtgtgcg  900
ggagcaatga tacacagtag aatcgggcgg gtggtgttcg gggttcggac cgcaaagact  960
ggagcggctg ggtcattgat ggatgtgttg cattatccag ggatgaacca cagagttgag 1020
attacagagg gcatattagc tgacgagtgt gctgccctcc tctgctactt cttcagaatg 1080
ccaagacaag tgtttaacgc ccagaagaag gctcaatcct ccacagactc tggaggatct 1140
agtggcggtt caagtgggtc tgaaacacct gggacatccg aggtgctac tccccgaatca 1200
tcaggaggtt catctggagg atctgacaag aaatacagta ttggccttgc aattgggact 1260
aactctgtgg gatgggccgt gattacagac gagtacaagg tgccgagcaa gaagtttaag 1320
gtgcttggga acaccgaccg gcactcgatt aagaagaacc taataggggc acttctgttc 1380
gactccggag aaaccgcaga ggccacccgc cttaaacgca acgatacacc 1440
cggcgtaaga accggatctg ctatctacag gaaatcttca gtaatgagat ggcaaaggtg 1500
gatgacagct tttttcacag gcttgaggag tcgttcctag ttgaggagga caaaaagcac 1560
gaacgccatc ccatcttcgg gaacatcgtg gatgaggtcg cctaccacga gaagtacccg 1620
accatctacc acctccgcaa gaaactcgtg gacagcaag acaagctga cctgcgactg 1680
atctacttag ccctggccca catgattaag ttccggggtc acttcctaat cgagggagac 1740
ctcaaccccg ataacagtga cgtggacaag ctcttcatcc aacttgtgca gacctacaac 1800
cagttgttcg aggagaaccc tatcaacgcc agcggggtgg acgcgaaagc tatcctgtcc 1860
gccaggctgt cgaagtctag gcgtctggag aacctaatcg ctcagctacc gggcgaaaaa 1920
aagaatggac tgttcggcaa cctcatagcc ctgagcctgg ggctgacgcc aaacttcaaa 1980
agcaacttcg acctggccga ggacgccaag ctccaattga gcaaggacac ctacgacgac 2040
gacttggaca acctattggc ccagataggt gaccagtatg cagacctctt ccttgcggcc 2100
aagaacttga gtgacgctat actgctcagt gacatcctga gggtgaacac tgagatcact 2160
aaggcccctc tctctgcctc aatgattaag cgttacgacg agcatcacca ggatctcacc 2220
ctgcttaagg cccttgttcg gcagcagctc cctgagaagt acaaggagat attttttgac 2280
cagtctaaga acggctacgc cggttacatt gacggtgggg caagccagga ggagttctac 2340
aagttcatca agccgatcct tgagaagatg gacggcaccg aggagctact tgtcaagttg 2400
aaccgggaag acctgctccg gaaacagcgt acattcgaca acggcagcat ccctccaccag 2460
atccacctgg gcgaactaca cgccatcctc cgacgtcagg aggacttcta tccattcttg 2520
aaagataaca gggaaaaat cgaaaaaata cttacgtttc gaataccttg ctacgtgggg 2580
ccccttgctc ggggaaactc cagattgca tggatgacca ggaagtcaga ggagaccatc 2640
acacctgga actttgagga ggtggttgac aaaggtgctc ctgcccagtc cttcattgag 2700
cggatgacta acttcgacaa gaacctgccc aacgagaagg tgctgccaaa gcacagcctg 2760
ctctacgaat actttactgt gtacaatgag ctgacgaagg tgaagtacgt gacagagggg 2820
atgcggaagc ccgctttcct gagcggcgag caaaaaaaag caatcgtgga cctactgttc 2880
aagaccaacc gaaaggtgac agtgaagcag ctcaaggagg actacttcaa aaaaatcgag 2940
tgcttcgact ctgttgagat aagcggcgtg gaggaccgat tcaacgcctc attgggaacc 3000
tatcacgacc tgctcaagat cattaaggac aaggacttcc tggataatga ggagaatgag 3060
gacatcctgg aggatattgt gctgacccct actctattcg aggacaggga gatgatcgag 3120
gagcgactca cagacctacgc tcacctgttc gacgacaagg ttatgaagca attgaagcgt 3180
aggcgataca cggggtgggg aagactctcc cgaaaactga taaacggcat cagggacaag 3240
cagtcaggga gacgatcttg gacttcctg aaatccgacg ggttcgccaa ccgcaacttc 3300
atgcagctca ttcacgacga ctcactaacg ttcaaagagg acattcagaa ggctcaagtc 3360
agtggacaag gcgactccct gcacgagcac attgcaaatc ttgcgggctc cccggcgatt 3420
aaaaagggca ttctccaaac ggttaaggtg gtggacgagc tggtgaaggt gatgggccga 3480
cacaagcctg agaacatcgt gatcgagatg gccaggagaa accagactac ccagaagggt 3540
cagaagaact ctcgggaacg tatgaagcgt attgaggagg ggattaagga gttgggctct 3600
caaatcctca aggagcaccc tgtggagaac actcagctcc aaaacgagaa gctgtacctg 3660
tactacctgc aaaacgggcg cgatatgtac gtggatcagg agttggacat caacaggctt 3720
agcgattacg acgtggacca tatcgtgcca cagtcattct aaaggacga cagcatcgag 3780
aacaaggttc tgacgaggag cgacaagaat cgagggaaaa gtgacaatgt tccatccgag 3840
gaggtggtca agaaaatgaa gaactattgg cgtcagcttc tgaacgccaa gctcatcacc 3900
cagcggaaat tcgacaacct gactaaggct gagcgaggcg gactctccga gcttgacaag 3960
gctggcttca tcaagcggca gttggtcgaa acccgacaga taacgaagca cgttgcccag 4020
atacttgact cccgtatgaa caccaagtac gacgagaacg acaagctcat cagggaggtg 4080
aaggtcatta cccttaagtc caaactcgtc agcgactttc gtaaggactt ccagttctac 4140
aaggtgcgcg agatcaataa ctaccaccac gcacacgacg cctacctgaa cgcagtggtt 4200
ggaaccgcgt tgattaaaaa gtaccccaag ttggagtcgg agttcgttta cggggactac 4260
aaggtgtacg acgtcggaa gatgatcgcc aagtctgaag agtggagcg gaaagcaacc 4320
gccaagtatt tcttctatag caacatcatg aacttcttta aaaccgagat cacacttgcc 4380
aatggcgaga tccgtaagag gccgctgatc gagacaaatg gggagactgg cgagatcgtg 4440
tgggacaagg gccgcgactt cgcaaccgtt cggaaagtct tgtccatgcc tcaagtcaac 4500
atcgtcaaga agactgaggt gcaaacaggc gggtctcga aggagtccat actgcccaag 4560
aggaactcag acaagctcat agcacgcaaa aaagactggg atccaaagaa atacggcggg 4620
```

```
ttcgactcgc cgacagtcgc atactccgtg ttagtggtgg ctaaagtgga aaaggggaag  4680
tccaagaagc tcaagtccgt caaggagttg ctcgggatca ccattatgga acggtcctca  4740
ttcgagaaga atcccattga cttcctagag gcgaagggct acaaagaggt caaaaaggac  4800
ctaattatta agctccccaa gtattcactc ttcgaacttg aaaatggtcg taagcggatg  4860
ttggcaagcg ctggagagct tcagaagggg aacgagcttg cactgccttc caagtacgtg  4920
aacttcctgt acctcgcctc tcattacgag aagttgaagg gctcaccgga ggacaacgag  4980
cagaagcagt tgttcgtgga gcagcacaag cactacctcg acgagatcat tgagcagata  5040
agtgagttca gcaaacgggt gatccttgcc gacgctaacc tggacaaggt gctgagcgcc  5100
tacaacaagc acagagacaa gccgatccga gagcaagcgg agaacatcat acacctgttc  5160
accctcacga acctcggggc tcccgcagcc ttcaaatatt ttgacacgac catcgaccgt  5220
aaacgctaca ctagcacgaa ggaggtgctg gacgctaccc ttatccacca gtccatcacc  5280
ggcctgtacg agacgagaat cgacttgtcg cagctcggtg gtgacggatc taagaagaga  5340
agaattaaac aagattga                                                5358

SEQ ID NO: 72          moltype = DNA  length = 20
FEATURE                Location/Qualifiers
misc_feature           1..20
                       note = CRISPR spacer
source                 1..20
                       mol_type = other DNA
                       organism = synthetic construct
SEQUENCE: 72
cagatcacaa acttcaaatg                                              20

SEQ ID NO: 73          moltype = DNA  length = 20
FEATURE                Location/Qualifiers
misc_feature           1..20
                       note = CRISPR spacer
source                 1..20
                       mol_type = other DNA
                       organism = synthetic construct
SEQUENCE: 73
agccctcctt gcgctgcaag                                              20

SEQ ID NO: 74          moltype = DNA  length = 20
FEATURE                Location/Qualifiers
misc_feature           1..20
                       note = CRISPR spacer
source                 1..20
                       mol_type = other DNA
                       organism = synthetic construct
SEQUENCE: 74
gaaatcacgg ttgagtgtga                                              20

SEQ ID NO: 75          moltype = DNA  length = 133
FEATURE                Location/Qualifiers
source                 1..133
                       mol_type = other DNA
                       organism = Homo sapiens
SEQUENCE: 75
gtaagtatca aggttacaag acaggtttaa ggagaccaat agaaactggg cttgtcgaga  60
cagagaagac tcttgcgttt ctgataggca cctattggtc ttactgacat ccactttgcc  120
tttctctcca cag                                                     133

SEQ ID NO: 76          moltype = DNA  length = 99
FEATURE                Location/Qualifiers
source                 1..99
                       mol_type = other DNA
                       organism = Simian virus 40
SEQUENCE: 76
gtaagtttag tcttttgtc ttttatttca ggtcccggat ccggtggtgg tgcaaatcaa  60
agaactgctc tcagtggat gttgccttta cttctaggc                          99
```

OPTIMIZED CRISPR-Cas NUCLEASES AND BASE EDITORS AND METHODS OF USE THEREOF

STATEMENT OF PRIORITY

This application is a continuation application of U.S. patent application Ser. No. 17/078,576, filed on Oct. 23, 2020, which claims the benefit, under 35 U.S.C. § 119(e), of U.S. Provisional Application No. 62/925,422 filed on Oct. 24, 2019, the entire contents of which is incorporated by reference herein.

STATEMENT REGARDING ELECTRONIC FILING OF A SEQUENCE LISTING

A Sequence Listing in XML format, entitled 1499-8CT_ST26.xml, 250,749 bytes in size, generated on Jan. 23, 2023 and filed herewith, is hereby incorporated by reference into the specification for its disclosures.

FIELD OF THE INVENTION

This invention relates to codon optimized CRISPR-Cas nucleases and nucleic acid constructs encoding base editors comprising a CRISPR-Cas nuclease and a deaminase domain, wherein the nucleic acid constructs are optimized for expression in a plant. The invention further relates to methods of modifying nucleic acids using the nucleic acid constructs.

BACKGROUND OF THE INVENTION

Gene editing is the process of utilizing a site-directed nuclease to introduce variation at targeted genomic locations. The most widely utilized nuclease for gene editing, Cas9, can introduce mutations at a genomic region upstream of an NGG motif (e.g., PAM). These mutations generated are typically insertions or deletions of a few base pairs, but the final sequence achieved can be unpredictable. As a result, obtaining precise genomic alterations using Cas9 editing has been difficult, and for the most part, use of these tools has been for the removal of protein function. As an alternative to Cas9 gene editing, targeted base editing has recently been developed by fusing deaminase protein domains to a disabled nuclease. The most commonly used version for modifying cytosine residues, cytosine base editors (CBE), comprise an Apobec1 domain, which functions to deaminate the cytosine residues within a targeting window. In addition, the base editors can include uracil glycosylase inhibitor (UGI) domains to help facilitate the repair of the modification towards a non-cytosine base change. In mammalian systems, these modification tools have been engineered to produce a very specific cytosine to thymine (C→T) change, through multiple different base editor iterations. In contrast to mammalian systems, the use of base editor cassettes for gene modification in plants has been limited and their efficacy has been low. For example, with the exception of rice, use of CBE base editors in plants has provided low editing efficiency.

To make base editing more useful across a greater number of plant species, new base editing tools are needed.

SUMMARY OF THE INVENTION

Base editing can provide modifications of specific nucleotides within a targeting window. The type of change introduced is reliant on the type of nuclease introduced and the repair profile of the target organism. For example, cytosine base editors (CBEs) provide a base change from C→T and adenine base editors (ABEs) provide a base change from A→G. These base changes limit the type of modification that can be designed and recovered. Further, while base editing has been demonstrated in plants, the editing efficiency is low (e.g., base edits are recovered at low rates). The only plant species that has exhibited a high level of editing is rice; however, even for rice the amount of base editing recovered has been quite variable, from 0% to about 80%. In maize, base edits have been recovered at a low frequency of about 10% frequency, and for wheat the efficiency of editing is even lower at less than 2%. Currently, base editing in plants relies on the use of base editing gene cassettes employed in mammalian systems that are placed into a plant-compatible cloning vector. To enhance efficacy of base editor constructs in planta, the present invention provides base editor expression cassettes in which the components have been codon optimized to increase the efficiency of base editor activity in plants.

One aspect of the invention provides a nucleic acid construct encoding a CRISPR-Cas nuclease, wherein the CRISPR-Cas nuclease is codon optimized for expression in a plant and comprises the nucleotide sequence of any one of SEQ ID NOs:1-11 and 23-25.

A second aspect provides a nucleic acid construct encoding a CRISPR-Cas nuclease operably associated with a promoter, wherein the promoter is associated with an intron. In some embodiments, the nucleic acid construct encoding a CRISPR-Cas nuclease is operably associated with a promoter region, wherein the promoter region comprises an intron. In some embodiments, the CRISPR-Cas nuclease operably associated with a promoter/promoter region may be codon optimized for expression in a plant.

A third aspect of the invention provides a nucleic acid construct encoding a CRISPR-Cas nuclease and a deaminase domain (e.g, a base editor), wherein the CRISPR-Cas nuclease is codon optimized for expression in a plant, and optionally, the deaminase domain is codon optimized for expression in a plant. In some aspects, a nucleic acid construct of the invention encoding a base editor comprises the nucleotide sequence of any one of SEQ ID NOs: 12-22.

A fourth aspect of the invention provides a method of modifying a target nucleic acid, comprising contacting a cell or a cell free system comprising the target nucleic acid with: (a) a nucleic acid construct of the invention, or an expression cassette or vector comprising the same; and (b) a guide nucleic acid (e.g., CRISPR RNA, CRISPR DNA, crRNA, crDNA), under conditions, wherein the nucleic acid construct is expressed and forms a complex with the guide nucleic acid, the complex then hybridizing to the target nucleic acid, thereby modifying the target nucleic acid.

A fifth aspect of the invention provides a method of editing a target nucleic acid, comprising contacting a cell or a cell free system comprising the target nucleic acid with: (a) a nucleic acid construct encoding an optimized CRISPR-Cas nuclease of the invention and an adenine deaminase (e.g., a base editor), or an expression cassette or vector comprising the same; and (b) a guide nucleic acid, under conditions wherein the nucleic acid construct is expressed and the CRISPR-Cas nuclease forms a complex with the guide nucleic acid, the complex hybridizing to the target nucleic acid, wherein the adenine deaminase domain converts an adenosine (A) to a guanine (G) in the target nucleic acid, thereby editing the target nucleic acid to produce a mutation (e.g., a point mutation) in the target nucleic acid.

A sixth aspect of the invention provides a method of editing a target nucleic acid, comprising contacting a cell or a cell free system comprising the target nucleic acid with: (a) a nucleic acid construct encoding an optimized CRISPR-Cas nuclease of the invention and an cytosine deaminase (e.g., a base editor), or an expression cassette or vector comprising the same; and (b) a guide nucleic acid under conditions wherein the nucleic acid construct is expressed and the CRISPR-Cas nuclease forms a complex with the guide nucleic acid, the complex hybridizing to the target nucleic acid, wherein the cytosine deaminase domain converts a cytosine (C) to a thiamine (T) in the target nucleic acid, thereby editing the target nucleic acid to produce a (point) mutation.

The invention further provides expression cassettes and/or vectors comprising the nucleic acid constructs of the invention, and cells comprising polypeptides, fusion proteins and/or nucleic acid constructs of the invention. Additionally, the invention provides kits comprising the nucleic acid constructs of the invention and expression cassettes, vectors and/or cells comprising the same.

These and other aspects of the invention are set forth in more detail in the description of the invention below.

SEQUENCES

SEQ ID NOs:1-11 are exemplary nucleotide sequences encoding Cas9 nucleases of the invention codon optimized for use in plants.

SEQ ID NOs:12-22 and SEQ ID NOs: 69-71 are exemplary nucleotide sequences encoding base editors of the invention.

SEQ ID NOs: 23-25 are exemplary nucleotide sequences encoding Cas12a nucleases of the invention that are codon optimized for use in plants.

SEQ ID NOs:26-42 are example Cas12a amino acid sequences useful with this invention.

SEQ ID NOs:43-49 are example adenine deaminase amino acid sequences useful with this invention.

SEQ ID NOs:50-59 are example cytosine deaminase amino acid sequences useful with this invention.

SEQ ID NO:60 is an exemplary uracil-DNA glycosylase inhibitor (UGI) useful with this invention.

SEQ ID NO:61-63 are exemplary regulatory sequences encoding a promoter and intron.

SEQ ID NOs: 64-66 provide an example of a protospacer adjacent motif position for a Type V CRISPR-Cas12a nuclease.

SEQ ID NOs: 67-68 provide exemplary nucleotide sequences encoding non-natural Cas9 nucleases.

SEQ ID NOs: 69-71 provide exemplary nucleic acid constructs comprising codon optimized polynucleotides encoding base editors that include a CRISPR-Cas9 nuclease and an adenine deaminase domain.

SEQ ID NOs: 72-73 provide exemplary CRISPR spacers.

DETAILED DESCRIPTION

Figure 1:
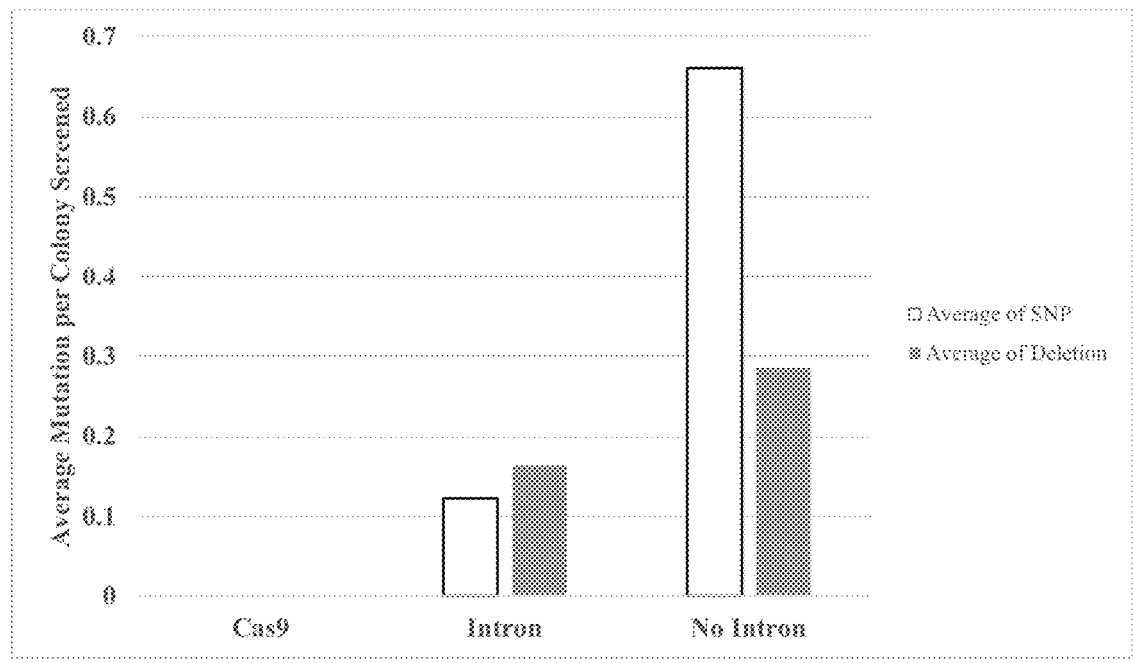
FIG. 1. Average mutation per colony screened. The number of SNPs or deletions was averaged across the total amount of colonies screened in each group.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild type Cas9 repeat, wild type Cas12a repeat, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2×(or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The polynucleotide and/or recombinant nucleic acid constructs of this invention can be codon optimized for expression. In some embodiments, the polynucleotides, nucleic acid constructs, expression cassettes, and/or vectors of the invention (comprising/encoding a base editor, e.g., CRISPR-Cas nuclease, deaminase domain, linkers) are codon optimized for expression in a plant (e.g., in a particular plant species). In some embodiments, the codon optimized nucleic acid constructs, polynucleotides, expression cassettes, and/ or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the nucleic acid constructs, polynucleotides, expression cassettes, and/ or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a CRISPR-Cas nuclease polypeptide or domain (e.g., Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 polypeptide or domain) and a polypeptide of interest (e.g., a nucleic acid-editing domain, a deaminase domain, an adenosine deaminase, a cytosine deaminase). A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or a peptide. In some embodiments, the linker is a peptide.

In some embodiments, a peptide linker useful with this invention may be about 4 to about 100 or more amino acids in length, for example, about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. In some embodiments, a peptide linker may be a GS linker.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NO:61, SEQ ID NO:62 or SEQ ID NO:63).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from *arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof. As a non-limiting example, a nucleic acid construct of the present invention may encode a base editor comprising an optimized CRISPR-Cas nuclease (e.g., SEQ ID NOs:1-11 or 23-25) and a deaminase, wherein the nucleic acid construct further comprises a promoter comprising/associated with an intron. As a further non-limiting example, a nucleic acid construct of the present invention may encode a base editor comprising an optimized CRISPR-Cas nuclease (e.g., SEQ ID NOs:1-11 or 23-25) and a deaminase, wherein the nuclease and/or the deaminase comprises one or more introns and optionally, the nucleic acid construct further comprises a promoter comprising/associated with an intron.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., encoding a base editor comprising a CRISPR-Cas nuclease and a deaminase domain), wherein the nucleic acid construct is operably associated with at least a control sequence (e.g., a promoter). Thus, some embodiments of the invention provide expression cassettes designed to express, for example, a nucleic acid construct of the invention (e.g., a nucleic acid construct of the invention encoding a base editor comprising a CRISPR-Cas nuclease and a deaminase domain, wherein the nucleic acid construct is optimized for expression in a plant).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to a gene encoding a CRISPR-Cas nuclease or a gene encoding a deaminase encoded by a nucleic acid construct of the invention, may be native to a host cell, or may be native to another source (e.g., foreign or heterologous to the promoter, to a gene encoding the CRISPR-Cas nuclease or a gene encoding the deaminase encoded by a nucleic acid construct of the invention, to a host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). Thus, for example, a target nucleic acid may be contacted with a nucleic acid construct of the invention encoding a base editor comprising a codon optimized CRISPR-Cas nuclease, and a guide nucleic acid, under conditions whereby the CRISPR-Cas nuclease is expressed, whereby the CRISPR-Cas nuclease forms a complex with the guide nucleic acid, and the complex hybridizes to the target nucleic acid, thereby modifying the target nucleic acid. In some embodiments, a target nucleic acid may be contacted with a nucleic acid construct of the invention encoding a base editor comprising a codon optimized CRISPR-Cas nuclease linked to a deaminase domain, and a guide nucleic acid, under conditions wherein the CRISPR-Cas nuclease and deaminase domain are expressed as a fusion protein, whereby the fusion protein forms a complex with the guide nucleic acid, and the complex hybridizes to the target nucleic acid, thereby modifying (editing) the target nucleic acid. As described herein, the target nucleic acid may be contacted with the nucleic acid constructs of the invention prior to, concurrently with, or after contact with the guide nucleic acid.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid.

"Introducing," "introduce," "introduced" (and grammatical variations thereof) in the context of a polynucleotide of interest means presenting a nucleotide sequence of interest (e.g., polynucleotide, a nucleic acid construct, and/or a guide nucleic acid) to a host organism or cell of said organism (e.g., host cell; e.g., a plant cell) in such a manner that the nucleotide sequence gains access to the interior of a cell. Thus, for example, a nucleic acid construct of the invention encoding a base editor optimized for expression in a plant as described herein and guide nucleic acid may be introduced into a cell of an organism, thereby transforming the cell with the base editor and guide nucleic acid.

The term "transformation" as used herein refers to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., encoding a CRISPR-Cas nuclease codon optimized for plant expression (e.g., SEQ ID NOs:1-11, 23-25) and/or encoding a base editor comprising a codon optimized CRISPR-Cas nuclease and a deaminase domain (e.g., a fusion protein comprising the CRISPR-Cas nuclease linked to the deaminase domain) (e.g., SEQ ID NOs:12-22) may be transiently introduced into a cell with a guide nucleic acid and as such, no DNA maintained in the cell.

A nucleic acid construct of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid constuct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:228-2308 (2013)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence can be incorporated into a plant, for example, as part of a breeding protocol.

Studies utilizing base editing in plants are limited. Zong et al. examined cytosine base editing (CBE) activity in rice, wheat, and maize (*Nature Biotechnol.* 35:438-440 (2017)) but found that while high base editing activity could be found in rice, the amount of activity in wheat and maize was quite low. Additionally, the only base editing architectures that have been utilized in plants are based on the base editing 1 or base editing 3 variants. In contrast, the present invention uses base editing 4 architecture, which comprises an additional UGI domain and longer linker sequence between the APOBEC1 domain and nuclease. See, e.g., Rees et al. *Nat. Rev. Genet.* 19:770-788 (2018).

In some embodiments, the present invention provides nucleic acid constructs encoding CRISPR-Cas nucleases codon optimized for expression in a plant, for example, SEQ ID NOs:1-11 and 23-25. In some embodiments, the nucleic acid constructs of the invention comprise base editors comprising a CRISPR-Cas nuclease and a deaminase domain, wherein the CRISPR-Cas nuclease, and optionally, the deaminase sequence, is/are codon optimized for expression in a plant. In some embodiments, a base editor of the invention can comprise, for example, a nucleotide sequence of any one of SEQ ID NOs:12 to 22.

In some embodiments, a nucleic acid construct encoding a CRISPR-Cas nuclease or base editor of the invention may be operably linked to at least one regulatory sequence, optionally, wherein the at least one regulatory sequence may be codon optimized for expression in a plant. In some embodiments, the at least one regulatory sequence may be, for example, a promoter, an operon, a terminator, or an enhancer. In some embodiments, the at least one regulatory sequence may be a promoter. In some embodiments, the regulatory sequence may be an intron. In some embodiments, the at least one regulatory sequence may be, for example, a promoter operably associated with an intron or a promoter region comprising an intron. In some embodiments, the at least one regulatory sequence may be, for example a ubiquitin promoter and its associated intron (e.g., *Medicago truncatula* and/or *Zea mays* and their associated introns). In some embodiments, the at least one regulatory sequence may be a terminator nucleotide sequence and/or an enhancer nucleotide sequence.

In some embodiments, the present invention provides a nucleic acid construct encoding a CRISPR-Cas nuclease (e.g., a Type I, Type II, Type III, Type IV, Type V, or Type VI CRISPR-Cas nuclease as described herein) operably associated with a promoter region, wherein the promoter region comprises an intron, optionally wherein the promoter region may be a ubiquitin promoter and intron (e.g., a *Medicago* or a maize ubiquitin promoter and intron, e.g., SEQ ID NOs:61-63). In some embodiments, the CRISPR-Cas nuclease operably associated with a promoter region comprising an intron may be codon optimized for expression in a plant.

In some embodiments, a nucleic acid construct of the invention encoding a CRISPR-Cas nuclease may further encode one or more polypeptides of interest, optionally wherein the one or more polypeptides of interest may be codon optimized for expression in a plant.

A polypeptide of interest useful with this invention can include, but is not limited to, a polypeptide or protein domain having deaminase activity, nickase activity, recombinase activity, transposase activity, methylase activity, glycosylase (DNA glycosylase) activity, glycosylase inhibitor activity (e.g., uracil-DNA glycosylase inhibitor (UGI)), demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity. In some embodiments, the polypeptide of interest is a deaminase (e.g., an adenine deaminase, a cytosine deaminase). In some embodiments, the polypeptide of interest is a Fok1 nuclease, or a uracil-DNA glycosylase inhibitor. When encoded in the polynucleotide of interest, the encoded polypeptide or protein domain may be codon optimized for expression in a plant.

In some embodiments, a nucleic acid construct of the invention encoding a base editor comprising a CRISPR-Cas nuclease and a deaminase domain (e.g., encoding a fusion protein comprising a CRISPR-Cas nuclease and a deaminase domain) may further encode a polypeptide of interest, optionally wherein the polypeptide of interest may be codon optimized for expression in a plant.

A CRISPR-Cas nuclease useful with this invention may be any CRISPR-Cas nuclease functional with a deaminase polypeptide or deaminase domain (e.g., functional with a cytosine deaminase domain and/or an adenine deaminase domain). A CRISPR-Cas nuclease can include, but is not limited to, Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3'', Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5.

In some embodiments, a CRISPR-Cas nuclease useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas nuclease having a mutation in its nuclease active site, and therefore, no longer comprising nuclease activity, is commonly referred to as "dead," e.g., dCas. In some embodiments, a CRISPR-Cas nuclease domain or polypeptide having a mutation in its nuclease active site may have impaired activity or reduced activity as compared to the same CRISPR-Cas nuclease without the mutation.

A CRISPR Cas9 polypeptide or CRISPR Cas9 domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes*, *S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Exemplary Cas9 nucleases of the present invention include the amino acid sequence of any one of SEQ ID NOs:1-11, 67 or 68 (e.g., SEQ ID NOs:1, 2, 3, 4, 5, 6, 7, 8, 9, 10, 11 and/or 67 or 68) or a polynucleotide encoding the same.

Cas12a is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a polypeptide or CRISPR Cas12a domain useful with this invention may be any known or later identified Cas12a nuclease (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity.

In some embodiments, a Cas12a polypeptide/domain that may be optimized according to the present invention can include, but is not limited to, the amino acid sequence of any one of SEQ ID NOs:26-42 (e.g., SEQ ID NOs: 26, 27, 28, 29, 30, 31, 32, 33, 34, 35, 36, 37, 38, 39, 40, 41, or 42), or a polynucleotide encoding the same. In some embodiments, example optimized Cas12a polypeptides of the invention comprise the amino acid sequence of any one of SEQ ID NOs:23-25 (e.g., SEQ ID NOs:23, 24, or 25), or a polynucleotide encoding the same.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), an hAID and evolved versions of the same. In some embodiments, the cytosine deaminase may be an APOBEC1 deaminase having the amino acid sequence of SEQ ID NO:50, SEQ ID NO:55 or SEQ ID NO:57. In some embodiments, the cytosine deaminase may be an APOBEC3A deaminase having the amino acid sequence of SEQ ID NO:51. In some embodiments, the cytosine deaminase may be an CDA1 deaminase, optionally a CDA1 having the amino acid sequence of SEQ ID NO:52 or SEQ ID NO:54. In some embodiments, the cytosine deaminase may be a FERNY deaminase, optionally a FERNY having the amino acid sequence of SEQ ID NO:53 or SEQ ID NO:56. In some embodiments, the cytosine deaminase may be an hAID deaminase, optionally a hAID deaminase having the amino acid sequence of SEQ ID NO:58 or SEQ ID NO:59. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NOs:50-59 (e.g., at least 80%, at least 85%, at least 90%, at least 92%, at least 95%, at least 96%, at least 97%, at least 98%, at least 99%, or at least 99.5% identical to the amino acid sequence of SEQ ID NOs:50-59). In some embodiments, a polynucleotide encoding a cytosine deaminase may be codon optimized for expression in an organism and the codon optimized polypeptide may be about 70% to 99.5% identical to the reference polynucleotide.

In some embodiments, a base editor of this invention comprising a CRISPR-Cas nuclease and a cytosine deaminase may further comprise a polypeptide of interest. In some embodiments, the polypeptide of interest may be a uracil glycosylase inhibitor (UGI) (e.g., uracil-DNA glycosylase inhibitor) polypeptide/domain. In some embodiments, a nucleic acid construct encoding an optimized CRISPR-Cas nuclease of this invention and a cytosine deaminase domain (e.g., encoding a fusion protein comprising a CRISPR-Cas nuclease and a cytosine deaminase domain) may further encode a uracil-DNA glycosylase inhibitor (UGI), optionally wherein the UGI is codon optimized for expression in a plant. In some embodiments, the invention provides a fusion protein comprising a CRISPR-Cas nuclease, a cytosine deaminase domain, and a UGI and/or one or more polynucleotides encoding the same, optionally wherein the one or more polynucleotides may be codon optimized for expression in a plant.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO: 60 or a polypeptide having about 70% to about 99.5% identity to the amino acid sequence of SEQ ID NO:60 (e.g., at least 80%, at least 85%, at least 90%, at least 92%, at least 95%, at least 96%, at least 97%, at least 98%, at least 99%, or at least 99.5% identical to the amino acid sequence of SEQ ID NO:60). For example, in some embodiments, a UGI domain may comprise a fragment of the amino acid sequence of SEQ ID NO:60 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:60. In some embodiments, a UGI domain may be a variant of a known UGI (e.g., SEQ ID NO:60) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be codon optimized for expression in a plant and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally-occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 16, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:43. In some embodiments, a mutated/evolved *E. coli* TadA* comprises the amino acid sequence of SEQ ID NOs:44-49 (e.g., SEQ ID NOs: 44, 45, 46, 47, 48 or 49). In some embodiments, a polynucleotide encoding a TadA/TadA* may be codon optimized for expression in a plant.

The nucleic acid constructs of the invention encoding a base editor comprising a CRISPR-Cas nuclease domain and a deaminase domain may be used in combination with a guide RNA (gRNA, CRISPR array, CRISPR RNA, crRNA), designed to function with the encoded CRISPR-Cas nuclease domain, to modify a target nucleic acid. A guide nucleic acid useful with this invention comprises a spacer sequence and a repeat sequence. The guide nucleic acid is capable of forming a complex with the CRISPR-Cas nuclease domain encoded and expressed by the nucleic acid construct of the invention and the spacer sequence is capable of hybridizing to a target nucleic acid, thereby guiding the nucleic acid construct (e.g., the CRISPR-Cas nuclease, the CRISPR-Cas nuclease and the deaminase domain (e.g., a base editor of the invention)) to the target nucleic acid, wherein the target nucleic acid may be modified (e.g., cleaved or edited) or modulated (e.g., modulating transcription) by the encoded deaminase domain and/or polypeptide of interest.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas nuclease encoded by the nucleic acid constructs of the invention that encode a base editor. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide RNA, crRNA).

In some embodiments, a repeat sequence comprises, consists essentially of, or consists of at least 10 nucleotides depending on the particular repeat and whether the guide RNA comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprises a pseudoknot-like structure at its 5' end (e.g., "handle").

A "spacer sequence" as used herein is a nucleotide sequence that is complementary to a target nucleic acid (e.g., target DNA) (e.g, protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 23 nucleotides in length.

In some embodiments, the 5' region of a spacer sequence of a guide RNA may be identical to a target DNA, while the 3' region of the spacer may be substantially complementary to the target DNA (e.g., Type V CRISPR-Cas), or the 3' region of a spacer sequence of a guide RNA may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of an organism's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide RNA of this invention. A region useful for a CRISPR-Cas system, known as the protospacer adjacent motif (PAM), is located adjacent to the spacer (or target) sequence. These PAM DNA sequences are typically described by referencing their sequence and location with respect to the non-target strand of the CRISPR complex. PAM sequences can be either 3' (e.g., Type V CRISPR-Cas system) or 5' (e.g., Type II CRISPR-Cas system) to the end of the protospacer sequence. A target region (also referred to as the protospacer) may be selected from any region of at least 15 consecutive nucleotides (e.g., 15, 16, 17, 18, 19, 20, 21, 22, 23, 24, 25, 26, 27, 28, 29, 30 or more than 30 nucleotides, and the like) located adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide RNAs, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention. In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct that is codon optimized for expression in plants and comprising a CRISPR-Cas nuclease and a deaminase domain (e.g., a fusion protein)) may be comprised on the same or on a separate expression cassette or vector from that comprising the guide nucleic acid. When the nucleic acid construct encoding a base editor is comprised on a separate expression cassette or vector from that comprising the guide nucleic acid, a target nucleic acid may be contacted with (e.g., provided with) the expression cassette or vector encoding the base editor prior to, concurrently with, or after the expression cassette comprising the guide nucleic acid is provided (e.g., contacted with the target nucleic acid).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors encoding the

```
5'-NNNNNNNNNNNNNNNNNNNN-3'  RNA Spacer (SEQ ID NO: 64)
   ||||||||||||||||||||
3'-AAANNNNNNNNNNNNNNNNNNNN-5'  Target strand (SEQ ID NO: 65)
   ||||
5'-TTTNNNNNNNNNNNNNNNNNNNN-3'  Non-target strand (SEQ ID NO: 66)
``` same CRISPR-Cas nuclease and/or deaminase domain but which have not been codon optimized for expression in a plant.

In some embodiments, the invention provides cells comprising one or more polynucleotides, guide nucleic acids, nucleic acid constructs, expression cassettes or vectors of the invention.

The nucleic acid constructs of the invention (e.g., a construct that is codon optimized for expression in plants and comprising a codon optimized CRISPR-Cas nuclease and/or a codon optimized CRISPR-Cas nuclease and a deaminase domain (e.g., a fusion protein)) and expression cassettes/vectors comprising the same may be used for modifying target nucleic acids and/or their expression.

In some embodiments, a nucleic acid construct of the invention may encode a codon optimized CRISPR-Cas nuclease linked to a deaminase domain (a base editor) for use in base editing a target nucleic acid in a plant, wherein the codon optimized CRISPR-Cas nuclease can be any Cas nuclease (e.g., a codon optimized Cas12a nuclease (e.g., SEQ ID NOs:23-25) or a codon optimized Cas9 nuclease (e.g., SEQ ID NOs:1-11) and the deaminase domain is a cytosine or an adenosine deaminase domain, wherein the codon optimization is for expression in a plant. In some embodiments, the nucleic acid constructs comprise promoters, introns and other regulatory sequences as described herein.

When used in combination with guide nucleic acids, the nucleic acid constructs of the invention of the invention may be used to modify a target nucleic acid. A target nucleic acid may be contacted with a nucleic acid construct of the invention prior to, concurrently with or after contacting the target nucleic acid with the guide nucleic acid. In some embodiments, the nucleic acid constructs of the invention and a guide nucleic acid may be comprised in the same expression cassette or vector and therefore, a target nucleic acid may be contacted concurrently with the nucleic acid constructs of the invention and guide nucleic acid. In some embodiments, the nucleic acid constructs of the invention and a guide nucleic acid may be in different expression cassettes or vectors and thus, a target nucleic acid may be contacted with the nucleic acid constructs of the invention prior to, concurrently with, or after contact with a guide nucleic acid.

In some embodiments, a method of modifying a target nucleic acid is provided, the method comprising contacting a cell or a cell free system comprising the target nucleic acid with (a) a nucleic acid construct encoding a codon optimized CRISPR-Cas nuclease of the invention, and/or an expression cassette or vector comprising the same, and (b) a guide nucleic acid (e.g., CRISPR RNA, CRISPR DNA, crRNA, crDNA), under conditions whereby the nucleic acid construct is expressed and produces the codon optimized CRISPR-Cas nuclease, which forms a complex with the guide nucleic acid, and wherein the complex hybridizes to the target nucleic acid, thereby modifying the target nucleic acid in the cell or cell free system. In some embodiments, the codon optimized CRISPR-Cas nuclease comprises the nucleotide sequence of any one of SEQ ID NOs:1 to 11 and/or SEQ ID NOs:23-25 or any combination thereof.

In some embodiments, a method of modifying a target nucleic acid is provided, the method comprising contacting a cell or a cell free system comprising the target nucleic acid with (a) a nucleic acid construct encoding a base editor of the invention comprising a codon optimized CRISPR-Cas nuclease and deaminase domain, and/or an expression cassette or vector comprising the same, and (b) a guide nucleic acid (e.g., CRISPR RNA, CRISPR DNA, crRNA, crDNA), under conditions whereby the nucleic acid construct is expressed to produce the base editor (e.g., the CRISPR-Cas nuclease and deaminase domain), which forms a complex with the guide nucleic acid (e.g., the codon optimized CRISPR-Cas nuclease complexes with the guide nucleic acid), and wherein the complex hybridizes to the target nucleic acid, thereby modifying the target nucleic acid in the cell or cell free system. In some embodiments, the base editor of the invention comprising a CRISPR-Cas nuclease and a deaminase domain comprises the nucleotide sequence of any one of SEQ ID NOs:12-22 or 69-71, or any combination thereof.

In some embodiments, a method of modifying a target nucleic acid in a plant is provided, the method comprising contacting a cell of the plant comprising the target nucleic acid with (a) a nucleic acid construct encoding a codon optimized CRISPR-Cas nuclease of the invention, and/or an expression cassette or vector comprising the same, and (b) a guide nucleic acid (e.g., CRISPR RNA, CRISPR DNA, crRNA, crDNA), under conditions whereby the nucleic acid construct is expressed to produce the CRISPR-Cas nuclease, which forms a complex with the guide nucleic acid, and the complex hybridizes to the target nucleic acid, thereby modifying the target nucleic acid in the plant. In some embodiments, the codon optimized CRISPR-Cas nuclease comprises the nucleotide sequence of any one of SEQ ID NOs:1 to 11 and/or SEQ ID NOs:23-25, or any combination thereof. In some embodiments, a plant cell modified by the methods of this invention may be regenerated into a plant and/or a plant part.

In some embodiments, a method of modifying a target nucleic acid in a plant is provided, the method comprising contacting a cell of the plant comprising the target nucleic acid with (a) a nucleic acid construct encoding a base editor of the invention comprising a CRISPR-Cas nuclease and a deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, thereby modifying the target nucleic acid in the plant. In some embodiments, the base editor of the invention comprising a CRISPR-Cas nuclease and a deaminase domain comprises the nucleotide sequence of any one of SEQ ID NOs:12-22 or 69-71, or any combination thereof. In some embodiments, a plant cell modified by the methods of this invention may be regenerated into a plant and/or a plant part.

In some embodiments, a method of editing a target nucleic acid is provided, the method comprising contacting a cell or a cell free system comprising the target nucleic acid with: (a) a nucleic acid construct of the invention encoding a base editor comprising a codon optimized CRISPR-Cas nuclease and adenosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, and the adenine deaminase domain converts an adenosine (A) to a guanine (G) in the target nucleic acid, thereby editing the target nucleic acid to produce a (point) mutation in the target nucleic acid.

In some embodiments, a method of editing a target nucleic acid in a plant is provided, the method comprising contacting a cell of the plant comprising the target nucleic acid with: (a) a nucleic acid construct of the invention encoding a base editor comprising a codon optimized CRISPR-Cas nuclease and adenosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, and the adenine deaminase domain converts an adenosine (A) to a guanine (G) in the target nucleic acid, thereby editing the target nucleic acid to produce a mutation (e.g., point mutation) in the target nucleic acid in the plant. In some embodiments, a plant cell modified by the methods of this invention may be regenerated into a plant and/or a plant part.

In some embodiments, a method of editing a target nucleic acid is provided, the method comprising contacting a cell or a cell free system comprising the target nucleic acid with: (a) a nucleic acid construct of the invention encoding a base editor comprising a codon optimized CRISPR-Cas nuclease and cytosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid and the cytosine deaminase domain converts a cytosine (C) to a thiamine (T) in the target nucleic acid, thereby editing the target nucleic acid to produce a (point) mutation.

In some embodiments, a method of editing a target nucleic acid is provided, the method comprising contacting a cell or a cell free system comprising the target nucleic acid with: (a) a nucleic acid construct of the invention encoding a base editor comprising the nucleotide sequence of any one of SEQ ID NOs:12-22 or 69-71, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid and the cytosine deaminase domain converts a cytosine (C) to a thiamine (T) in the target nucleic acid, thereby editing the target nucleic acid to produce a (point) mutation.

In some embodiments, a method of editing a target nucleic acid in a plant is provided, the method comprising contacting a cell of the plant comprising the target nucleic acid with: (a) a nucleic acid construct of the invention encoding a base editor comprising a codon optimized CRISPR-Cas nuclease and cytosine deaminase domain, and/or an expression cassette or vector comprising the same, and (b) a guide nucleic acid, under conditions whereby the nucleic acid construct is expressed to produce the base editor, which forms a complex with the guide nucleic acid, and wherein the complex hybridizes to the target nucleic acid and the cytosine deaminase domain converts a cytosine (C) to a thiamine (T) in the target nucleic acid, thereby editing the target nucleic acid to produce a (point) mutation in the target nucleic acid in the plant. In some embodiments, a plant cell modified by the methods of this invention may be regenerated into a plant and/or plant part.

In some embodiments, a method of editing a target nucleic acid in a plant is provided, the method comprising contacting a cell of the plant comprising the target nucleic acid with: (a) a nucleic acid construct of the invention encoding a base editor comprising the nucleotide sequence of any one of SEQ ID NOs:12-22 or 69-71, and/or an expression cassette or vector comprising the same, and (b) a guide nucleic acid, under conditions whereby the nucleic acid construct is expressed to produce the base editor, which forms a complex with the guide nucleic acid, and wherein the complex hybridizes to the target nucleic acid and the cytosine deaminase domain converts a cytosine (C) to a thiamine (T) in the target nucleic acid, thereby editing the target nucleic acid to produce a (point) mutation in the target nucleic acid in the plant. In some embodiments, a plant cell modified by the methods of this invention may be regenerated into a plant and/or plant part.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a codon optimized CRISPR-Cas nuclease and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a codon optimized CRISPR-Cas nuclease and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt transcription factor binding; and/or generation of point mutations in genomic DNA to disrupt splice junctions.

A target nucleic acid of any plant or plant part may be modified (e.g., mutated, e.g., base edited, cleaved, nicked, etc.) using the nucleic acid constructs of the invention (e.g., SEQ ID NOs:1-25 or 69-71). Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, *miscanthus, arundo*, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

The present invention further comprises a kit or kits to carry out the methods of this invention. A kit of this invention can comprise reagents, buffers, and apparatus for mixing, measuring, sorting, labeling, etc., as well as instructions and the like as would be appropriate for modifying a target nucleic acid.

In some embodiments, the invention provides a kit comprising one or more nucleic acid constructs of the invention (e.g., SEQ ID NOs:1-25 or 69-71), and/or expression cassettes and/or vectors comprising the same, with optional instructions for the use thereof. In some embodiments, a kit may further comprise a CRISPR-Cas guide nucleic acid (corresponding to the CRISPR-Cas nuclease encoded by the polynucleotide of the invention) and/or expression cassette and/or vector comprising the same. In some embodiments, the guide nucleic acid may be provided on the same expression cassette and/or vector as a nucleic acid construct of the invention. In some embodiments, the guide nucleic acid may be provided on a separate expression cassette or vector from that comprising the nucleic acid construct of the invention.

Accordingly, in some embodiments, kits are provided comprising a nucleic acid construct comprising (a) a polynucleotide encoding a base editor as provided herein and (b) a promoter that drives expression of the polynucleotide of (a). In some embodiments, the kit may further comprise a nucleic acid construct encoding a guide nucleic acid, wherein the construct comprises a cloning site for cloning of a nucleic acid sequence identical or complementary to a target nucleic acid sequence into backbone of the guide nucleic acid.

In some embodiments, the nucleic acid construct of the invention encoding the base editor may be an mRNA that may encode one or more introns within the encoded base editor. In some embodiments, the nucleic acid construct of the invention encoding a base editor, and/or an expression cassette and/or vector comprising the same, may further encode one or more selectable markers useful for identifying transformants (e.g., a nucleic acid encoding an antibiotic resistance gene, herbicide resistance gene, and the like).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Polynucleotides encoding a base editor that comprises a CRISPR-Cas nuclease and either a cytosine deaminase or an adenine deaminase were generated (e.g., SEQ ID NOs:12 to 22). The polynucleotides that were generated are codon optimized for expression in soybean or corn.

In maize, six different optimized polynucleotides encoding base editors that include a CRISPR-Cas9 nuclease and a cytosine deaminase domain are provided, and in soybean, five different optimized polynucleotides encoding base editors are provided. The optimizations were placed behind a plant-specific promoter and transformed into plants via *agrobacterium* mediated transformation protocols.

TABLE 1

Listing of the optimized base editors

| Coding sequence optimized version | Plant Type | SEQ ID NO: | Cas 9 SEQ ID NO |
|---|---|---|---|
| Mon_GS_V1 | Monocot | 12 | 1 |
| Mon_GS_V2 | Monocot | 13 | 2 |
| Mon-GS_V3 | Monocot | 14 | 3 |
| Mon_BY_V1 | Monocot | 15 | 4 |
| Mon_BY_V2 | Monocot | 16 | 5 |
| Mon_BY_V3 | Monocot | 17 | 6 |
| Di_GS_V1 | Dicot | 18 | 7 |
| Di_GS_V2 | Dicot | 19 | 8 |
| Di_GS_V3 | Dicot | 20 | 9 |
| Di_BY_V1 | Dicot | 21 | 10 |
| Di_BY_V2 | Dicot | 22 | 11 |

To examine the amount of base editing achievable with different optimizations, target regions were chosen that contained cytosine residues within a known targeting region (13-17 bp upstream of the PAM sequence). Specifically, the target nucleic acids that were chosen for maize are in the genes CenH3 and glossy2 (gl2). In soybean, the target nucleic acid that was chosen is in the Mir1509 gene.

TABLE 2

Guide nucleic acids

| Guide # | Target | Protospacer |
|---|---|---|
| PWg090001 | gl2 | CAGATCACAAACTTCAAATG |
| PWg090002 | ZmCENH3 | AGCCCTCCTTGCGCTGCAAG |
| PWg090005 | MIR1509 | GAAATCACGGTTGAGTGTGA |

The constructs comprising the codon optimized polynucleotides and the guides comprising the spacers targeting the target nucleic acids were introduced into soybean and maize plants using *Agrobacterium* transformation methods as known in the art.

Following transformation and regeneration of the corn and soybean plantlets, leaf tissues were sampled from each plant and editing efficiency was measured via amplicon sequencing followed by next generation sequencing. Bioinformatic analysis of the sequencing results examined the genetic region targeted by the nuclease to determine if the targeted cytosine residues had been converted to thymine residues. Plasmid sequencing was performed using the PlexWell service from seqWell.

When the codon optimizations were introduced to plants through *Agrobacterium* transformation, the amount of base editing that resulted differed between the different targets and optimizations. Notably, at the CenH3 target, which was previously reported to have a 10% editing efficiency, showed an overall editing efficiency of over 25%. Editing efficiency is measured as the number of plants showing at least 10% of reads with a single edit divided by the total number of plants exposed to the editing reagent (Table 3). At the gl2 target in corn, overall editing efficiency was over 60% with four of six optimizations obtaining over 80% editing efficiency.

TABLE 3

Editing efficiency of the plant optimized base editors in maize and soybean. The optimization column includes entries for 'Cas9', which is a baseline, unoptimized version of the Cas9 protein.

| Crop | Target | Construct | Optimization | n. Total | Edit. BE | Edit. Efficiency |
|---|---|---|---|---|---|---|
| Corn | gl2 | pWISE27 | GS-V1 | 94 | 79 | 84% |
| Corn | gl2 | pWISE30 | GS-V2 | 63 | 47 | 75% |
| Corn | gl2 | pWISE33 | GS-V3 | 75 | 45 | 60% |
| Corn | gl2 | pWISE36 | Cas9 | 67 | 0 | 0% |
| Corn | gl2 | pWISE179 | BY-V1 | 21 | 17 | 81% |
| Corn | gl2 | pWISE180 | BY-V2 | 91 | 77 | 85% |
| Corn | gl2 | pWISE181 | BY-V3 | 41 | 34 | 83% |
| Corn | ZmCenH3 | pWISE28 | GS-V1 | 118 | 46 | 39% |
| Corn | ZmCenH3 | pWISE34 | GS-V3 | 46 | 12 | 26% |
| Corn | ZmCenH3 | pWISE189 | BY-V1 | 24 | 12 | 50% |
| Corn | ZmCenH3 | pWISE190 | BY-V2 | 90 | 33 | 37% |
| Corn | ZmCenH3 | pWISE191 | BY-V3 | 6 | 4 | 67% |
| Corn | ZmCENH3 | pWISE28 | GS-V1 | 118 | 46 | 39% |
| Corn | ZmCENH3 | pWISE31 | GS-V2 | 49 | 23 | 57% |
| Corn | ZmCENH3 | pWISE37 | Cas9 | 5 | 1 | 20% |
| Soy | mir1509 | pWISE39 | GS-V1 | 156 | 0 | 0% |
| Soy | mir1509 | pWISE41 | GS-V2 | 19 | 0 | 0% |
| Soy | mir1509 | pWISE45 | Cas9 | 232 | 0 | 0% |
| Soy | mir1509 | pWISE182 | BY-V1 | 12 | 10 | 83% |
| Soy | mir1509 | pWISE183 | BY-V2 | 13 | 6 | 46% |

Example 2

In Example 1, different promoters were used to drive the base editing cassettes. As indicated in Table 3, in soy, the ubiquitin2 promoter, containing the native intron from the ubiquitin2 gene, from *Medicago truncatula* was used to drive cassette expression. In the case of GS-V1, GS-V2 and unoptimized Cas9, no edits were obtained. For BY-V1 and BY-V2, edits were obtained, however, the number of edits was unsatisfactory.

A third set of constructs were tested which comprised a tandem viral promoter driving the base editing cassette. The viral promoter has known leaky expression in prokaryotic systems. Complete plasmid sequencing of the vectors recovered after *Agrobacterium* and *E. coli* propagations consistently revealed C->T base changes. Indels could also be observed in some of the vectors with this leaky prokaryotic expression. These changes were found only in the viral promoter constructs lacking introns in the coding sequence of the cytosine base editor. It is interpreted that leaky expression in the prokaryotic system is leading to off-site editing of the plasmids and very likely the prokaryotic genome. This mutational activity is likely leading to construct instability in the prokaryotic systems.

Thus, a fourth set of constructs were tested utilizing the same MtUbq2 promoter but with an addition of an intron. The data from these tests are shown in Table 4.

TABLE 4

Editing efficiency in soy when a promoter region comprising an intron is used

| Crop | Target | Construct | Optimization | n. Total | Edit. BE | Edit. Efficiency |
|---|---|---|---|---|---|---|
| Soy | mir1509 | pWISE652 | GS-V1 + Intron | 30 | 2 | 7% |
| Soy | mir1509 | pWISE653 | GS-V2 + Intron | 30 | 10 | 33% |
| Soy | mir1509 | pWISE655 | BY-V1 + Intron | 50 | 26 | 52% |

In the case of GS-V1, while the editing efficiency remained low at 7%, the same construct without an intron did not make any edits. For GS-V2, an editing efficiency of 33% was achieved. For BY-V1, while the editing efficiency decreased from 83% to 52%, there was a 250% increase in the number of edits made, indicating a much better editing system.

Example 3

As a further means of improving editing efficiency and to prevent leaky expression in the prokaryotic system, constructs can be made utilizing an additional intron in either the APOBEC/deaminase domain or the UGI domain.

The nucleic acid constructs of the invention provide precision modification of plants through base editing. Prior to this work, the ability to confer specific base changes was limited by the low efficiency of the editing reagent. As a result, large quantities of starting material were required to generate plants with a desired mutation/genotype. However, the nucleic acid constructs provided by the present invention, now provide base editing at consistently higher levels than previously achievable.

Example 4

When assembling constructs containing a cytosine deaminase domain, Apobec1 and Apobec3a (A3A), instability was observed in the resulting clones in the form of mutant sequences. The most prominent change observed were C>T changes in the plasmid sequence. Also observed were large deletions in the plasmid, and in particular, deletions that disrupted the deaminase itself. The prevalence of mutations in the deaminase suggests a selection for such mutations and therefore likelihood that the deaminase may be cytotoxic in the bacteria.

Introns for Improving Stability

The stability of the base editor constructs designed for use with Cas9 was improved by utilizing a promoter, the Medicago ubiquitin 2 promoter (MtUbq2, SEQ ID NO:63), which contains an intron at the 3' end following the promoter and 5' UTR.

The Medicago ubiquitin intron, which cannot be excised by prokaryotes, prevents the downstream deaminase from being expressed, and therefore, reduces or prevents construct instability. Constructs that utilized the MtUbq2 promoter to drive expression of a cytosine base editor (APOBE1) (see, e.g., SEQ ID NOs:12-22), as well as those that utilize a constitutive tandem viral promoter, were transformed into E. coli and then sequenced by next generation sequencing. The resulting sequence was aligned to the reference sequence and the number of SNPs or deletions was tabulated for each construct. A total of 10 colonies for a standard Cas9 construct, 49 colonies having the base editor driven by MtUbq2 containing an intron, and 56 colonies having the base editor without an intron were screened. As seen in Table 5 and FIG. 1, the number of mutations observed is lower when an intron is present proceeding the editor.

TABLE 5

Sum of SNP and Deletions in base editor constructs when compared to nuclease vector control.

| Editor | Sum of SNP | Sum of Deletion | Colonies Counted |
|---|---|---|---|
| Cas9 Nuclease | 0 | 0 | 10 |
| Cytosine Base Editor with Intron | 6 | 8 | 49 |
| Cytosine Base Editor without Intron | 37 | 16 | 56 |

Cas12a Cytosine Base Editor Comprising an Intron in an A3A Deaminase (APOBEC3A)

The ability to assemble plasmids that match the originally intended sequence (i.e., a base editor construct of the invention, for example, but not limited to, SEQ ID NOs:12-22, that have not been edited by the cytosine deaminase in the construct) and that contain base editors is greatly impaired by instability caused by the deaminase domain. To assist with the assembly of a cytosine base editor for testing in a human cell system, a human chimeric intron (GTAAGTAT-CAAGGTTACAAGACAGGTTTAAGGAGAC-CAATAGAAACTGG GCTTGTCGAGACAGAGAA-GACTCTTGCGTTTCTGATAGGCACCTATTGGTCTTAC TGACATCCACTTTGCCTTTCTCTCCACAG) (SEQ ID NO:75) comprising the 5'-donor site from the first intron of the human β-globin gene and the branch and 3'-acceptor site from the intron that is between the leader and the body of an immunoglobulin gene heavy chain variable region (see, e.g., Younis et al. *Mol. Cell. Biol.* 30:1718-1728 (2010)) was placed into the active site of the human A3A deaminase. Specifically, the intron was placed 152 bases after the start of the intron coding sequence, which causes a premature stop codon and prevents further translation of the editor unless the intron sequence is removed.

When the assembly of the full base editor construct containing the A3A deaminase was performed, the ability to recover the desired clones was assessed. In this case, the assembly places the editor into a full transformation backbone, so that all of the components are put together at once. A fragment that contained A3A and a fragment that contained A3A with an intron were used. It was determined that when the intron was included it was much more likely to contain the originally designed sequence. Specifically, in this experiment, the deaminase was assembled with or without the intron as described and fused to a dCas12a enzyme (i.e., no nuclease activity) to create a Cas12a cytosine base editor via golden gate assembly. Following assembly, reactions were transformed into E. coli cells and the resulting clones sequenced by next generation sequencing. Of 6 constructs tested, when the intron was not present, only one (⅙) clone was detected through screening that had a 100% match with the intended sequence, whereas, when the intron was present, all of the clones (6/) had a 100% match with the intended sequence. The overall success rate was 20% when an intron was included in contrast to only 2% without an intron (Table 6).

TABLE 6

Summary of cloning results for the assembly of a cytosine deaminase vector

|  | Number of Colonies Screened | Correct Colonies (100% match to the expected sequence) | Success rate |
| --- | --- | --- | --- |
| A3A + intron | 90 | 18 | 20% |
| A3A | 176 | 3 | 2% |

Exemplary mutations identified among the potential clones of cytosine base editor assembly reactions are shown in Table 7.

TABLE 7

Example mutations found by sequencing potential clones of cytosine base editor assembly reactions

| Colony Name | UGI Region | A3A Region |
| --- | --- | --- |
| 1720_1-5 | correct | T missing in A3A |
| 1720_2-8 | correct | C missing in A3A |
| 1720_3-4 | no UGI | Linker missing |
| 1720_3-8 | Correct | A missing in A3A |
| 1720_6-8 | correct | C to G point mutation |
| 1720_7-8 | correct | No A3A |
| 1716_2-4 | correct | G missing in A3A |
| 1716_3-4 | correct | wrong UGI, missing linker, G missing in A3A |
| 1716_10-1 | correct | extra A in A3A |
| 1716_10-2 | correct | 2 sites incorrect |
| 1716_10-3 | correct | C missing in A3A |
| 1716_11-8 | correct | C missing in A3A |

Base Editing Using a Base Editor Construct Comprising an Intron

Figure 2:
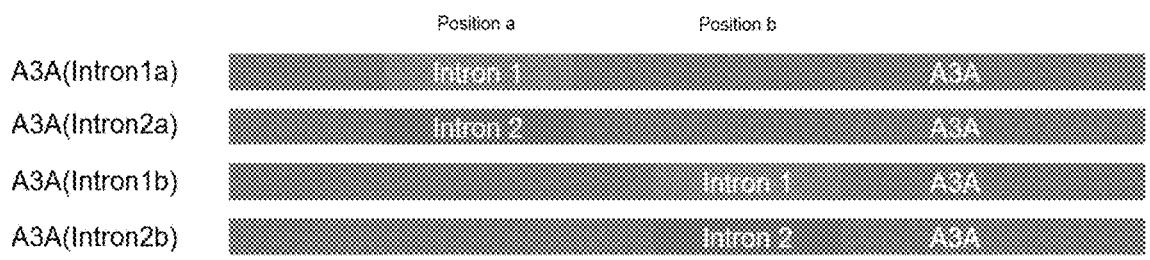
FIG. 2. Graphical representation of the architecture of the intron placement in the Apobec3A domain. Intron 1-Beta-globin/immunoglobin chimeric intron; Intron 2-SV40 intron FIG. 3. Comparison of base editing activity at the RNF2 locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C3, C6 and C12 are the positions of each of the cytosines that are edited in at the RNF2 locus.

Two different introns, the human chimeric intron discussed previously and the SV40 intron (Xu et al. *J. Cell Mol Med.* 22(4):2231-2239 (2018) (GTAAGTTTAGTCTTTTTGTCT TTTATTTCAGGTCCCGGATCCGGTGGTGGTGCAAAT-CAAAGAACTGCTCCTCAGT GGATGTTGCCTTTACTTCTAGGC) (SEQ ID NO:76), were introduced into the A3A deaminase and fused to a deactivated Cas9 protein. The introns were placed in two different regions of the deaminase domain (FIG. 2). Specifically, the intron was placed within the motif (A/C)AG [Intron]G(G/T), in order to maintain the canonical intron splicing sequence context. It is expected that other sites with this motif would also allow for efficient intron splicing.

Each base editor construct was compared against a base editor construct with the apobec1- or evoCDA1-deaminase at four loci in the human 293T cells, the RNF2 locus, the FANCF1 locus, AAVS1b locus and the AAVS1c locus. The results are shown in FIGS. 3-6.

Figure 3:
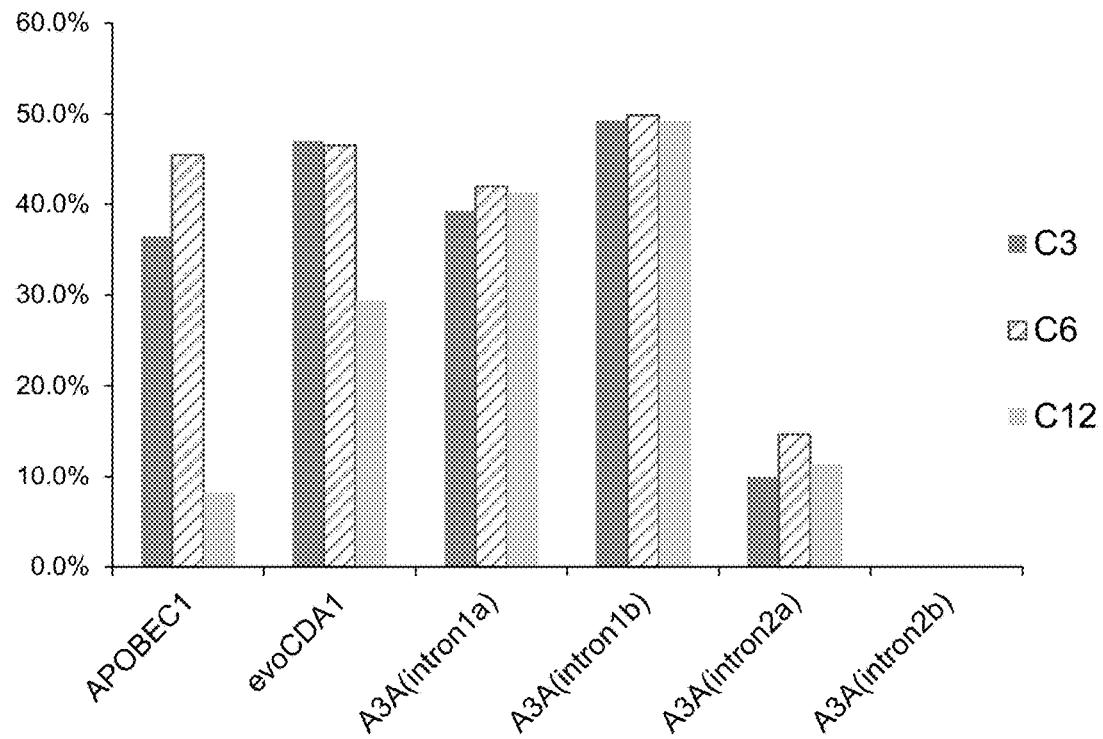
Figure 4:
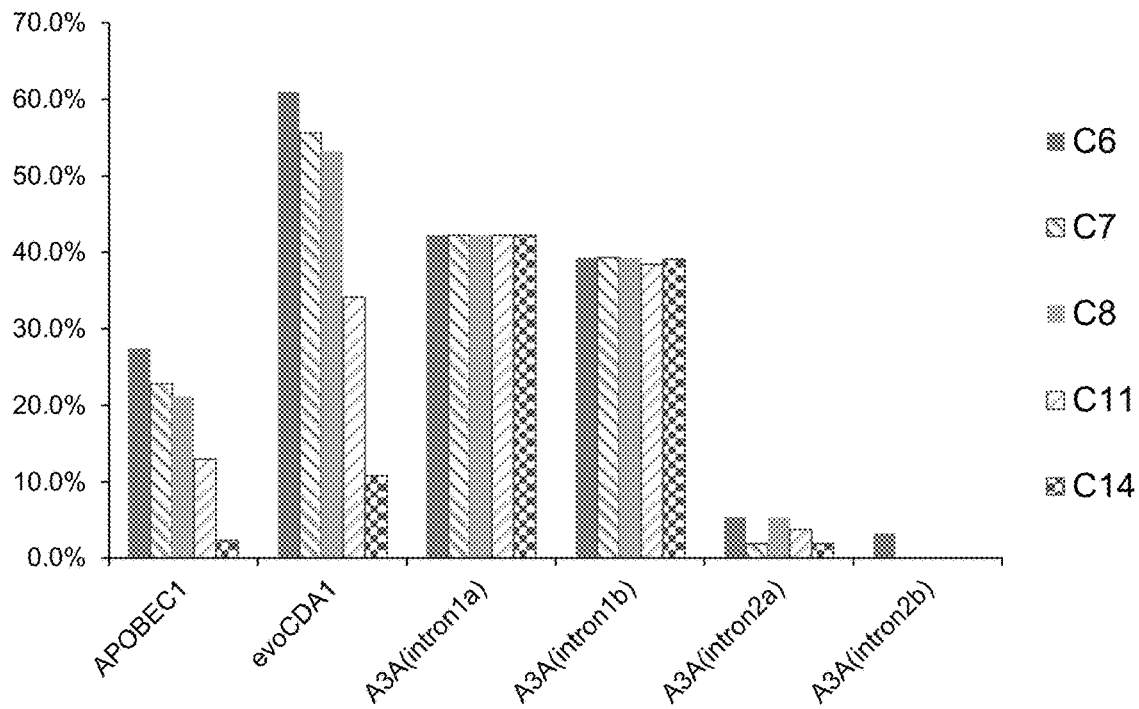
FIG. 4. Comparison of base editing activity with and without introns at the FANCF1 locus in human cells. Apobec1 and evoCDA1 deaminase constructs do not contain an intron, A3A constructs contain either the β-globulin/immunoglobulin chimeric intron (intron 1), or the SV40 intron (Intron 2). Y axis is % sequence reads with C>T conversions. C6, C7, C8, C11, and C14 are the cytosine positions at the FANCF1 locus.
Figure 5:
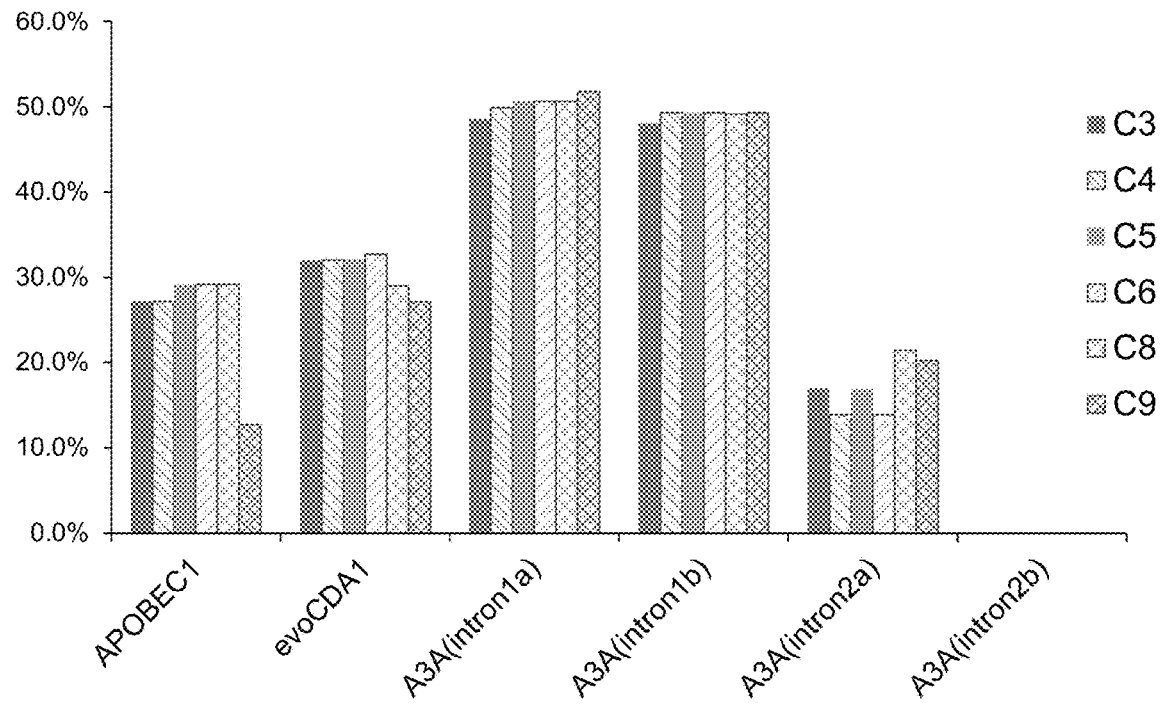
FIG. 5. Comparison of base editing activity with and without introns at the AAVS1b locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C3, C4, C5, C6, C8 and C9 are the positions of each of the cytosines that are edited in the AAVS1b locus.
Figure 6:
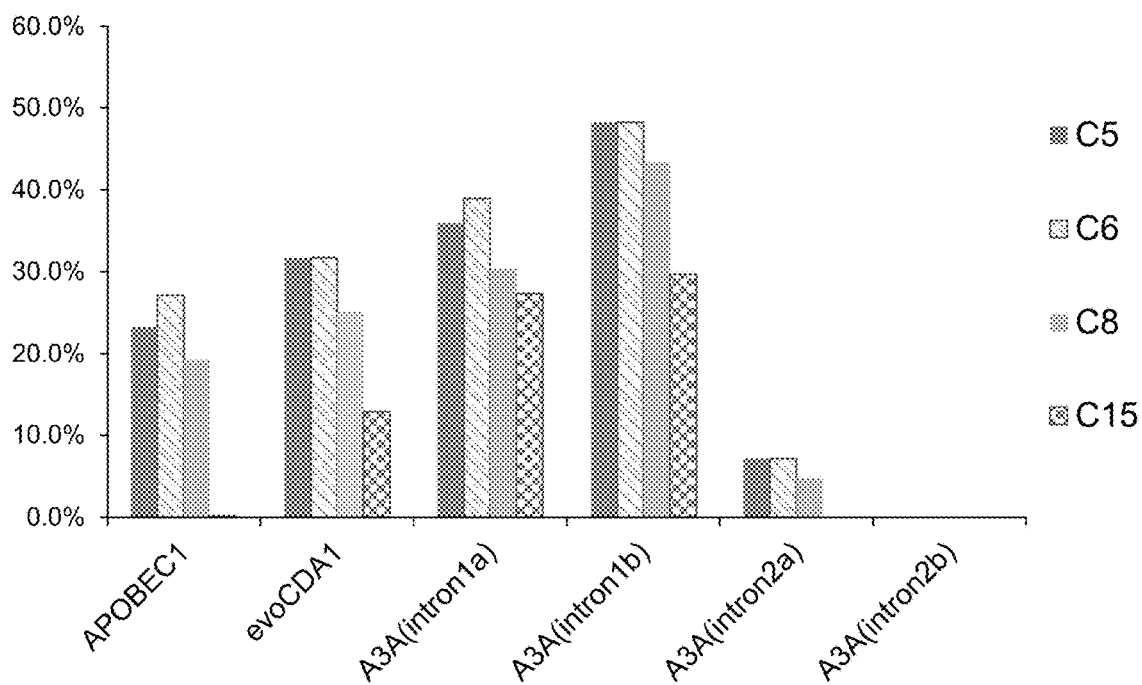
FIG. 6 Comparison of base editing activity at the AAVS1c locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C5, C6 C8 and C15 are the positions of each of the cytosines that are edited in the AAVS1c locus.

In FIG. 3, the base editing activity is shown using constructs with and without the introns. The editing is at the RNF2 locus in the human cells. The Apobec1 and evoCDA1 deaminase constructs do not contain an intron and the A3A constructs contain either the β-globulin/immunoglobulin chimeric intron (intron 1), or the SV40 intron (Intron 2). FIG. 4 shows a comparison of base editing activity at the FANCF1 locus in human cells for Apobec1 and evoCDA1 deaminase constructs that do not contain an intron, and A3A constructs that contain either the β-globulin/immunoglobulin chimeric intron (intron 1), or the SV40 intron (Intron 2). FIG. 8 compares base editing activity at the AAVS1b locus in human cells for Apobec1 and evoCDA1 deaminase constructs that do not contain an intron, and A3A constructs that contain either the β-globulin/immunoglobulin chimeric intron (intron 1), or the SV40 intron (Intron 2). In FIG. 9 base editing activity at the AAVS1c locus in human cells is compared for Apobec1 and evoCDA1 deaminase constructs that do not contain an intron, and A3A constructs that contain either the β-globulin/immunoglobulin chimeric intron (intron 1), or the SV40 intron (Intron 2). As shown in each of FIGS. 3-6, the chimeric intron resulted in base editing rates similar to editing rates without an intron, demonstrating that the presence of the intron is not preventing deaminase activity but with the advantage that constructs comprising intron as described herein can be produced without generating mutations in the vector sequence.

Example 5

Adenine base editors were constructed by placing the TadA deaminase and the variant TadA* directly 5' of a nickase variant of Cas9. The TadA and TadA* are separated by a protein linker, and there is an additional linker between the deaminase proteins and the start of nCas9. Similar to the cytosine base editors, the monocot vectors utilize the *Zea mays* Ubiquitin 1 promoter, and the dicot vectors utilize the *Medicago truncatula* Ubiquitin 2 promoter. These editor sequences were then codon optimized via proprietary algorithms for either corn and soy and the predicted sequences synthesized via solid state synthesis.

Nucleic acid constructs encoding an adenosine base editor that comprises a CRISPR-Cas nuclease and an adenine deaminase were generated (e.g., SEQ ID NOs:69-71). The nucleic acid constructs that were generated were codon optimized for expression in soybean (dicot, Di) or corn (monocot, Mon).

The constructs for optimized adenosine base editors as described herein are provided in Table 8.

TABLE 8

Optimized base editors

| Coding sequence optimized version | Plant Type |
| --- | --- |
| Mon_BY_V1_ABE (SEQ ID NO: 69) | Monocot |
| Di_BY_V1_ABE (SEQ ID NO: 70) | Dicot |
| Di_BY_V2_ABE (SEQ ID NO: 71) | Dicot |

TABLE 9

Editing efficiency of the base editors in corn and soy

| Target | Codon Optimization | Edited Plants | Total Samples | Editing Efficiency* |
|---|---|---|---|---|
| Corn Target 2 (Locus1) | Mon_BY_V1_ABE | 6 | 101 | 5.9% |
| Corn Target 2 (Locus2) | Mon_BY_V1_ABE | 18 | 101 | 17.8% |
| Soy Target 2 | Di_BY_V2_ABE | 1 | 46 | 2% |

*Editing over 10% of reads.

Editing in dicots with the V1_ABE was below the 10% cutoff used for higher-activity tools, however, activity was detected. Using a lower threshold of activity of 1%, the editing efficiency is shown in Table 10.

TABLE 10

Editing efficiency of the tested base editors in soy

| Target | Codon Optimization | Edited Plants | Total Samples | Editing Efficiency* |
|---|---|---|---|---|
| Soy Target 1 | Di_BY_V1_ABE | 11 | 235 | 4.6% |
| Soy Target 2 | Di_BY_V1_ABE | 31 | 235 | 13.2% |
| Soy Target 1 | Di_BY_V2_ABE | 0 | 46 | 0% |

*Editing over 1% of reads.

The foregoing is illustrative of the present invention, and is not to be construed as limiting thereof. The invention is defined by the following claims, with equivalents of the claims to be included therein.

What is claimed is:

1. A nucleic acid construct encoding a CRISPR-Cas nuclease operably associated with a promoter region, wherein the promoter region comprises an intron, optionally wherein the promoter region comprises a ubiquitin promoter and intron, wherein the nucleic acid construct encoding the CRISPR-Cas nuclease comprises the nucleotide sequence of SEQ ID NO:5.

2. The nucleic acid construct of claim 1, further encoding a deaminase domain.

3. The nucleic acid construct of claim 2, wherein the deaminase domain is codon optimized for expression in a plant.

4. The nucleic acid construct of claim 2, wherein the CRISPR-Cas nuclease and the deaminase domain are expressed as a fusion protein and the CRISPR-Cas nuclease is linked to the deaminase domain via a linker.

5. The nucleic acid construct of claim 2, wherein the deaminase domain is a cytosine deaminase domain or an adenosine deaminase domain.

6. The nucleic acid construct of claim 5, wherein the nucleic acid construct further encodes a uracil-DNA glycosylase inhibitor (UGI), optionally wherein the UGI is codon optimized for expression in a plant.

7. An expression cassette or vector comprising the nucleic acid construct of claim 1.

8. The expression cassette or vector of claim 7, further comprising a guide nucleic acid.

9. A cell comprising the nucleic acid construct of claim 1 and/or an expression cassette or vector comprising the nucleic acid construct.

10. The cell of claim 9, wherein the cell is a plant cell.

11. A method of modifying a target nucleic acid, comprising
contacting a cell or a cell free system comprising the target nucleic acid with:
(a) the nucleic acid construct of claim 2, or an expression cassette and/or vector comprising the same, and
(b) a guide nucleic acid, under conditions whereby the CRISPR-Cas nuclease encoded by the nucleic acid construct is expressed and forms a complex with the guide nucleic acid, the complex hybridizing to the target nucleic acid, thereby modifying the target nucleic acid.

12. The method of claim 11, wherein the deaminase domain is an adenine deaminase domain, and the adenine deaminase domain converts an adenosine (A) to a guanine (G) in the target nucleic acid, thereby editing the target nucleic acid to produce a mutation in the target nucleic acid.

13. The method of claim 12, wherein the mutation is an A-to-G conversion in the sense strand of the target nucleic acid or a T-to-C conversion in the antisense strand of the target nucleic acid.

14. The method of claim 11, wherein the deaminase domain is a cytosine deaminase domain, and the cytosine deaminase domain converts a cytosine (C) to a thiamine (T) in the target nucleic acid, thereby editing the target nucleic acid to produce a mutation.

15. A kit comprising the nucleic acid construct of claim 1, and/or an expression cassette or vector comprising the nucleic acid construct, optionally with instructions for the use thereof.

16. A nucleic acid construct encoding a CRISPR-Cas nuclease, wherein the nucleic acid construct comprises the nucleotide sequence of SEQ ID NO:5.

17. The nucleic acid construct of claim 16, further encoding a deaminase domain.

18. An expression cassette or vector comprising the nucleic acid construct of claim 16.

19. A cell comprising the nucleic acid construct of claim 16 and/or an expression cassette or vector comprising the nucleic acid construct of claim 16.

* * * * *

UNITED STATES PATENT AND TRADEMARK OFFICE
CERTIFICATE OF CORRECTION

PATENT NO. : 12,084,671 B2  
APPLICATION NO. : 18/164910  
DATED : September 10, 2024  
INVENTOR(S) : Nathaniel Graham Page 1 of 1

It is certified that error appears in the above-identified patent and that said Letters Patent is hereby corrected as shown below:

In the Specification

Column 11, Line 10: Please correct "Cash," to read --Cas6,--

Column 20, Line 3: Please correct "Cash," to read --Cas6,--

Column 27, Lines 63-65: Please delete and replace with the following:

```
5'-NNNNNNNNNNNNNNNNNNNNN-3' RNA Spacer (SEQ ID NO:64)
   | | | | | |  | | | | | | |  | | | | | |
3'AAANNNNNNNNNNNNNNNNNNNN-5' Target strand (SEQ ID NO:65)
   | | | |
5'TTTNNNNNNNNNNNNNNNNNNNN-3' Non-target strand (SEQ ID NO:66)
```

Signed and Sealed this  
Twenty-fourth Day of December, 2024

Derrick Brent  
*Acting Director of the United States Patent and Trademark Office*